US010428326B2

(12) United States Patent
Belhocine et al.

(10) Patent No.: US 10,428,326 B2
(45) Date of Patent: Oct. 1, 2019

(54) METHODS AND SYSTEMS FOR DROPLET-BASED SINGLE CELL BARCODING

(71) Applicant: 10X Genomics, Inc., Pleasanton, CA (US)

(72) Inventors: Kamila Belhocine, Fremont, CA (US); Rajiv Bharadwaj, Pleasanton, CA (US); Christopher Hindson, Pleasanton, CA (US); Michael Schnall-Levin, San Francisco, CA (US); Bill Lin, Pleasanton, CA (US); Anthony Makarewicz, Livermore, CA (US); Pranav Patel, Fremont, CA (US); Katherine Pfeiffer, Berkeley, CA (US); Andrew D. Price, Hayward, CA (US); Mohammad Rahimi Lenji, Pleasanton, CA (US); Tobias Daniel Wheeler, Alameda, CA (US); Yifeng Yin, Elk Grove, CA (US)

(73) Assignee: 10X GENOMICS, INC., Pleasanton, CA (US)

(*) Notice: Subject to any disclaimer, the term of this patent is extended or adjusted under 35 U.S.C. 154(b) by 0 days.

(21) Appl. No.: 15/887,947

(22) Filed: Feb. 2, 2018

(65) Prior Publication Data
US 2018/0216162 A1 Aug. 2, 2018

Related U.S. Application Data

(63) Continuation of application No. PCT/US2018/016019, filed on Jan. 30, 2018.

(60) Provisional application No. 62/452,261, filed on Jan. 30, 2017, provisional application No. 62/500,943, filed on May 3, 2017, provisional application No. 62/570,783, filed on Oct. 11, 2017.

(51) Int. Cl.
*C12N 15/10* (2006.01)
*C12Q 1/6806* (2018.01)
*C12Q 1/6869* (2018.01)

(52) U.S. Cl.
CPC ....... *C12N 15/1065* (2013.01); *C12Q 1/6806* (2013.01); *C12Q 1/6869* (2013.01)

(58) Field of Classification Search
CPC .................................................. C12N 15/1065
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |
| 3,479,141 A | 11/1969 | Smythe et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |

(Continued)

FOREIGN PATENT DOCUMENTS

| | | |
|---|---|---|
| CN | 102292455 A | 12/2011 |
| CN | 103202812 A | 7/2013 |

(Continued)

OTHER PUBLICATIONS

Lai et al. Characterization and use of laser-based lysis for cell analysis on-chip. Journal of the Royal Society, Interface, vol. 5, Supplement 2, pp. S113-S121, Oct. 2008. (Year: 2008).*
Co-pending U.S. Appl. No. 15/933,299, filed Mar. 22, 2018.
Co-pending U.S. Appl. No. 15/975,468, filed May 9, 2018
Co-pending U.S. Appl. No. 15/980,473, filed May 15, 2018.
Co-pending U.S. Appl. No. 15/985,388, filed May 21, 2018.
Han, SW et al. "Targeted Sequencing of Cancer-Related Genes in Colorectal Cancer Using Next-Generation Sequencing" PLOS One (2013) 8(5):e64271.
Lander, et al. Initial sequencing and analysis of the human genome. Nature, 409 (Feb. 15, 2001): 860-921.
Shaikh, et al. A modular microfluidic architecture for integrated biochemical analysis. Proc Natl Acad Sci U S A. Jul. 12, 2005;102(28):9745-50. Epub Jun. 28, 2005.

(Continued)

*Primary Examiner* — Jennifer Dunston
(74) *Attorney, Agent, or Firm* — Wilson Sonsini Goodrich & Rosati

(57) ABSTRACT

Methods and systems are provided for sample preparation techniques and sequencing of macromolecular constituents of cells and other biological materials.

37 Claims, 36 Drawing Sheets

(56) References Cited

U.S. PATENT DOCUMENTS

| | | | |
|---|---|---|---|
| 5,942,609 | A | 8/1999 | Hunkapiller et al. |
| 5,958,703 | A | 9/1999 | Dower et al. |
| 5,965,443 | A | 10/1999 | Reznikoff et al. |
| 5,994,056 | A | 11/1999 | Higuchi |
| 5,997,636 | A | 12/1999 | Gamarnik et al. |
| 6,033,880 | A | 3/2000 | Haff et al. |
| 6,046,003 | A | 4/2000 | Mandecki |
| 6,051,377 | A | 4/2000 | Mandecki |
| 6,057,107 | A | 5/2000 | Fulton |
| 6,057,149 | A | 5/2000 | Burns et al. |
| 6,103,537 | A | 8/2000 | Ullman et al. |
| 6,133,436 | A | 10/2000 | Koester et al. |
| 6,143,496 | A | 11/2000 | Brown et al. |
| 6,159,717 | A | 12/2000 | Savakis et al. |
| 6,171,850 | B1 | 1/2001 | Nagle et al. |
| 6,172,218 | B1 | 1/2001 | Brenner |
| 6,207,384 | B1 | 3/2001 | Mekalanos et al. |
| 6,258,571 | B1 | 7/2001 | Chumakov et al. |
| 6,265,552 | B1 | 7/2001 | Schatz |
| 6,291,243 | B1 | 9/2001 | Fogarty et al. |
| 6,294,385 | B1 | 9/2001 | Goryshin et al. |
| 6,296,020 | B1 | 10/2001 | McNeely et al. |
| 6,297,006 | B1 | 10/2001 | Drmanac et al. |
| 6,297,017 | B1 | 10/2001 | Schmidt et al. |
| 6,303,343 | B1 | 10/2001 | Kopf-Sill |
| 6,306,590 | B1 | 10/2001 | Mehta et al. |
| 6,327,410 | B1 | 12/2001 | Walt et al. |
| 6,355,198 | B1 | 3/2002 | Kim et al. |
| 6,361,950 | B1 | 3/2002 | Mandecki |
| 6,372,813 | B1 | 4/2002 | Johnson et al. |
| 6,379,929 | B1 | 4/2002 | Burns et al. |
| 6,406,848 | B1 | 6/2002 | Bridgham et al. |
| 6,409,832 | B2 | 6/2002 | Weigl et al. |
| 6,432,290 | B1 | 8/2002 | Harrison et al. |
| 6,432,360 | B1 | 8/2002 | Church |
| 6,485,944 | B1 | 11/2002 | Church et al. |
| 6,492,118 | B1 | 12/2002 | Abrams et al. |
| 6,511,803 | B1 | 1/2003 | Church et al. |
| 6,524,456 | B1 | 2/2003 | Ramsey et al. |
| 6,569,631 | B1 | 5/2003 | Pantoliano et al. |
| 6,579,851 | B2 | 6/2003 | Goeke et al. |
| 6,586,176 | B1 | 7/2003 | Trnovsky et al. |
| 6,593,113 | B1 | 7/2003 | Tenkanen et al. |
| 6,613,752 | B2 | 9/2003 | Kay et al. |
| 6,632,606 | B1 | 10/2003 | Ullman et al. |
| 6,632,655 | B1 | 10/2003 | Mehta et al. |
| 6,670,133 | B2 | 12/2003 | Knapp et al. |
| 6,723,513 | B2 | 4/2004 | Lexow |
| 6,767,731 | B2 | 7/2004 | Hannah |
| 6,800,298 | B1 | 10/2004 | Burdick et al. |
| 6,806,052 | B2 | 10/2004 | Bridgham et al. |
| 6,806,058 | B2 | 10/2004 | Jesperson et al. |
| 6,859,570 | B2 | 2/2005 | Walt et al. |
| 6,880,576 | B2 | 4/2005 | Karp et al. |
| 6,884,788 | B2 | 4/2005 | Bulpitt et al. |
| 6,913,935 | B1 | 7/2005 | Thomas |
| 6,929,859 | B2 | 8/2005 | Chandler et al. |
| 6,969,488 | B2 | 11/2005 | Bridgham et al. |
| 6,974,669 | B2 | 12/2005 | Mirkin et al. |
| 7,041,481 | B2 | 5/2006 | Anderson et al. |
| 7,115,400 | B1 | 10/2006 | Adessi et al. |
| 7,129,091 | B2 | 10/2006 | Ismagilov et al. |
| 7,138,267 | B1 | 11/2006 | Jendrisak et al. |
| 7,211,654 | B2 | 5/2007 | Gao et al. |
| 7,268,167 | B2 | 9/2007 | Higuchi et al. |
| 7,282,370 | B2 | 10/2007 | Bridgham et al. |
| 7,294,503 | B2 | 11/2007 | Quake et al. |
| 7,297,485 | B2 | 11/2007 | Bornarth et al. |
| 7,316,903 | B2 | 1/2008 | Yanagihara et al. |
| 7,323,305 | B2 | 1/2008 | Leamon et al. |
| 7,329,493 | B2 | 2/2008 | Chou et al. |
| 7,425,431 | B2 | 9/2008 | Church et al. |
| 7,536,928 | B2 | 5/2009 | Kazuno |
| 7,544,473 | B2 | 6/2009 | Brenner |
| 7,604,938 | B2 | 10/2009 | Takahashi et al. |
| 7,608,434 | B2 | 10/2009 | Reznikoff et al. |
| 7,608,451 | B2 | 10/2009 | Cooper et al. |
| 7,622,280 | B2 | 11/2009 | Holliger et al. |
| 7,638,276 | B2 | 12/2009 | Griffiths et al. |
| 7,645,596 | B2 | 1/2010 | Williams et al. |
| 7,666,664 | B2 | 2/2010 | Sarofim et al. |
| 7,700,325 | B2 | 4/2010 | Cantor et al. |
| 7,708,949 | B2 | 5/2010 | Stone et al. |
| 7,709,197 | B2 | 5/2010 | Drmanac |
| 7,745,178 | B2 | 6/2010 | Dong |
| 7,745,218 | B2 | 6/2010 | Kim et al. |
| 7,776,927 | B2 | 8/2010 | Chu et al. |
| RE41,780 | E | 9/2010 | Anderson et al. |
| 7,799,553 | B2 | 9/2010 | Mathies et al. |
| 7,842,457 | B2 | 11/2010 | Berka et al. |
| 7,901,891 | B2 | 3/2011 | Drmanac |
| 7,910,354 | B2 | 3/2011 | Drmanac et al. |
| 7,947,477 | B2 | 5/2011 | Schroeder et al. |
| 7,960,104 | B2 | 6/2011 | Drmanac et al. |
| 7,968,287 | B2 | 6/2011 | Griffiths et al. |
| 7,972,778 | B2 | 7/2011 | Brown et al. |
| 8,003,312 | B2 | 8/2011 | Krutzik et al. |
| 8,008,018 | B2 | 8/2011 | Quake et al. |
| 8,053,192 | B2 | 11/2011 | Bignell et al. |
| 8,067,159 | B2 | 11/2011 | Brown et al. |
| 8,101,346 | B2 | 1/2012 | Takahama |
| 8,124,404 | B2 | 2/2012 | Alphey |
| 8,133,719 | B2 | 3/2012 | Drmanac et al. |
| 8,137,563 | B2 | 3/2012 | Ma et al. |
| 8,168,385 | B2 | 5/2012 | Brenner |
| 8,252,539 | B2 | 8/2012 | Quake et al. |
| 8,268,564 | B2 | 9/2012 | Roth et al. |
| 8,273,573 | B2 | 9/2012 | Ismagilov et al. |
| 8,278,071 | B2 | 10/2012 | Brown et al. |
| 8,298,767 | B2 | 10/2012 | Brenner et al. |
| 8,304,193 | B2 | 11/2012 | Ismagilov et al. |
| 8,318,433 | B2 | 11/2012 | Brenner |
| 8,318,460 | B2 | 11/2012 | Cantor et al. |
| 8,329,407 | B2 | 12/2012 | Ismagilov et al. |
| 8,337,778 | B2 | 12/2012 | Stone et al. |
| 8,361,299 | B2 | 1/2013 | Sabin et al. |
| 8,420,386 | B2 | 4/2013 | Ivics et al. |
| 8,461,129 | B2 | 6/2013 | Bolduc et al. |
| 8,563,274 | B2 | 10/2013 | Brenner et al. |
| 8,592,150 | B2 | 11/2013 | Drmanac et al. |
| 8,598,328 | B2 | 12/2013 | Koga et al. |
| 8,603,749 | B2 | 12/2013 | Gillevet |
| 8,679,756 | B1 | 3/2014 | Brenner et al. |
| 8,748,094 | B2 | 6/2014 | Weitz et al. |
| 8,748,102 | B2 | 6/2014 | Berka et al. |
| 8,765,380 | B2 | 7/2014 | Berka et al. |
| 8,822,148 | B2 | 9/2014 | Ismagliov et al. |
| 8,829,171 | B2 | 9/2014 | Steemers et al. |
| 8,835,358 | B2 | 9/2014 | Fodor et al. |
| 8,871,444 | B2 | 10/2014 | Griffiths et al. |
| 8,889,083 | B2 | 11/2014 | Ismagilov et al. |
| 8,927,218 | B2 | 1/2015 | Forsyth |
| 8,975,302 | B2 | 3/2015 | Light et al. |
| 8,986,286 | B2 | 3/2015 | Tanghoj et al. |
| 9,005,935 | B2 | 4/2015 | Belyaev |
| 9,012,390 | B2 | 4/2015 | Holtze et al. |
| 9,017,948 | B2 | 4/2015 | Agresti et al. |
| 9,029,083 | B2 | 5/2015 | Griffiths et al. |
| 9,029,085 | B2 | 5/2015 | Agresti et al. |
| 9,068,210 | B2 | 6/2015 | Agresti et al. |
| 9,074,251 | B2 | 7/2015 | Steemers et al. |
| 9,080,211 | B2 | 7/2015 | Grunenwald et al. |
| 9,102,980 | B2 | 8/2015 | Brenner et al. |
| 9,150,916 | B2 | 10/2015 | Christen et al. |
| 9,175,295 | B2 | 11/2015 | Kaminaka et al. |
| 9,238,671 | B2 | 1/2016 | Goryshin et al. |
| 9,249,460 | B2 | 2/2016 | Pushkarev et al. |
| 9,273,349 | B2 | 3/2016 | Nguyen et al. |
| 9,290,808 | B2 | 3/2016 | Fodor et al. |
| 9,328,382 | B2 | 5/2016 | Drmanac et al. |
| 9,347,059 | B2 | 5/2016 | Saxonov |
| 9,388,465 | B2 | 7/2016 | Hindson et al. |
| 9,410,201 | B2 | 8/2016 | Hindson et al. |
| 9,436,088 | B2 | 9/2016 | Seul et al. |

(56) References Cited

U.S. PATENT DOCUMENTS

| | | |
|---|---|---|
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 1,011,916 A1 | 11/2018 | Srinivasan et al. |
| 10,137,449 B2 | 11/2018 | Bharadwaj et al. |
| 1,014,495 A1 | 12/2018 | Nolan |
| 10,150,995 B1 | 12/2018 | Giresi et al. |
| 1,017,431 A1 | 1/2019 | Nolan |
| 10,227,648 B2 | 3/2019 | Hindson et al. |
| 1,025,336 A1 | 4/2019 | Hindson et al. |
| 1,027,354 A1 | 4/2019 | Hindson et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101680 A1 | 5/2004 | Barber et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0026401 A1* | 2/2007 | Hofmann ............ A61L 2/0011 435/6.11 |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0141584 A1 | 6/2007 | Roberts et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2008/0268507 A1 | 10/2008 | Xu et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |

(56) References Cited

U.S. PATENT DOCUMENTS

| | | |
|---|---|---|
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van Der Zaag et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0289428 A1 | 11/2012 | Duffy et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0109596 A1 | 5/2013 | Peterson et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum |
| 2013/0274117 A1 | 10/2013 | Church et al. |
| 2013/0296173 A1 | 11/2013 | Callow et al. |
| 2013/0343317 A1 | 12/2013 | Etemad et al. |
| 2013/0344508 A1 | 12/2013 | Schwartz et al. |
| 2014/0030350 A1 | 1/2014 | Ashrafi et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0080717 A1 | 3/2014 | Li et al. |
| 2014/0093916 A1 | 4/2014 | Belyaev et al. |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |

(56) References Cited

U.S. PATENT DOCUMENTS

| | | |
|---|---|---|
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0211056 A1 | 7/2015 | Um et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225786 A1 | 8/2015 | Litterst et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0025726 A1 | 1/2016 | Altin et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244811 A1 | 8/2016 | Edwards |
| 2016/0244825 A1 | 8/2016 | Vigneault et al. |
| 2016/0257984 A1 | 9/2016 | Hardenbol et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0211127 A1 | 7/2017 | Mikkelsen et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0057868 A1 | 3/2018 | Walder et al. |
| 2018/0087050 A1 | 3/2018 | Zheng et al. |
| 2018/0088112 A1 | 3/2018 | Fan et al. |
| 2018/0112253 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0267036 A1 | 9/2018 | Fan et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0327839 A1 | 11/2018 | Hindson et al. |
| 2018/0335424 A1 | 11/2018 | Chen et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0346979 A1 | 12/2018 | Hindson et al. |
| 2018/0376609 A1 | 12/2018 | Ju et al. |
| 2019/0032130 A1 | 1/2019 | Giresi et al. |
| 2019/0040464 A1 | 2/2019 | Giresi et al. |
| 2019/0085391 A1 | 3/2019 | Hindson et al. |
| 2019/0127731 A1 | 5/2019 | McDermott |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0153436 A1 | 5/2019 | Belhocine et al. |
| 2019/0153532 A1 | 5/2019 | Bharadwaj et al. |

FOREIGN PATENT DOCUMENTS

| | | |
|---|---|---|
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| WO | WO-8402000 A1 | 5/1984 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9942597 A1 | 8/1999 |

(56) References Cited

FOREIGN PATENT DOCUMENTS

| | | |
|---|---|---|
| WO | WO-9952708 A1 | 10/1999 |
| WO | WO-0008212 A1 | 2/2000 |
| WO | WO-0023181 A1 | 4/2000 |
| WO | WO-0026412 A1 | 5/2000 |
| WO | WO-0034527 A2 | 6/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006071770 A2 | 7/2006 |
| WO | WO-2006078841 A1 | 7/2006 |
| WO | WO-2006086210 A2 | 8/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008135512 A2 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009048532 A2 | 4/2009 |
| WO | WO-2009061372 A1 | 5/2009 |
| WO | WO-2009085215 A1 | 7/2009 |
| WO | WO-2009147386 A1 | 12/2009 |
| WO | WO-2010004018 A2 | 1/2010 |
| WO | WO-2010009735 A2 | 1/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011140627 A1 | 11/2011 |
| WO | WO-2012012037 A1 | 1/2012 |
| WO | WO-2012047889 A2 | 4/2012 |
| WO | WO-2012048340 A2 | 4/2012 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014028537 A1 | 2/2014 |
| WO | WO-2014053854 A1 | 4/2014 |
| WO | WO-2014071361 A1 | 5/2014 |
| WO | WO-2014072703 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014145047 A1 | 9/2014 |
| WO | WO-2014150931 A1 | 9/2014 |
| WO | WO-2014182835 A1 | 11/2014 |
| WO | WO-2014189957 A2 | 11/2014 |
| WO | WO-2014200767 A1 | 12/2014 |
| WO | WO-2014210353 A2 | 12/2014 |
| WO | WO-2015031691 A1 | 3/2015 |
| WO | WO-2015044428 A1 | 4/2015 |
| WO | WO-2015164212 A1 | 10/2015 |
| WO | WO-2015185067 A1 | 12/2015 |
| WO | WO-2015188839 A2 | 12/2015 |
| WO | WO-2015200893 A2 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016168584 A1 | 10/2016 |
| WO | WO-2016176322 A1 | 11/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017053902 A1 | 3/2017 |
| WO | WO-2017053903 A1 | 3/2017 |
| WO | WO-2017053905 A1 | 3/2017 |
| WO | WO-2017075265 A1 | 5/2017 |
| WO | WO-2017075294 A1 | 5/2017 |
| WO | WO-2017151828 A1 | 9/2017 |
| WO | WO-2017156336 A1 | 9/2017 |
| WO | WO-2017180420 A1 | 10/2017 |
| WO | WO-2018045186 A1 | 3/2018 |
| WO | WO-2018058073 A2 | 3/2018 |

(56) References Cited

FOREIGN PATENT DOCUMENTS

| WO | WO-2018103025 A1 | 6/2018 | |
|---|---|---|---|
| WO | WO-2018119301 A1 * | 6/2018 | ............. C12P 19/30 |
| WO | WO-2018119447 A2 | 6/2018 | |
| WO | WO-2019084328 A1 | 5/2019 | |
| WO | WO-2019099751 A1 | 5/2019 | |

OTHER PUBLICATIONS

Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Wong, et al. Multiplexed Barcoded CRISPR-Cas9 Screening Enabled by CombiGEM. PNAS. Mar. 1, 2016, vol. 113, pp. 2544-2549.
Zhu, et al. Reverse transcriptase template switching: a SMART approach for full-length cDNA library construction. Biotechniques. Apr. 2001;30(4):892-7.
Adamson et al., "Production of arrays of chemically distinct nanolitre plugs via repeated splitting in microfluidic devices", Lab Chip 6(9): 1178-1186 (Sep. 2006).
Fu, et al. A Microfabricated Fluorescence-Activated Cell Sorter. Nature Biotechnology.1999; 17:1109-1111.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Kolodeziejczyk et al., "The technology and biology of single-cell RNA sequencing", Molecular Cell, vol. 58 (May 21, 2015).
Lee et al. Alginate: Properties and biomedical applications. Prog Polym Sci 37(1):106-126 (2012).
Morimoto, et al. Monodisperse semi-permeable microcapsules for continuous observation of cells. 2009. Lab Chip 9(15):2217-2223.
Narayanan, J. et al. "Determination of agarose gel pore size: Absorbance measurements vis a vis other techniques" Journal of Physics: Conference Series 28 (2006) 83-86 (Year: 2006).
Xia and Whitesides, Soft Lithography, Angew. Chem. Int. Ed. 37:550-575 (1998).
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adey, et al. Rapid, low-input, low-bias construction of shotgun fragment libraries by high-density in vitro transposition. Genome Biology 11:R119 (2010).
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Ahern, "Biochemical, Reagents Kits Offer Scientists Good Return on Investment" The Scientist (1995) 9(15):1-7.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Biol., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna, S.L., et al., "Formation of dispersions using "flow focusing" in microchannels," Applied Physics Letters, vol. 82, No. 3, pp. 364-366 (2003).
Anonymous, "Oligo(dT)25 cellulose beads" NEB (2012) Retrieved from the Internet:https://www.neb.com/~/media/Catalog/All-Products/286CA51268E24DE1B06F1CB2886981354/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Attia, et al. Micro-injection moulding of polymer microfluidic devices. Microfluidics and nanofluidics. 2009; 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2010;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al, "Massively parallel haplotyping on microscopic beads for the high-throughput phase analysis of single molecules", PLoS One, vol. 7:1-10, 2012.

(56) References Cited

OTHER PUBLICATIONS

Braeckmans et al., Scanning the Code. Modern Drug Discovery. 2003:28-32.
Bransky, et al. A microfluidic droplet generator based on a piezo-electric actuator. Lab Chip. Feb. 21, 2009;9(4):516-20. doi: 10.1039/b814810d. Epub Nov. 20, 2008.
Brenner, et al. In vitro cloning of complex mixtures of DNA on microbeads: physical separation of differentially expressed cDNAs. Proc Natl Acad Sci U S A. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109, Jan. 2015
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio N., Preparation of Next-Generation Sequencing Libraries Using Nextera Technology: Simultaneous DNA Fragmentation and Adaptor Tagging by in Vitro Transposition. Ch. 17 Methods in Microbiology 733:241 (2011).
Casbon, et al, "Reflex: intramolecular barcoding of long-range PCR products for sequencing multiple pooled DNAs", Nucleic Acids Res., pp. 1-6, 2013.
Chang et al. Droplet-based microfluidic platform platform for heterogeneous enzymatic assays, 2013, Lab Chip, 13, 1817-1822 (Year: 2013).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;I8(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011

Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics. 2010;186:757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Cong, et al. Multiplex genome engineering using CRISPR/Cas systems. Science. Feb. 15, 2013;339(6121):819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/718,764, filed Sep. 28, 2017.
Co-pending U.S. Appl. No. 15/718,893, filed Sep. 28, 2017.
Co-pending U.S. Appl. No. 15/720,085, filed Sep. 29, 2017.
Co-pending U.S. Appl. No. 15/825,740, filed Nov. 29, 2017.
Co-pending U.S. Appl. No. 15/831,726, filed Dec. 5, 2017.
Co-pending U.S. Appl. No. 15/831,847, filed Dec. 5, 2017.
Co-pending U.S. Appl. No. 15/832,183, filed Dec. 5, 2017.
Co-pending U.S. Appl. No. 15/832,547, filed Dec. 5, 2017.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.
Co-pending U.S. Appl. No. 15/847,659, filed Dec. 19, 2017.
Co-pending U.S. Appl. No. 15/847,752, filed Dec. 19, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/872,499, filed Jan. 16, 2018.
Co-pending U.S. Appl. No. 15/875,899, filed Jan. 19, 2018.
Co-pending U.S. Appl. No. 15/887,711, filed Feb. 2, 2018.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Cusanovich; et al., "Multiplex single-cell profiling of chromatin accessibility by combinatorial cellular indexing. Sciencexpress, May 7, 2014, p. 1-9."
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.
Dekker, et al. Capturing chromosome conformation. Science. Feb. 15, 2002;295(5558):1306-11.
Demirci, et al. Single cell epitaxy by acoustic picolitre droplets. Lab Chip. Sep. 2007;7(9):1139-45. Epub Jul. 10, 2007.

(56) References Cited

OTHER PUBLICATIONS

Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fulton et al., Advanced multiplexed analysis with the FlowMetrix system. Clin Chem. Sep. 1997;43(9): 1749-56.
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.

Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci U S A. Apr. 10, 2001;98(8):4552-7. Epub Mar. 27, 2001.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamilton, A.J. "microRNA in erythrocytes" Biochem. Soc. Trans. (2010) 38, 229-231.
Han, X. et al. "CRISPR-Cas9 delivery to hard-to-transfect cells via membrane deformation" Science Advances (2015) 1(7): E1500454 (8 pages).
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5):954-64. Epub Apr. 14, 2003.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to the University of Birmingham for the degree of Doctor of Philosophy. 2009.
Jena, et al. Cyclic olefin copolymer based microfluidic devices for biochip applications: Ultraviolet surface grafting using

(56) References Cited

OTHER PUBLICATIONS 2-methacryloyloxyethyl phosphorylcholine. Biomicrofluidics. Mar. 2012;6(1):12822-1282212. doi: 10.1063/1.3682098. Epub Mar. 15, 2012

Jung, et al. Micro machining of injection mold inserts for fluidic channel of polymeric biochips. Sensors. 2007; 7(8):1643-1654.

Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.

Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.

Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.

Katsura, et al. Indirect micromanipulation of single molecules in water-in-oil emulsion. Electrophoresis. Jan. 2001;22(2):289-93.

Kebschull, et al. High-Throughput Mapping of Single-Neuron Projections by Sequencing of Barcoded RNA. Neuron. Sep. 7. 2016;91(5):975-87. doi: 10.1016/j.neuron.2016.07.036. Epub Aug. 18, 2016.

Kenis, et al. Microfabrication Inside Capillaries Using Multiphase Laminar Flow Patterning. Science. Jul. 2, 1999;285(5424):83-5.

Khomiakova et al., Analysis of perfect and mismatched DNA duplexes by a generic hexanucleotide microchip. Mol Biol(Mosk). Jul.-Aug. 2003;37(4):726-41. Russian. Abstract only.

Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.

Kim, et al. Fabrication of monodisperse gel shells and functional microgels in microfluidic devices. Angew Chem Int Ed Engl. 2007;46(11):1819-22.

Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.

Kirkness et al. "Sequencing of isolated sperm cells for direct haplotyping of a human genome," Genome Res (2013) 23:826-832.

Kitzman et al. "Haplotype-resolved genome sequencing of a Gujarati Indian individual." Nat Biotechnol (2011) 29:59-63.

Kitzman, et al. Noninvasive whole-genome sequencing of a human fetus. Sci Transl Med. Jun. 6, 2012;4(137):137ra76. doi: 10.1126/scitranslmed.3004323.

Kivioj, et al., "Counting Absolute Numbers of Molecules Using Unique Molecular Identifiers", Nature Methods 9, 72-74 (2012).

Klein, et al. Droplet barcoding for single-cell transcriptomics applied to embryonic stem cells. Cell. May 21, 2015;161(5):1187-201. doi: 10.1016/j.cell.2015.04.044.

Knight, et al. Subtle chromosomal rearrangements in children with unexplained mental retardation. Lancet. Nov. 13, 1999;354(9191):1676-81.

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip the Royal Soc. of Chern. 8: 1110-1115 (2008).

Kozarewa, et al, "96-plex molecular barcoding for the Illumina Genome Analyzer", Methods Mol Biol., 733:279-98, 2011.

Kozarewa, et al. "Amplification-free Illumina sequencing-library preparation facilitates improved mapping and assembly of GC-biased genomes", Nat Methods., 6: 291-5, 2009.

Kutyavin, et al. Oligonucleotides containing 2-aminoadenine and 2-thiothymine act as selectively binding complementary agents. Biochemistry. Aug. 27, 1996;35(34):11170-6.

Kwok, et al, "Single-molecule analysis for molecular haplotyping", Hum Mutat., 23:442-6, 2004.

Lagally, et al. Single-Molecular DNA Amplification and Analysis in an Integrated Microfluidic Device. Anal Chem. Feb. 1, 2001;73(3):565-70.

Lagus, et al. A review of the theory, methods and recent applications of high-throughput single-cell droplet microfluidics. J. Phys. D: Appl. Phys. (2013) 46:114005. (21 pages).

Laird et al, Hairpin-bisulfite PCR: Assessing epigenetic methylation patterns on complementary strands of individual DNA molecules, 2004, PNAS, 101, 204-209.

Lake, et al. "Integrative Single-Cell Analysis by Transcriptional and Epigenetic States in Human Adult Brain". Apr. 19, 2017. doi: https://doi.org/10.1101/128520.

Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].

Lasken, et al. (1996) Archaebacterial DNA Polymerases Tightly Bind Uracil-containing DNA. The Journal of Biological Chemistry, 271(30):17692-17696 (Year: 1996).

Lee, et al. ACT-PRESTO: Rapid and consistent tissue clearing and labeling method for 3-dimensional (3D) imaging. Sci Rep. Jan. 11, 2016;6:18631. doi: 10.1038/srep18631.

Lee, et al., "Highly multiplexed subcellular RNA sequencing in situ. Science. Mar. 21, 2014;343(6177):1360-3. doi: 10.1126/science.1250212. Epub Feb. 27, 2014."

Lee, J-H. et al. "Fluorescent in situ sequencing (FISSEQ) of RNA for gene expression profiling in intact cells and tissues" Nature Protocols (Feb. 12, 2015) 10(3):442-458.

Lennon; et al., "Lennon et al. A scalable, fully automated process for construction of sequence-ready barcoded libraries for 454. Genome Biology 11:R15 (2010)."

Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].

Li, Y., et al., "PEGylated PLGA Nanoparticles as protein carriers: synthesis, preparation and biodistribution in rats," Journal of Controlled Release, vol. 71, pp. 203-211 (2001).

Lienemann, et al. Single cell-laden protease-sensitive microniches for long-term culture in 3D. Lab Chip. Feb. 14, 2017;17(4):727-737. doi: 10.1039/c6lc01444e.

Linch, et al. Bone marrow processing and cryopreservation. Journal of Clinical Pathology; Feb. 1982, vol. 35, No. 2; pp. 186-190.

Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.

Liu, et al. Smart thermo-triggered squirting capsules for Nanoparticle delivery. Soft Matter. 2010; 6(16):3759-3763.

Lo, et al. On the design of clone-based haplotyping. Genome Biol. 2013;14(9):R100.

Loscertales, I.G., et al., "Micro/Nano Encapsulation via Electrified Coaxial Liquid Jets," Science, vol. 295, pp. 1695-1698 (2002).

Love, "A microengraving method for rapid selection of single cells producing antigen-specific antibodies", Nature Biotech, 24:6 703 (Jun. 2006).

Lowe, Adam J. Norbornenes and [n]polynorbornanes as molecular scaffolds for anion recognition. Ph.D. Thesis (May 2010). (361 pages).

Lundin, et al, "Hierarchical molecular tagging to resolve long continuous sequences by massively parallel sequencing", Sci Rep., 3:1186, 2003.

Lupski. Genomic rearrangements and sporadic disease. Nat Genet. Jul. 2007;39(7 Suppl):S43-7.

Macaulay; et al., "G&T-seq: parallel sequencing of single-cell genomes and transcriptomes. Nature Methods, 2015, p. 1-7."

Macaulay, et al. Single-Cell Multiomics: Multiple Measurements from Single Cells. Trends in Genetics 33.2 (2017): 155-168. PMC. Web. Dec. 18, 2017.

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

(56) References Cited

OTHER PUBLICATIONS

Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Man. Monolithic Structures for Integrated Microfluidic Analysis. PhD Thesis. 2001.
Marcus. Gene method offers diagnostic hope. The Wall Street Journal. Jul. 11, 2012.
Maricic T, et al. Optimization of 454 sequencing library preparation from small amounts of DNA permits sequence determination of both DNA strands. Biotechniques. Jan. 2009; 46(1):51-2, 54-7.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Merriman, et al. Progress in ion torrent semiconductor chip based sequencing. Electrophoresis. Dec. 2012;33(23):3397-417. doi: 10.1002/elps.201200424.
Microfluidic ChipShop. Microfluidic product catalogue. Mar. 2005.
Microfluidic ChipShop. Microfluidic product catalogue. Oct. 2009.
Miller JC, et al. An improved zinc-finger nuclease architecture for highly specific genome editing. Nat. Biotechnol. 2007;25:778-785.
miRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.A.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production of Monodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics. ,13:1, 2012.
Pantel, et al. Detection methods of circulating tumor cells. J Thorac Dis. Oct. 2012;4(5):446-7. doi: 10.3978/j.issn.2072-1439.2012.08.15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, et al. Accurate whole-genome sequencing and haplotyping from 10 to 20 human cells. Nature. Jul. 11, 2012;487(7406):190-5. doi: 10.1038/Nature11236.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran et al. Genome engineering using the CRISPR-Cas9 system. Nature Protocols 8:2281-2308 (2013). 0.
Reis, A. et al. "CRISPR/Cas9 and Targeted Genome Editing: A New Era in Molecular Biology" (2014) XP002766825: URL:https://ww.

(56) References Cited

OTHER PUBLICATIONS neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005UsingMultiplexIdentifierAdaptorsForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sakaguchi, et al. (1996) Cautionary Note on the Use of dUMP-Containing PCR Primers with Pfu and VentR. Biotechniques, 21(3): 369-370 (Year: 1996).
Sander JD, et al. Selection-free zinc-finger-nuclease engineering by context-dependent assembly (CoDA). Nat. Methods. 2011;8:67-69.
Schirinzi et al., Combinatorial sequencing-by-hybridization: Analysis of the NF1 gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com. pp. 1/3-3/3, Nov. 1999.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Skerra A. Phosphorothioate primers improve the amplification of DNA sequences by DNA polymerases with proofreading activity. Nucleic Acids Res. Jul. 25, 1992; 20(14):3551-4.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Spormann Laboratory, Polymerase Chain Reaction (PCR), Alfred Spormann Laboratory, 2009, 1-3. (Year: 2009).
Stoeckius, et al. Large-scale simultaneous measurement of epitopes and transcriptomes in single cells. bioRxiv 113068; doi: https://doi.org/10.1101/113068, 2017.
Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tawfik, D.S., et al., "Man-made cell-like compartments for molecular evolution," Nature Biotechnology, vol. 16, pp. 652-656 (1998).
Tayyab, S. et al. "Size exclusion chromatography and size exclusion HPLC of proteins" Biochem Ed, Pergamon, (1991) 19(3):149-152.
Tewhey, et al. Microdroplet-based PCR amplification for large-scale targeted sequencing. Nat Biotechnol. Nov. 2006;27(11):1025-31. doi: 10.1038/nbt.1583. Epub Nov. 1, 2009.
Tewhey et al., Supplementary Materials, Nature Biotechnology, 2009, 27(11), 1-22.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
ThermoFisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.

(56) References Cited

OTHER PUBLICATIONS

Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/Ieu.2011.32. Epub Mar. 18, 2011.
Whitesides, "Soft lithography in biology and biochemistry", Annual Review of Biomedical Engineering, 3:335-373 (2001).
Williams et al., Amplification of complex gene libraries by emulsion PCR, Nature Methods 3(7):545-550 (2006).
Wiseman, R.W. et al. "Major histocompatibility complex genotyping with massively parallel pyrosequencing" Nature Medicine (Oct. 11, 2009) 15(11):1322-1326.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone. 0181163. eCollection 2017.
Xia and Whitesides, Soft Lithography, Ann. Rev. Mat. Sci. 28:153-184 (1998).
Xiao, et al, "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online]. University of Washington. 2015 [Retrieved on May 3, 2017].
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu et al. Hydrogel Droplet Microfluidics for High-Throughput Single Molecule/Cell Analysis. Accounts of Chemical Research Article ASAP. DOI: 10.1021/acs.accounts.6b00370. vol. 50, No. 1, pp. 22-31, Dec. 2016.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypoosmolar electrofusion. Hum• Antibodies Hybridomas. Jan. 1992;3(1): 14-8.
Zong, et al. Genome-wide detection of single-nucleotide and copy-number variations of a single human cell. Science. Dec. 21, 2012;338(6114):1622-6. doi: 10.1126/science.1229164.
Anonymous: "TCEP=HCl" Thermo Scientific, Dec. 31, 2013 (Dec. 31, 2013), XP055508461, Retrieved from the Internet: URL:https://assets.thermofishercom/TFS-Assets/LSG/manuals/MAN0011306_TCEP_HCl_UG.pdf.
Co-pending U.S. Appl. No. 16/144,832, filed Sep. 27, 2018.
Lebedev, A. et al. "Hot Start PCR with heat-activatable primers: a novel approach for improved PCR performance" NAR (2008) 36(20):E131-1.
Zhang, et al. One-step fabrication of supramolecular microcapsules from microfluidic droplets. Science. Feb. 10, 2012;335(6069):690-4. doi: 10.1126/science.1215416.
Adey, et al., "Ultra-low-input, tagmentation-based whole-genome bisulfite sequencing", Genome Research, 2012, 22 ;6): 1139-1143.
Ason et al. DNA sequence bias during Tn5 transposition. Journal of molecular biology 335.5 (2004): 1213-1225.
Bjornsson et al., Intra-individual change over time in DNA methylation with familial clustering, JAMA, Jun. 25, 2008, vol. 299 No. 24, pp. 2877-2883.
Boyle, et al. "High-resolution genome-wide in vivo footprinting of diverse transcription factors in human cells", Genome Res. Mar. 2011;21(3):456-64.
Buenrostro, et al., "Tranposition of native chromatin for fast and sensitive epigenomic profiling of open chromatin, DNA-binding proteins and nucleosome position", Nature Methods, 2013, 10(12): 1213-1218.

(56) References Cited

OTHER PUBLICATIONS

Caruccio, et al. Nextera Technology for NGS DNA Library Preparation: Simultaneous Fragmentation and Tagging by in Vitro Transposition, Nextera Technology, 2009, 16-3, 1-3. (Year: 2009).
Co-pending U.S. Appl. No. 16/000,803, filed Jun. 5, 2018.
Co-pending U.S. Appl. No. 16/045,474, filed Jul. 25, 2018.
Co-pending U.S. Appl. No. 16/052,431, filed Aug. 1, 2018.
Co-pending U.S. Appl. No. 16/052,486, filed Aug. 1, 2018.
Co-pending U.S. Appl. No. 16/056,231, filed Aug. 6, 2018.
Co-pending U.S. Appl. No. 16/138,448, filed Sep. 21, 2018.
Depristo et al. A framework for variation discovery and genotyping using next-generation DNA sequencing data. Nature Genet 43:491-498 (2011).
Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Haring, et al. Chromatin immunoprecipitation: optimization, quantitative analysis and data normalization. Plant Methods. 2007; 3: 11.
Hu et al., Shape Controllable Microgel Particles Prepared by Microfluidic Combining External Crosslinking, Biomicrofluidics 6:26502 (May 18, 2012).
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
Knapp, et al. Generating barcoded libraries for multiplex high-throughput sequencing. Methods Mol Biol. 2012;840:155-70. doi: 10.1007/978-1-61779-516-9_19.
McGinnis, et al. Multi-seq: Scalable sample multiplexing for single-cell RNA sequencing using lipid-tagged indices. bioRxiv 387241; doi: https://doi.org/10.1101/387241, Aug. 2018.
Park. ChIP-seq: advantages and challenges of a maturing technology. Nature Reviews Genetics vol. 10, pp. 669-680 (2009).
U.S. Appl. No. 61/982,001, filed Apr. 21, 2014 (Year:2014).
Savva, et al. The structural basis of specific base-excision repair by uracil-DNA glycosylase. Nature. Feb. 9, 1995;373(6514):487-93.
Simon, et al., "Using formaldehyde-assisted isolation of regulatory elements (FAIRE) to isolate active regulatory DNA", Nature Protocols, 2012, 7(2): 256-267.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Zentner, et al. Surveying the epigenomic landscape, one base at a time. Genome Biol. Oct. 22, 2012;13(10):250. doi: 10.1186/gb4051.
Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.
Co-pending U.S. Appl. No. 16/033,065, filed Jul. 11, 2018.
Co-pending U.S. Appl. No. 16/043,874, filed Jul. 24, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/160,576, filed Oct. 15, 2018.
Co-pending U.S. Appl. No. 16/160,719, filed Oct. 15, 2018.
Co-pending U.S. Appl. No. 16/165,389, filed Oct. 19, 2018.
Co-pending U.S. Appl. No. 16/170,980, filed Oct. 25, 2018.
Co-pending U.S. Appl. No. 16/206,168, filed Nov. 30, 2018.
Co-pending U.S. Appl. No. 16/212,441, filed Dec. 6, 2018.
Delehanty, et al. Peptides for specific intracellular delivery and targeting of nanoparticles: implications for developing nanoparticle-mediated drug delivery. Ther Deliv. Sep. 2010;1(3):411-33.
Epicentre., "EZ-Tn5TM Custom Transposome Construction Kits", http://www.epicentre.com, pp. 1-17, 2012.
"How many species of bacteria are there" (wisegeek.com; accessed Jan. 21, 2014). pp. 1/7-2/7.
"List of sequenced bacterial genomes" (Wikipedia.com; accessed Jan. 24, 2014), pp. 1-57.
Margulies 2005 Supplementary methods (Year: 2005), pp. 1-34.
Margulies et al. "Genome sequencing in microfabricated high-density picoliter reactors", Nature (2005) 437:376-380.
"Meyer, et al., From micrograms to picograms: quantitative PCR reduces the material demands of high-throughput sequencing, Nucleic Acids Research, 2008, vol. 36, No. 1, 6 pages".
Thaxton, C.S. et al. "A Bio-Bar-Code Assay Based Upon Dithiothreitol Oligonucleotide Release" Anal Chem (2005) 77:8174-8178.
Ullal et al. Cancer Cell Profiling by Barcoding Allows Multiplexed Protein Analysis in Fine-Needle Aspirates. Sci Transl Med. Jan. 15, 2014; 6(219): 219ra9.
Zhang, et al. Reconstruction of DNA sequencing by hybridization. Bioinformatics. Jan. 2003;19(1):14-21.
Co-pending U.S. Appl. No. 16/196,684, filed Nov. 20, 2018.
Jin, et al. Genome-wide detection of DNase I hypersensitive sites in single cells and FFPE tissue samples. Nature. Dec. 3, 2015;528(7580):142-6. doi: 10.1038/nature15740.
AH006633.3 (*Homo sapiens* clone P1 and PAC max interactor 1 (MXI1) gene, complete cds, NCBI Reference Sequence, priority to Jun. 10, 2016, 5 pages) (Year:2016).
Ahern, H. The Scientist, vol. 20, pp. 20 and 22. Jul. 1995.
Ailenberg, et al. (2000) Controlled Hot Start and Improved Specificity in Carrying Out PCR Utilizing Touch-Up and Loop Incorporated Primers (TULIPS). BioTechniques, 29:1018-1024. (Year: 2000).
Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Epicenter, EZ-Tn5 Transposase, Epicenter, 2012, 1-5. (Year: 2012).
Mali, et al. Barcoding cells using cell-surface programmable DNA-binding domains. Nat Methods. May 2013;10(5):403-6. doi: 10.1038/nmeth.2407. Epub Mar. 17, 2013.
Pfeifer, et al. Bivalent cholesterol-based coupling of oligonucleotides to lipid membrane assemblies. J Am Chem Soc. Aug. 25, 2004;126(33):10224-5.
Bentolila, et al. Single-step multicolor fluorescence in situ hybridization using semiconductor quantum dot-DNA conjugates. Cell Biochem Biophys. 2006;45(1):59-70.
Bystrykh, et al. Generalized DNA barcode design based on Hamming codes. PLoS One. 2012;7(5):e36852. doi: 10.1371/journal.pone.0036852. Epub May 17, 2012.
Co-pending U.S. Appl. No. 16/395,090, filed Apr. 25, 2019.
Definition of "corresponding", Merriam-Webster Online, downloaded from http://www.merriam-webster.com/dictionary/corresponding (Year: 2019).
Co-pending U.S. Appl. No. 16/419,428, filed May 22, 2019.
Co-pending U.S. Appl. No. 16/419,461, filed May 22, 2019.
Co-pending U.S. Appl. No. 16/419,555, filed May 22, 2019.
Co-pending U.S. Appl. No. 16/419,630, filed May 22, 2019.
Co-pending U.S. Appl. No. 16/419,820, filed May 22, 2019.
Co-pending U.S. Appl. No. 16/435,362, filed Jun. 7, 2019.
Co-pending U.S. Appl. No. 16/435,417, filed Jun. 7, 2019.
Dhingra, et al. A complete solution for high throughput single cell targeted multiomic DNA and RNA sequencing for cancer research. Poster. AACR 2019.

* cited by examiner

METHODS AND SYSTEMS FOR DROPLET-BASED SINGLE CELL BARCODING

CROSS-REFERENCE

This application is a continuation of PCT Application No. PCT/US2018/16019, filed Jan. 30, 2018, which claims priority to U.S. Provisional Patent Application No. 62/452,261, filed Jan. 30, 2017, U.S. Provisional Patent Application No. 62/500,943, filed May 3, 2017, and U.S. Provisional Patent Application No. 62/570,783, filed Oct. 11, 2017, each of which are entirely incorporated herein by reference for all purposes.

BACKGROUND

Whole genome amplification and sequencing technologies are beginning to find broader adoption. These technologies may not consider the heterogeneity of a sample; instead, they may assume that all species to be amplified or sequenced come from a homogeneous population of cells or other biological materials (such as viruses). However, certain applications may benefit from the amplification or sequencing of species obtained from single cells obtained from a much larger population. In some cases, the single cells of interest may be quite rare. For instance, cancerous cells may undergo continuous mutations in their deoxyribonucleic acid (DNA) sequences. Cancer researchers or oncologists may wish to amplify and sequence the genomes of such cells or of other individual cells. They may find, however, that sequencing data attributable to the single cells of interest is obscured by that arising from far more prevalent cells. Thus, there is a need for sample preparation techniques that allow partial or whole genome amplification and sequencing of single cells of interest.

SUMMARY

Provided herein are methods and systems for sample preparation techniques that allow amplification (e.g., whole genome amplification, reverse transcription, amplification of cellular nucleic acids, etc.) and sequencing of single cells, which may be of interest. The methods and systems generally operate by bringing together a first liquid phase comprising a plurality of biological particles (e.g., particles comprising a cell or a cell component(s)), a second liquid phase comprising gel beads, and a third immiscible phase. The liquid phases may interact to form partitions (e.g., droplets). Some of the partitions may contain a single biological particle or a plurality of biological particles and one or more gel beads. The methods and systems may be configured to allow the implementation of a single operation or multi-operation chemical and/or biochemical processing within the partitions.

Methods and systems of the present disclosure may allow particular biochemical operations to occur in a droplet prior to allowing other biochemical operations to occur in the droplet. The droplet may contain a gel bead which may contain a tag (such as a barcode) that may be used to barcode macromolecular constituents (e.g., nucleic acid molecules) of a single biological particle.

Methods and systems of the present disclosure may be used to generate target sequence or sequencing reads ("reads") specific to macromolecular constituents of interest at a higher rate than non-target specific reads. For instance, the methods and systems are characterized by their suppression of no template control (NTC) effects.

In an aspect, the present disclosure provides a method for analysis of a single biological particle, comprising (a) providing a first liquid phase comprising a plurality of biological particles; (b) providing a second liquid phase comprising a plurality of beads each including a tag to barcode one or more macromolecular constituents of each of the plurality of biological particles; (c) bringing the plurality of biological particles from the first liquid phase and the plurality of beads from the second liquid phase in contact with a third liquid phase that is immiscible with the first or second liquid phase, to partition each of the plurality of biological particles and the plurality of beads into a plurality of partitions (e.g., droplets), wherein upon partitioning, a given partition of the plurality of partitions includes a single biological particle from the plurality of biological particles and a single bead from the plurality of beads; (d) in the given partition (e.g., droplet), using the tag from the single bead to barcode the one or more macromolecular constituents of the single biological particle, forming one or more barcoded macromolecules; and (e) subjecting the barcoded macromolecules to sequencing to generate reads characterized by a specific target read(s) to non-target specific read(s) ratio greater than 1, which specific target read(s) of the reads is indicative of the one or more macromolecular constituents.

In some embodiments, the sequencing is nucleic acid sequencing. In some embodiments, the nucleic acid sequencing is massively parallel sequencing. In some embodiments, the nucleic acid sequencing is digital polymerase chain reaction (PCR).

In some embodiments, the specific target read(s) to non-target specific read(s) ratio is greater than 100. In some embodiments, the specific target read(s) to non-target specific read(s) ratio is greater than 1,000. In some embodiments, the specific target read(s) to non-target specific read(s) ratio is greater than 10,000. In some embodiments, the specific target read(s) to non-target specific read(s) ratio is greater than 100,000. In some embodiments, the specific target read(s) to non-target specific read(s) ratio is greater than 1,000,000. In some embodiments, the specific target read(s) to non-target specific read(s) ratio is greater than 10,000,000. In some embodiments, the specific target read(s) to non-target specific read(s) ratio is greater than 100,000,000. In some embodiments, the specific target read(s) to non-target specific read(s) ratio is greater than 1,000,000,000.

In some embodiments, the specific target read(s) correspond to one or more nucleic acid sequences from the single biological particle. In some embodiments, the non-target specific read(s) corresponds to one or more exogenous nucleic acid sequences.

In some embodiments, the plurality of partitions is a plurality of droplets. In some embodiments, the plurality of partitions is a plurality of wells.

In some embodiments, a given bead of the plurality of beads includes one or more tags coupled to a surface thereof and/or enclosed within the given bead.

In some embodiments, the plurality of partitions is part of a population of partitions that includes one or more partitions that are unoccupied by biological particles and/or beads.

In another aspect, the present disclosure provides a method for analysis of a single biological particle, comprising (a) providing a first liquid phase comprising a plurality of biological particles; (b) providing a second liquid phase comprising a plurality of beads each including a tag to barcode one or more macromolecular constituents of each of the plurality of biological particles; and (c) bringing the plurality of biological particles from the first liquid phase and the plurality of beads from the second liquid phase in contact with a third liquid phase that is immiscible with the first or second liquid phase, to partition each of the plurality of biological particles and the plurality of beads into a plurality of partitions, wherein upon partitioning, a given partition of the plurality of partitions includes a single biological particle from the plurality of biological particles and a single bead from the plurality of beads, wherein the single biological particle includes or is enclosed within a polymer or gel matrix.

In some embodiments, the first liquid phase further comprises precursors that are capable of being polymerized or gelled. In some embodiments, the method comprises subjecting the first liquid phase to conditions sufficient to polymerize or gel the precursors so as to encapsulate the single biological particle in the polymer or gel matrix. In some embodiments, the polymer or gel matrix is diffusively permeable to reagents while retaining the one or more macromolecular constituents.

In some embodiments, the method comprises subjecting the single biological particle to conditions sufficient to lyse the single biological particle to provide a lysed single biological particle. In some embodiments, the method comprises subjecting the lysed single biological particle to conditions sufficient to denature the one or more macromolecular constituents released from the lysed single biological particle. In some embodiments, the method comprises subjecting the lysed single biological particle to conditions sufficient to release the one or more macromolecular constituents from the polymer or gel matrix.

In some embodiments, the method comprises using the tag from the single bead to barcode the one or more macromolecular constituents, forming one or more barcoded macromolecules. In some embodiments, the method comprises subjecting the barcoded macromolecules to sequencing.

In some embodiments, the polymer or gel matrix includes one or more of disulfide crosslinked polyacrylamide, agarose, alginate, polyvinyl alcohol, PEG-diacrylate, PEG-acrylate/thiol, PEG-azide/alkyne, other acrylates, chitosan, hyaluronic acid, collagen, fibrin, gelatin, and elastin.

In some embodiments, the conditions sufficient to lyse the single biological particle comprises exposure to sodium hydroxide (NaOH). In some embodiments, the conditions sufficient to denature the one or more macromolecular constituents comprises exposure to sodium hydroxide (NaOH). In some embodiments, the conditions sufficient to release the one or more macromolecular constituents comprises exposure to dithiothreitol (DTT). In some embodiments, the one or more macromolecular constituents released from the lysed single biological particle are denatured prior to (c).

In some embodiments, the sequencing is nucleic acid sequencing. In some embodiments, the nucleic acid sequencing is massively parallel sequencing. In some embodiments, the nucleic acid sequencing is digital polymerase chain reaction (PCR).

In some embodiments, the third liquid phase includes an oil. In some embodiments, the oil includes a fluorinated hydrocarbon. In some embodiments, the first liquid phase and the second liquid phase are the same phase.

In some embodiments, the first liquid phase and the second liquid phase are mixed to provide a mixed phase, and the mixed phase is brought in contact with the oil phase.

In some embodiments, the single biological particle comprises an organelle. In some embodiments, the single biological particle comprises a virus. In some embodiments, the single biological particle comprises a cell. In some embodiments, the cell comprises a rare cell from a population of cells.

In some embodiments, the rare cell is present in a sample at a concentration of at least about 1 in $10^2$ cells of the population of cells. In some embodiments, the rare cell is present in a sample at a concentration of at least about 1 in $10^3$ cells of the population of cells. In some embodiments, the rare cell is present in a sample at a concentration of at least about 1 in $10^4$ cells of the population of cells. In some embodiments, the rare cell is present in a sample at a concentration of at least about 1 in $10^5$ cells of the population of cells. In some embodiments, the rare cell is present in a sample at a concentration of at least about 1 in $10^6$ cells of the population of cells. In some embodiments, the rare cell is present in a sample at a concentration of at least about 1 in $10^7$ cells of the population of cells. In some embodiments, the rare cell is present in a sample at a concentration of at least about 1 in $10^8$ cells of the population of cells. In some embodiments, the rare cell is present in a sample at a concentration of at least about 1 in $10^9$ cells of the population of cells. In some embodiments, the rare cell is present in a sample at a concentration of at least about 1 in $10^{10}$ cells of the population of cells. In some embodiments, the rare cell is present in a sample at a concentration of at least about 1 in $10^{11}$ cells of the population of cells. In some embodiments, the rare cell is present in a sample at a concentration of at least about 1 in $10^{12}$ cells of the population of cells. In some embodiments, the rare cell is present in a sample at a concentration of at least about 1 in $10^{13}$ cells of the population of cells. In some embodiments, the rare cell is present in a sample at a concentration of at least about 1 in $10^{14}$ cells of the population of cells. In some embodiments, the rare cell is present in a sample at a concentration of at least about 1 in $10^{15}$ cells of the population of cells.

In some embodiments, the rare cell is a cancerous cell. In some embodiments, the cancer cell is a circulating tumor cell. In some embodiments, the rare cell is a cell obtained from an in vitro fertilization procedure. In some embodiments, the rare cell is a cell obtained from an individual displaying genetic mosaicism. In some embodiments, the rare cell is a cell obtained from an organism produced using synthetic biology techniques. In some embodiments, the population of cells is a heterogeneous population of cells.

In some embodiments, the method comprises obtaining the plurality of biological particles. In some embodiments, the plurality of biological particles is obtained from a blood of a subject. In some embodiments, the plurality of biological particles includes cells. In some embodiments, the cells are cancerous cells. In some embodiments, the plurality of biological particles is obtained from a tissue of a subject.

In some embodiments, the one or more macromolecular constituents comprise deoxyribonucleic acid (DNA). In some embodiments, the one or more macromolecular constituents comprise ribonucleic acid (RNA). In some embodiments, the one or more macromolecular constituents comprise peptides or proteins.

In some embodiments, the tag is a primer. In some embodiments, (d) further comprises subjecting single biological particle to conditions sufficient for nucleic acid amplification. In some embodiments, the conditions sufficient for nucleic acid amplification comprise priming free amplification. In some embodiments, the priming free amplification comprises priming free amplification by polymerization at nick sites.

In some embodiments, the method further comprises using the tag to identify the one or more macromolecular constituents of the single biological particle from the plurality of biological particles. In some embodiments, the method further comprises subjecting the barcoded macromolecules to nucleic acid sequencing to identify the one or more macromolecular constituents. In some embodiments, the nucleic acid sequencing is untargeted sequencing. In some embodiments, the nucleic acid sequencing is targeted sequencing.

In some embodiments, the plurality of partitions is a plurality of droplets. In some embodiments, the plurality of partitions is a plurality of wells.

In some embodiments, a given bead of the plurality of beads includes one or more tags coupled to a surface thereof and/or enclosed within the given bead.

In some embodiments, the plurality of partitions is part of a population of partitions that includes one or more partitions that are unoccupied by biological particles and/or beads.

In another aspect, the present disclosure provides a method for analysis of a single biological particle, comprising (a) providing a plurality of biological particles, and a plurality of beads each including a tag to barcode one or more macromolecular constituents of each of the plurality of biological particles; and (b) partitioning the plurality of biological particles and the plurality of beads into a plurality of partitions, wherein upon partitioning, a given partition of the plurality of partitions includes a single biological particle from the plurality of biological particles and a single bead from the plurality of beads, wherein the single biological particle includes or is enclosed within a gel or polymer matrix within the given partition.

In some embodiments, the plurality of partitions is a plurality of droplets. In some embodiments, the plurality of partitions is a plurality of wells.

In some embodiments, a given bead of the plurality of beads includes one or more tags coupled to a surface thereof and/or enclosed within the given bead.

In some embodiments, the plurality of partitions is part of a population of partitions that includes one or more partitions that are unoccupied by biological particles and/or beads.

In another aspect, the present disclosure provides a system for analysis of a single biological particle, comprising a partition generator comprising (i) a first source of a first liquid phase comprising a plurality of biological particles, (ii) a second source of a second liquid phase comprising a plurality of beads each including a tag to barcode one or more macromolecular constituents of each of the plurality of biological particles, and (iii) a third source of a third liquid phase that is immiscible with the first or second liquid phase; and a controller operatively coupled to the partition generator, wherein the controller is programmed to (i) bring the first liquid phase from the first source and the second liquid phase from the second source in contact with the third liquid phase from the third source along a first channel to partition each of the plurality of biological particles and the plurality of beads into a plurality of partitions that flow along a second channel, wherein upon partitioning, a given partition of the plurality of partitions includes a single biological particle from the plurality of biological particles and a single bead from the plurality of beads; and (ii) in the given partition, use the tag from the single bead to barcode the one or more macromolecular constituents of the single biological particle, forming one or more barcoded macromolecules; and (iii) subject the barcoded macromolecules to sequencing to generate reads characterized by a specific target read(s) to non-target specific read(s) ratio greater than 1, which specific target read(s) of the reads is indicative of the one or more macromolecular constituents.

In another aspect, the present disclosure provides a system for analysis of a single biological particle, comprising a partition generator comprising (i) a first source of a first liquid phase comprising a plurality of biological particles, (ii) a second source of a second liquid phase comprising a plurality of beads each including a tag to barcode one or more macromolecular constituents of each of the plurality of biological particles, and (iii) a third source of a third liquid phase that is immiscible with the first or second liquid phase, wherein the first liquid phase further comprises precursors that are capable of being polymerized or gelled; and a controller operatively coupled to the partition generator, wherein the controller is programmed to bring the plurality of biological particles from the first liquid phase and the plurality of beads from the second liquid phase in contact with the third liquid phase that is immiscible with the first or second liquid phase, to partition each of the plurality of biological particles and the plurality of beads into a plurality of partitions, wherein upon partitioning, a given partition of the plurality of partitions includes a single biological particle from the plurality of biological particles and a single bead from the plurality of beads, wherein the single biological particle includes or is enclosed within a polymer or gel matrix.

In some embodiments, the third liquid phase includes an oil. In some embodiments, the first liquid phase and the second liquid phase are the same phase.

In some embodiments, the plurality of biological particles includes cells. In some embodiments, the plurality of biological particles is obtained from a tissue of a subject.

In some embodiments, the one or more macromolecular constituents comprise deoxyribonucleic acid (DNA). In some embodiments, the one or more macromolecular constituents comprise ribonucleic acid (RNA). In some embodiments, the tag is a primer.

In some embodiments, the controller subjects the single biological particle to conditions sufficient for nucleic acid amplification. In some embodiments, the controller is programmed to subject the single biological particle to conditions sufficient to barcode at least one macromolecular constituent from the single biological particle with at least one tag from the single bead.

In another aspect, the present disclosure provides a non-transitory computer-readable medium comprising machine-executable code that, upon execution by one or more computer processors, implements a method for analysis of a single biological particle, the method comprising (a) providing a first liquid phase comprising a plurality of biological particles; (b) providing a second liquid phase comprising a plurality of beads each including a tag to barcode one or more macromolecular constituents of each of the plurality of biological particles; (c) bringing the plurality of biological particles from the first liquid phase and the plurality of beads from the second liquid phase in contact with a third liquid phase that is immiscible with the first or second liquid phase, to partition each of the plurality of biological particles and the plurality of beads into a plurality of partitions, wherein upon partitioning, a given partition of the plurality of partitions includes a single biological particle from the plurality of biological particles and a single bead from the plurality of beads, wherein the single biological particle includes or is enclosed within a polymer or gel matrix.

In another aspect, the present disclosure provides a method for cellular analysis, comprising
(a) partitioning a plurality of cells or derivatives thereof into a plurality of partitions, wherein upon partitioning, a given partition of the plurality of partitions includes a single cell or derivative thereof from the plurality of cells or derivatives thereof and a set of tags that are capable of barcoding one or more macromolecular constituents of the single cell or derivative thereof, wherein the single cell or derivative thereof includes or is enclosed within a gel or polymer matrix within the given partition;
(b) using the set of tags to barcode the one or more macromolecular constituents from the single cell, thereby providing one or more barcoded macromolecules; and (c) analyzing the one or more barcoded macromolecules or derivatives thereof.

In some embodiments, the one or more macromolecular constituents include deoxyribonucleic acid. In some embodiments, the one or more macromolecular constituents include ribonucleic acid.

In some embodiments, the plurality of partitions are a plurality of droplets. In some embodiments, the plurality of partitions are a plurality of wells. In some embodiments, the set of tags is coupled to a bead in the given partition.

In some embodiments, the method further comprises releasing the one or more barcoded macromolecules or derivatives thereof from the given partition prior to analyzing.

In some embodiments, the method further comprises processing the single cell to include or be enclosed within the gel or polymer matrix prior to partitioning the plurality of cells into the plurality of partitions. In some embodiments, the method further comprises processing the single cell to include or be enclosed within the gel or polymer matrix after partitioning the plurality of cells into the plurality of partitions. In some embodiments, the cells are live cells.

In some embodiments, the live cells are capable of being cultured. In some embodiments, the live cells are capable of being cultured upon enclosure in or when comprising a gel or polymer matrix.

Tags (e.g., barcodes) may be enclosed within the plurality of beads. As an alternative or in addition to, tags may be coupled to surfaces of the plurality of beads. A given bead may include a plurality of tags.

In another aspect, the disclosure provides a method for processing or analyzing one or more components from a cell, comprising: (a) providing a plurality of cell beads and a plurality of barcode beads, wherein (i) a cell bead of the plurality of cell beads comprises the one or more components of the cell, which one or more components comprise a nucleic acid molecule, and (ii) a barcode bead of the plurality of barcode beads comprises a plurality of nucleic acid barcode molecules for barcoding the nucleic acid molecule; and (b) partitioning the plurality of cell beads and the plurality of barcode beads into a plurality of partitions, wherein upon partitioning, a partition of the plurality of partitions comprises the cell bead and the barcode bead.

In some embodiments, the method further comprises performing one or more reactions on the nucleic acid molecule. In some embodiments, the one or more reactions comprise nucleic acid modification, nucleic acid amplification, nucleic acid insertion, nucleic acid cleavage, reverse transcription, or any combination thereof. In some embodiments, the nucleic acid modification comprises ligation, digestion, methylation, random mutagenesis, bisulfite conversion, uracil hydrolysis, nucleic acid repair, capping, decapping, or any combination thereof. In some embodiments, the nucleic acid amplification comprises isothermal amplification or polymerase chain reaction. In some embodiments, the nucleic acid insertion comprises transposon-mediated insertion, CRISPR/Cas9-mediated insertion, or any combination thereof. In some embodiments, the nucleic acid cleavage comprises transposon-mediated cleavage, CRISPR/Cas9-mediated cleavage, or any combination thereof. In some embodiments, the one or more reactions are performed in the partition. In some embodiments, the one or more reactions are performed outside the partition. In some embodiments, the one or more reactions are performed prior to (a). In some embodiments, the one or more reactions are performed subsequent to (a).

In some embodiments, the method further comprises using the plurality of nucleic acid barcode molecules to generate a barcoded nucleic acid molecule from the nucleic acid molecule. In some embodiments, generating the barcoded nucleic acid molecule comprises nucleic acid amplification. In some embodiments, generating the barcoded nucleic acid molecule comprises ligation. In some embodiments, the method further comprises releasing the barcoded nucleic acid molecule from the partition. In some embodiments, the method further comprises subjecting the barcoded nucleic acid molecule or derivative thereof to sequencing. In some embodiments, the method further comprises, prior to the sequencing, subjecting the barcoded nucleic acid molecule or derivative thereof to nucleic acid amplification. In some embodiments, the nucleic acid amplification is isothermal amplification or polymerase chain reaction. In some embodiments, the polymerase chain reaction is digital polymerase chain reaction.

In some embodiments, the cell bead comprises the cell, and the cell bead comprising the cell is subjected to conditions sufficient to lyse the cell to generate the one or more components. In some embodiments, the cell bead is subject to the conditions sufficient to lyse the cell in the partition. In some embodiments, the conditions sufficient to lyse the cell comprise exposing the cell beads to a lysis agent. In some embodiments, the conditions sufficient to lyse the cell comprise exposing the cell beads to sodium hydroxide, potassium hydroxide, sodium dodecyl sulfate, a non-ionic surfactant, a saponin, a proteinase, a lytic enzyme, freeze thawing, ultraviolet light, heat, or any combination thereof. In some embodiments, the non-ionic surfactant is 4-(1,1,3,3-Tetramethylbutyl)phenyl-polyethylene glycol (TRITON X-100).

In some embodiments, the cell bead includes or is enclosed within a gel or polymer matrix within the partition. In some embodiments, the barcode bead includes or is enclosed within a gel or polymer matrix within the partition. In some embodiments, the polymer or gel matrix includes one or more members selected from the group consisting of disulfide crosslinked polyacrylamide, agarose, alginate, polyvinyl alcohol, PEG-diacrylate, PEG-acrylate/thiol, PEG-azide/alkyne, other acrylates, chitosan, hyaluronic acid, collagen, fibrin, gelatin, and elastin.

In some embodiments, the plurality of partitions is a plurality of droplets. In some embodiments, the plurality of partitions is a plurality of wells. In some embodiments, one or more nucleic acid barcode molecules of the plurality of nucleic acid barcode molecules are coupled to a surface of the barcode bead and/or enclosed within the barcode bead.

In some embodiments, the cell bead further comprises additional reagents. In some embodiments, the partition further comprises additional reagents. In some embodiments, the additional reagents comprise primers, reverse transcriptase enzymes, polymerases, nucleotides, proteases, transposons, endonucleases, switch oligonucleotides, lysis reagents, or any combination thereof. In some embodiments, the nucleic acid molecule is a deoxyribonucleic acid molecule. In some embodiments, the deoxyribonucleic acid molecule is genomic deoxyribonucleic acid. In some embodiments, the deoxyribonucleic acid molecule is complementary deoxyribonucleic acid. In some embodiments, the nucleic acid molecule is a ribonucleic acid molecule. In some embodiments, the ribonucleic acid molecule is messenger ribonucleic acid. In some embodiments, the method further comprises recovering the nucleic acid molecule or a derivative thereof from the partition.

In some embodiments, the barcode bead is degradable upon application of a stimulus. In some embodiments, the method further comprises releasing the plurality of nucleic acid barcode molecules upon application of the stimulus. In some embodiments, the stimulus is a chemical stimulus, a biological stimulus, a temperature change, exposure to light, a pH change, or any combination thereof. In some embodiments, the chemical stimulus is a reducing agent. In some embodiments, the reducing agent is dithiothreitol, β-mercaptoethanol, (2S)-2-amino-1,4-dimercaptobutane, tris(2-carboxyethyl) phosphine, or any combination thereof. In some embodiments, the stimulus is a chemical or biological stimulus, and the partition comprises the stimulus. In some embodiments, the cell bead is degradable upon application of a stimulus. In some embodiments, the stimulus is a chemical stimulus, a biological stimulus, a temperature change, exposure to light, a pH change, or any combination thereof. In some embodiments, the chemical stimulus is a reducing agent. In some embodiments, the reducing agent is dithiothreitol, β-mercaptoethanol, (2S)-2-amino-1,4-dimercaptobutane, tris(2-carboxyethyl) phosphine, or any combination thereof. In some embodiments, the stimulus is a chemical or biological stimulus, and the partition comprises the stimulus.

In some embodiments, the plurality of partitions is part of a population of partitions that includes one or more partitions that are unoccupied by a cell bead and/or a barcode bead.

In another aspect, the disclosure provides a system for processing or analyzing one or more components from a cell, comprising: a first channel in fluid communication with a first source comprising a plurality of cell beads, wherein a cell bead of the plurality of cell beads comprises the one or more components of the cell, which one or more components comprise a nucleic acid molecule; a second channel in fluid communication with a second source comprising a plurality of barcode beads, wherein a barcode bead of the plurality of barcode beads comprises a plurality of nucleic acid barcode molecules for barcoding the nucleic acid molecule; and a junction that brings a first phase comprising the plurality of cell beads from the first channel and the plurality of barcode beads from the second channel in contact with a second phase that is immiscible with the first phase, to yield a plurality of droplets comprising the plurality of cell beads and the plurality of barcode beads, wherein a droplet of the plurality of droplets comprises the cell bead and the barcode bead.

In some embodiments, the first channel and the second channel are the same channel. In some embodiments, the system further comprises a third channel in fluid communication with a third source comprising additional reagents, wherein the first phase comprises the additional reagents. In some embodiments, the system further comprises a fourth channel in fluid communication with a fourth source comprising additional reagents, wherein the first phase comprises the additional reagents. In some embodiments, the additional reagents are reagents for nucleic acid amplification, reagents that can degrade or dissolve cell beads and/or barcode beads, reagents that degrade linkages between barcodes and barcode beads, or any combination thereof.

Another aspect of the disclosure provides a composition comprising a cell bead of a plurality of cell beads and a barcode bead of a plurality of barcode beads, wherein the cell bead comprises one or more components from a cell, which one or more components comprise a nucleic acid molecule, and wherein the barcode bead comprises a plurality of nucleic acid barcode molecules for barcoding the nucleic acid molecule. In some embodiments, the cell bead further comprises additional reagents. In some embodiments, the additional reagents comprise primers, reverse transcriptase enzymes, polymerases, nucleotides, proteases, transposons, endonucleases, switch oligonucleotides, or any combination thereof. In some embodiments, the nucleic acid molecule is a deoxyribonucleic acid molecule. In some embodiments, the deoxyribonucleic acid molecule is genomic deoxyribonucleic acid. In some embodiments, the deoxyribonucleic acid molecule is complementary deoxyribonucleic acid. In some embodiments, the nucleic acid molecule is a ribonucleic acid molecule. In some embodiments, the ribonucleic acid molecule is messenger ribonucleic acid.

In another aspect, the disclosure provides a method for generating a cell bead, comprising: (a) providing a plurality of cells and a plurality of polymeric or gel precursors; (b) partitioning the plurality of cells and the plurality of polymeric or gel precursors into a plurality of partitions, wherein upon partitioning, a partition of the plurality of partitions comprises a cell of the plurality of cells and at least a portion of the polymeric or gel precursors; and (c) subjecting the partitions to conditions suitable for cross-linking or polymerizing the polymeric or gel precursors to generate the cell bead, wherein the cell bead encapsulates the cell. In some embodiments, the method further comprises, subsequent to (b), subjecting the cell bead to conditions sufficient to lyse the cell. In some embodiments, the conditions sufficient to lyse the cell comprise exposing the cell beads to a lysis agent. In some embodiments, the conditions sufficient to lyse the cell comprise exposing the cell beads to sodium hydroxide, potassium hydroxide, sodium dodecyl sulfate, a non-ionic surfactant, a saponin, a proteinase, a lytic enzyme, freeze thawing, ultraviolet light, heat, or any combination thereof. In some embodiments, the non-ionic surfactant is 4-(1,1,3,3-Tetramethylbutyl)phenyl-polyethylene glycol (TRITON X-100). In some embodiments, in (b), the partition comprises a bead. In some embodiments, the bead is a magnetic bead. In some embodiments, the magnetic bead is a paramagnetic particle.

Another aspect of the present disclosure provides a method for processing one or more nucleic acid molecules from a cell, comprising (a) providing a plurality of cells and a plurality of polymeric or gel precursors; (b) partitioning the plurality of cells and the plurality of polymeric or gel precursors into a plurality of partitions, wherein upon partitioning, a partition of the plurality of partitions comprises (i) a nucleic acid molecule, (ii) a cell of the plurality of cells and (iii) at least a portion of the polymeric or gel precursors; (c) subjecting the plurality of partitions to conditions sufficient to cross-link or polymerize the polymeric or gel precursors to form a plurality of cell beads; and (d) partitioning the plurality of cell beads and a plurality of barcode beads comprising a plurality of nucleic acid barcode molecules into an additional plurality of partitions, wherein upon partitioning, a partition of the additional plurality of partitions comprises the cell bead and the barcode bead. In some embodiments, the method further comprises, subsequent to (a), subjecting the plurality of partitions to conditions sufficient to lyse the plurality of cells, releasing the nucleic acid molecule from the cell into the partition. In some embodiments, the nucleic acid molecule is a deoxyribonucleic acid molecule. In some embodiments, the nucleic acid molecule is a ribonucleic acid molecule. In some embodiments, in (b), the partition comprises a bead. In some embodiments, the bead is a magnetic bead. In some embodiments, the magnetic bead is a paramagnetic particle. In some embodiments, the method further comprises performing one or more reactions on the nucleic acid molecule. In some embodiments, the method further comprises barcoding the nucleic acid molecule to generate a barcoded nucleic acid molecule. In some embodiments, the method further comprises, subsequent to (d), releasing the barcoded nucleic acid molecule from the partition. In some embodiments, the method further comprises subjecting the barcoded nucleic acid molecule or derivative thereof to sequencing.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1A:
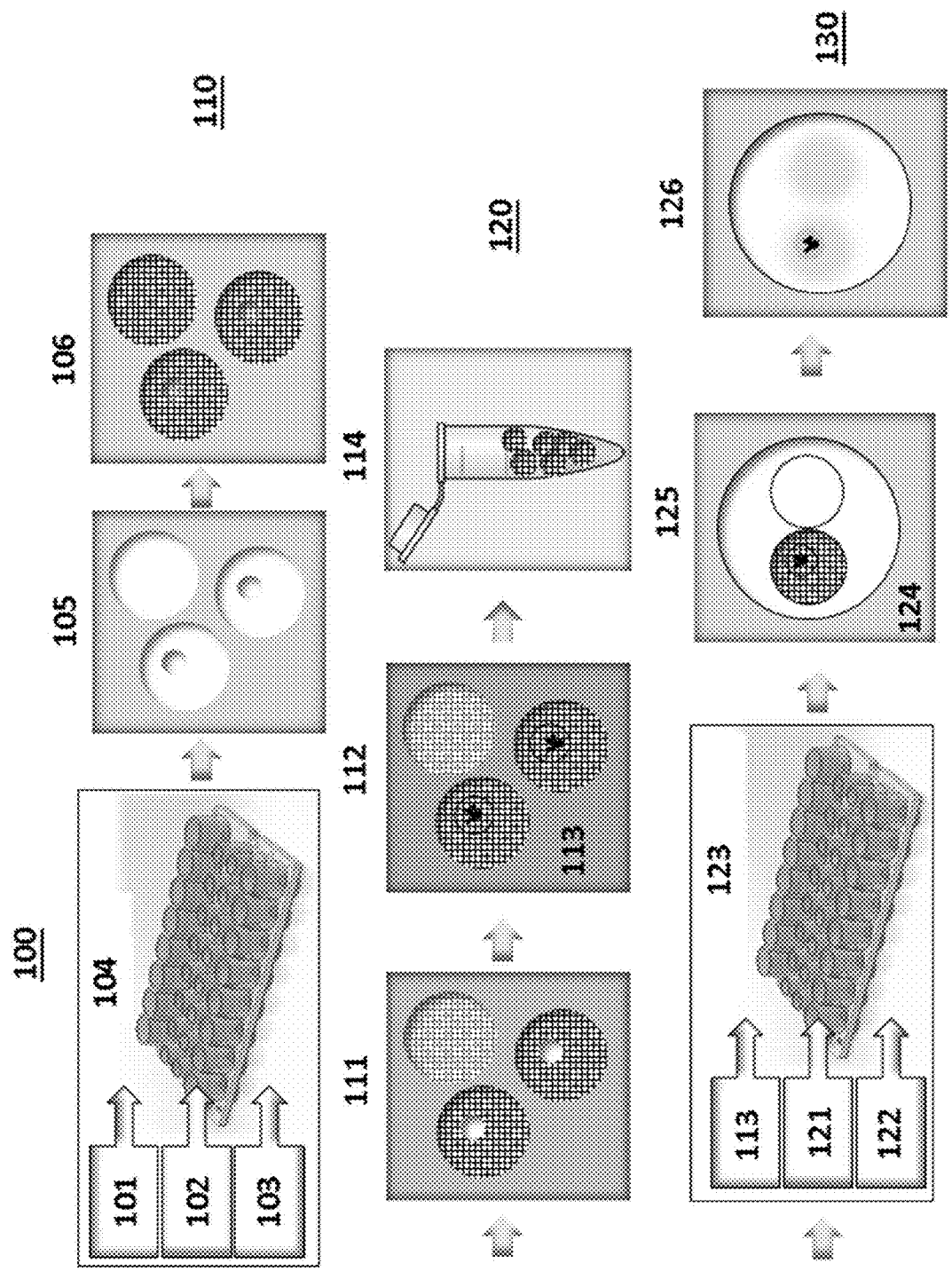
FIG. 1A schematically illustrates an example method for generating droplets comprising a barcoded bead and a cell bead (e.g., comprising a cell or a cell component(s))

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about the analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats, for example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "subject," as used herein, generally refers to an animal, such as a mammalian species (e.g., human) or avian (e.g., bird) species, or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, or an individual that is in need of therapy or suspected of needing therapy. A subject can be a patient.

The term "genome," as used herein, generally refers to an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach including ligation, hybridization, or other approaches.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, with limitation, a sequencing system by Illumina, Pacific Biosciences, Oxford Nanopore, or Life Technologies (Ion Torrent). Such devices may provide a plurality of raw genetic data corresponding to the genetic information of a subject (e.g., human), as generated by the device from a sample provided by the subject. In some situations, systems and methods provided herein may be used with proteomic information.

The term "variant," as used herein, generally refers to a genetic variant, such as a nucleic acid molecule comprising a polymorphism. A variant can be a structural variant or copy number variant, which can be genomic variants that are larger than single nucleotide variants or short indels. A variant can be an alteration or polymorphism in a nucleic acid sample or genome of a subject. Single nucleotide polymorphisms (SNPs) are a form of polymorphisms. Polymorphisms can include single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

The term "bead," as used herein, generally refers to a particle. The bead may be a solid or semi-solid particle. The bead may be a gel. The bead may be formed of a polymeric material. The bead may be magnetic or non-magnetic.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swap. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "cell bead," as used herein, generally refers to a particulate material that comprises (e.g., encapsulates, contains, etc.) a cell (e.g., a cell, a fixed cell, a cross-linked cell), a virus, components of, or macromolecular constituents derived from a cell or virus. For example, a cell bead may comprise a virus and/or a cell. In some cases, a cell bead comprises a single cell. In some cases, a cell bead may comprise multiple cells adhered together. A cell bead may include any type of cell, including without limitation prokaryotic cells, eukaryotic cells, bacterial, fungal, plant, mammalian, or other animal cell types, mycoplasmas, normal tissue cells, tumor cells, a T-cell (e.g., CD4 T-cell, CD4 T-cell that comprises a dormant copy of human immunodeficiency virus (HIV)), a fixed cell, a cross-linked cell, a rare cell from a population of cells, or any other cell type, whether derived from single cell or multicellular organisms. Furthermore, a cell bead may comprise a live cell, such as, for example, a cell may be capable of being cultured. Moreover, in some examples, a cell bead may comprise a derivative of a cell, such as one or more components of the cell (e.g., an organelle, a cell protein, a cellular nucleic acid, genomic nucleic acid, messenger ribonucleic acid, a ribosome, a cellular enzyme, etc.). In some examples, a cell bead may comprise material obtained from a biological tissue, such as, for example, obtained from a subject. In some cases, cells, viruses or macromolecular constituents thereof are encapsulated within a cell bead. Encapsulation can be within a polymer or gel matrix that forms a structural component of the cell bead. In some cases, a cell bead is generated by fixing a cell in a fixation medium or by cross-linking elements of the cell, such as the cell membrane, the cell cytoskeleton, etc. In some cases, beads may or may not be generated without encapsulation within a larger cell bead.

The term "rare cell," as used herein, generally refers to a cell which is present in a sample at a relatively low concentration. The rare cell may be a cancerous cell. The cancerous cell may be a circulating tumor cell. The rare cell may be obtained from an in vitro fertilization (IVF) procedure. The rare cell may be obtained from an individual displaying genetic mosaicism. The rare cell may be obtained from an organism produced using synthetic biology techniques. The rare cell may be present at a concentration of at most about 1 in $10^2$, 1 in $10^3$, 1 in $10^4$, 1 in $10^5$, 1 in $10^6$, 1 in $10^7$, 1 in $10^8$, 1 in $10^9$, 1 in $10^{10}$, 1 in $10^{11}$, 1 in $10^{12}$, 1 in $10^{13}$, 1 in $10^{14}$, or 1 in $10^{15}$ cells of the population of cells. The rare cell may be present at a concentration lying in a range defined by any two of the preceding values.

The term "macromolecular constituent," as used herein, generally refers to a macromolecule that is a component of or is derived from a biological material (e.g., a cell, a fixed cell, a cross-linked cell, a virus, etc.). The macromolecular constituent may comprise a nucleic acid. Such a macromolecule can be encapsulated within a cell bead. The macromolecular constituent may comprise a nucleic acid. The macromolecular constituent may comprise deoxyribonucleic acid (DNA) or a variant or derivative thereof. The macromolecular constituent may comprise ribonucleic acid (RNA) or a variant or derivative thereof. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein or a variant or derivative thereof. The macromolecular constituent may comprise a polynucleotide. The macromolecular constituent may comprise multiple polynucleotides. The macromolecular constituent may compromise chromatin or functional equivalents. The macromolecular constituent may comprise a peptide. The macromolecular constituent may comprise a polypeptide. The macromolecular constituent may comprise a polynucleotide/polypeptide complex.

The term "tag," as used herein, generally refers to a material capable of binding to a macromolecular constituent (e.g., DNA, RNA or protein). The tag may bind to the macromolecular constituent with high affinity. The tag may bind to the macromolecular constituent with high specificity. The tag may comprise a nucleotide sequence. The tag may comprise an oligonucleotide or polypeptide sequence. The tag may comprise a DNA aptamer. The tag may be or comprise a primer. The tag may be or comprise a protein. The tag may comprise a polypeptide. The tag may be or include a barcode, such as a barcode sequence. The tag may be a molecular species or atomic species (e.g., atomic particle, collection of atomic particles, or quantum dot).

The term "microfluidic device," as used herein generally refers to a device configured for fluid transport and having a fluidic channel through which fluid can flow with at least one dimension of no greater than about 10 millimeters (mm). The dimension can be any of length, width or height. In some cases, a microfluidic device comprises a fluidic channel having multiple dimensions of no greater than about 10 mm. A microfluidic device can also include a plurality of fluidic channels each having a dimension of no greater than about 10 mm. The dimension(s) of a given fluidic channel of a microfluidic device may vary depending, for example, on the particular configuration of the channel and/or channels and other features also included in the device.

In some examples, a dimension of a fluidic channel of a microfluidic device may be at most about 10 mm, at most about 9 mm, at most about 8 mm, at most about 7 mm, at most about 6 mm, at most about 5 mm, at most about 4 mm, at most about 3 mm, at most about 2 mm, at most about 1 mm, at most about 900 micrometers (μm), at most about 800 μm, at most 700 μm, at most about 600 μm, at most about 500 μm, at most about 400 μm, at most about 300 μm, at most about 200 μm, at most about 100 μm, at most about 90 μm, at most about 70 μm, at most about 60 μm, at most about 50 μm, at most about 40 μm, at most about 30 μm, at most about 20 μm, at most about 10 μm, at most about 8 μm, at most about 6 µm, at most about 4 µm, at most about 2 µm, at most about 1 µm or less. In some examples a dimension of a fluidic channel of a microfluidic device may be at least about 1 µm, at least about 2 µm, at least about 4 µm, at least about 6 µm, at least about 8 µm, at least about 10 µm, at least about 20 µm, at least about 30 µm, at least about 40 µm, at least about 50 µm, at least about 60 µm, at least about 70 µm, at least about 80 µm, at least about 90 µm, at least about 100 µm, at least about 200 µm, at least about 300 µm, at least about 400 µm, at least about 500 µm, at least about 600 µm, at least about 700 µm, at least about 800 µm, at least about 900 µm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm or more.

Microfluidic devices described herein can also include any additional components that can, for example, aid in regulating fluid flow, such as a fluid flow regulator (e.g., a pump, a source of pressure, etc.), features that aid in preventing clogging of fluidic channels (e.g., funnel features in channels; reservoirs positioned between channels, reservoirs that provide fluids to fluidic channels, etc.) and/or removing debris from fluid streams, such as, for example, filters. Additional microfluidic features are described in U.S. Patent Publication No. 2015/0292988, which is herein incorporated by reference in its entirety. Moreover, microfluidic devices may be configured as a fluidic chip that includes one or more reservoirs that supply fluids to an arrangement of microfluidic channels and also includes one or more reservoirs that receive fluids that have passed through the microfluidic device. In addition, microfluidic devices may be constructed of any suitable material(s), including polymer species and glass.

Nucleic acid sequencing technologies have yielded substantial results in sequencing biological materials, including providing substantial sequence information on individual organisms, and relatively pure biological samples. However, these systems have traditionally not been effective at being able to identify and characterize cells at the single cell level.

Many nucleic acid sequencing technologies derive the nucleic acids that they sequence from collections of cells obtained from tissue or other samples, such as biological fluids (e.g., blood, plasma, etc). The cells can be processed (e.g., all together) to extract the genetic material that represents an average of the population of cells, which can then be processed into sequencing ready DNA libraries that are configured for a given sequencing technology. Although often discussed in terms of DNA or nucleic acids, the nucleic acids derived from the cells may include DNA, or RNA, including, e.g., mRNA, total RNA, or the like, that may be processed to produce cDNA for sequencing. Following processing, absent a cell specific marker, attribution of genetic material as being contributed by a subset of cells or an individual cell may not be possible in such an ensemble approach.

In addition to the inability to attribute characteristics to particular subsets of cells or individual cells, such ensemble sample preparation methods can be, from the outset, predisposed to primarily identifying and characterizing the majority constituents in the sample of cells, and may not be designed to pick out the minority constituents, e.g., genetic material contributed by one cell, a few cells, or a small percentage of total cells in the sample. Likewise, where analyzing expression levels, e.g., of mRNA, an ensemble approach can be predisposed to presenting potentially inaccurate data from cell populations that are non-homogeneous in terms of expression levels. In some cases, where expression is high in a small minority of the cells in an analyzed population, and absent in the majority of the cells of the population, an ensemble method may indicate low level expression for the entire population.

These inaccuracies can be further magnified through processing operations used in generating the sequencing libraries from these samples. In particular, many next generation sequencing technologies (e.g., massively parallel sequencing) may rely upon the geometric amplification of nucleic acid fragments, such as via polymerase chain reaction, in order to produce sufficient DNA for the sequencing library. However, such amplification can be biased toward amplification of majority constituents in a sample, and may not preserve the starting ratios of such minority and majority components.

While some of these difficulties may be addressed by utilizing different sequencing systems, such as single molecule systems that do not require amplification, the single molecule systems, as well as the ensemble sequencing methods of other next generation sequencing systems, can also have large input DNA requirements. Some single molecule sequencing systems, for example, can have sample input DNA requirements of from 500 nanograms (ng) to upwards of 10 micrograms (µg), which may not be obtainable from individual cells or even small subpopulations of cells. Likewise, other NGS systems can be optimized for starting amounts of sample DNA in the sample of from approximately 50 ng to about 1 µg, for example.

Disclosed herein are methods and systems for characterizing macromolecular constituents from small populations of biological materials (e.g., cells or viruses), and in some cases, for characterizing macromolecular constituents from single cells. The methods described herein may compartmentalize the analysis of individual cells or small populations of cells, including e.g., nucleic acids from individual cells or small groups of cells, and then allow that analysis to be attributed back to the individual cell or small group of cells from which the nucleic acids were derived. This can be accomplished regardless of whether the cell population represents a 50/50 mix of cell types, a 90/10 mix of cell types, or virtually any ratio of cell types, as well as a complete heterogeneous mix of different cell types, or any mixture between these. Differing cell types may include cells from different tissue types of an individual or the same tissue type from different individuals, or biological organisms such as microorganisms from differing genera, species, strains, variants, or any combination of any or all of the foregoing. For example, differing cell types may include normal and tumor tissue from an individual, various cell types obtained from a human subject such as a variety of immune cells (e.g., B cells, T cells, and the like), multiple different bacterial species, strains and/or variants from environmental, forensic, microbiome or other samples, or any of a variety of other mixtures of cell types.

In an aspect, the methods and systems described herein, provide for the compartmentalization, depositing or partitioning of a cell or virus (e.g., a cell) or the macromolecular constituent(s) of the cell or virus from a sample into discrete compartments or partitions (referred to interchangeably herein as partitions), where each partition maintains separation of its own contents from the contents of other partitions. These partitions may themselves be partitioned into additional partitions, such as, for example, droplets or wells. Unique identifiers, e.g., barcodes, may be previously, subsequently or concurrently delivered to the cell or virus or macromolecular constituent(s) of the cell or virus, in order to allow for the later attribution of the characteristics of the cell or virus to the particular compartment. Barcodes may be delivered, for example on an oligonucleotide, to a partition via any suitable mechanism.

Figure 1B:
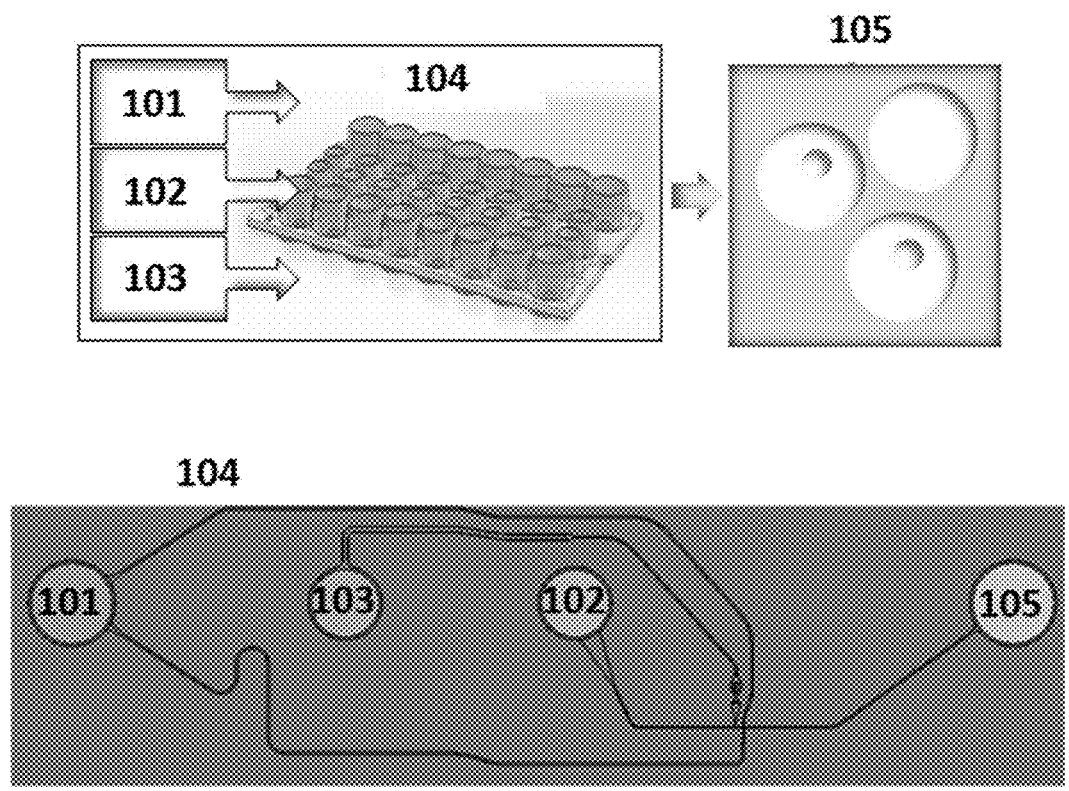
FIG. 1B photographically illustrates an example microfluidic architecture for generating cell beads.

An overview of an example method 100 for generating partitions comprising partitions encapsulating a cell (e.g., a fixed cell, a cross-linked cell) or virus or its macromolecular constituent(s) and barcodes is schematically depicted in FIG. 1A. Method 100 comprises three different phases 110, 120 and 130 that correspond to generation of cell beads comprising a cell or virus or its macromolecular constituent(s) (110); solvent exchange to bring generated partitions into an aqueous phase, cell or virus lysis and denaturation of the cell or virus or macromolecular constituent(s) of the cell or virus (120); and generation of partitions comprising the generated cell beads and barcodes and subsequent tagging (e.g., barcoding) (130). With regard to phase 110, an oil 101, polymeric or gel precursors 102 and cells 103 are provided to a microfluidic chip 104. A photograph of an example microfluidic chip 104 is shown in FIG. 1B. As shown in FIG. 1B, the microfluidic chip 104 comprises a plurality of reservoirs for the oil 101, polymeric or gel precursors 102 and cell or virus reagents 103. Polymeric or gel precursors 102 and cell or virus reagents 103 are flowed (e.g., via the action of an applied force, such as negative pressure via a vacuum or positive pressure via a pump) from their reservoirs to a first channel junction at which point they combine to form an aqueous stream. This aqueous stream is then flowed to a second channel junction, to which oil 101 is also provided. The aqueous stream provided from the first channel junction is immiscible with the oil 101 resulting in the generation of a suspension of aqueous droplets in the oil which then flow to reservoir 105 and represent the product 105 from the microfluidic process. Flow can be controlled within the microfluidic chip 104 via any suitable strategy, including the use of one or more flow regulators in a channel or various channels, dimensioning of microfluidic channels, etc. As shown in both FIG. 1A and FIG. 1B, the product comprises droplets 105 comprising a cell from the cells 103 and polymeric or gel precursors 102.

Continuing with FIG. 1A, the droplets 105 are then subjected to conditions suitable to polymerize or gel the polymeric or gel precursors 102 in the droplets 105, which generates cell beads 106 that encapsulate the cell or virus reagents 103 (e.g., a cell, a fixed cell, a cross-linked cell, component(s) or a cell) in the droplets 105. As the resulting cell beads 106 are suspended in oil, phase 120 is initiated which includes solvent exchange 111 to resuspend the cell beads 106 in an aqueous phase. Additional details and examples regarding solvent exchange are provided elsewhere herein.

The resuspended cell beads 106 can then, in bulk 112, be subjected conditions suitable to lyse cells or viruses associated with the cell beads 106 and, separately or contemporaneously, also subjected, in bulk, to conditions to denature nucleic acids derived from the cells or viruses associated with the cell beads 106. The polymeric matrix of the cell beads 106 effectively hinders or prohibits diffusion of larger molecules, such as nucleic acids, from the cell beads 106. The cell beads 106 are sufficiently porous to denaturation agents that permit denaturation of trapped nucleic acids within the cell beads 106. In some cases, the cell beads can then be subjected, in bulk, to conditions suitable for performing one or more reactions on nucleic acids derived from the cells or viruses associated with the cell beads 106. Additional details and examples regarding reactions on nucleic acids are provided elsewhere herein. The resulting cell beads 113 are then collected 114 and can be stored prior to initiation of phase 130.

Figure 1C:
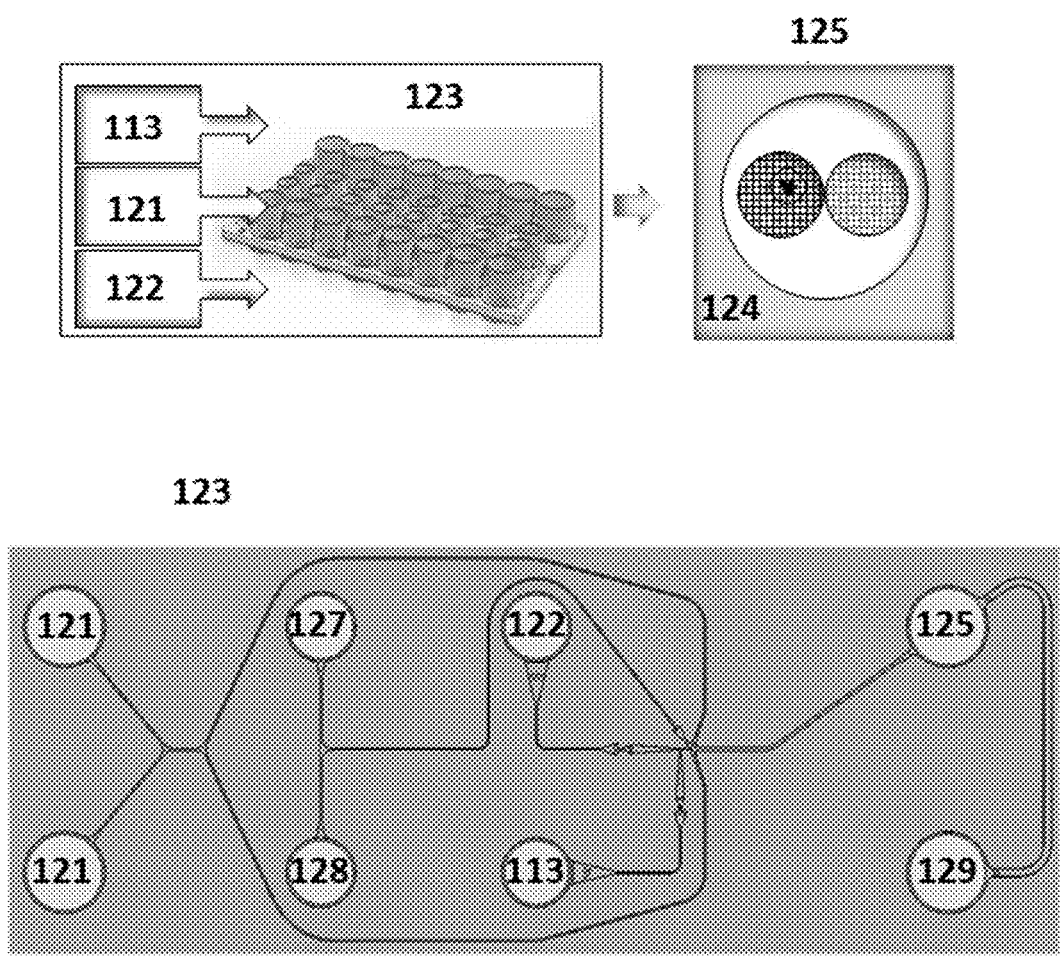
FIG. 1C photographically illustrates an example microfluidic architecture for generating droplets comprising barcoded beads and cell beads.

In phase 130, droplets comprising the cell beads 113 and barcode beads (e.g., gel beads) 122 comprising barcode sequences are generated. As shown in FIG. 1A, an oil 121, the cell beads 113 and barcode beads 122 each comprising a barcode sequence (e.g., each bead comprising a unique barcode sequence) are provided to a microfluidic chip 123. A photograph of an example microfluidic chip 123 is shown in FIG. 1C. As shown in FIG. 1C, the microfluidic chip 123 comprises a plurality of reservoirs for the oil 121, cell beads 113 and barcode beads 122. The chip also includes additional reservoirs 127 and 128 that may be used to supply additional reagents (e.g., reagents for nucleic acid amplification, reagents that can degrade or dissolve cell beads 113 and/or barcode beads 122, reagents that degrade linkages between barcodes and barcode beads 122, etc.) to phase 130. Cell beads 113 and barcode beads 122 are flowed (e.g., via the action of an applied force, such as negative pressure via a vacuum or positive pressure via a pump) from their reservoirs to a first channel junction at which point they combine to form an aqueous mixture. Materials from reservoirs 127 and 128 can also be provided to the mixture at the first channel junction.

Alternatively, cell beads and barcode beads can be mixed before introduction into the microfluidic chip. In this case, a single reservoir of the microfluidic chip 123 comprises a mixture of cell beads and barcode beads. The ratio of cell beads to barcode beads in the mixture can be varied to alter the number of droplets generated that comprise a single cell bead and a single barcode bead. The mixture of cell beads and barcode beads may be flowed (e.g., via the action of an applied force, such as negative pressure via a vacuum or positive pressure via a pump) from the reservoir to a first channel junction, in some cases together with materials from reservoirs 127 and/or 128. As an alternative or in addition to, cells may be mixed with barcode beads. For example, a collection of cells and cell beads may be mixed with barcode beads, or a collection of cells may be mixed with barcode beads.

In some examples, the mixture comprising cell beads (or cells), barcode beads, and in some cases additional reagents is then flowed to a second channel junction, to which oil 121 is also provided. The aqueous mixture provided from the first channel junction is immiscible with the oil 121 resulting in the generation of a suspension of aqueous droplets 125 in the oil 124 which then flow to a reservoir and represent the product from the microfluidic process. The microfluidic chip can also include a reservoir 129 that can accept excess oil from the stream emerging from the second channel. Flow can be controlled within the microfluidic chip 123 via any suitable strategy, including the use of one or more flow regulators (see FIGS. 1C and 1D) in a channel or that connect channels, use of various channels, dimensioning of channels, etc. As shown in both FIG. 1A and FIG. 1C, the product comprises droplets 125 comprising a cell bead 113 and a barcode bead 122, in addition to any other reagents provided by reservoirs 127 and 128. In some cases, a given droplet of the droplets 125 comprises a single cell bead and a single barcode bead.

As in 126 of FIG. 1A, where reagents that degrade or dissolve the cell beads 113, barcoded beads 122 and/or linkages between barcodes and barcode beads 122 are present in droplets, these reagents can release the nucleic acids trapped in the cell beads 113 from the cell beads 113 and release the barcodes from the barcode beads 122. The released barcodes can then interact with the released nucleic acids to generate barcoded constructs for nucleic acid sequencing as described elsewhere herein. Where a given droplet comprises a single cell bead and a single barcode bead comprising oligonucleotides having a common barcode sequence, a given sequencing construct generated from the given droplet 125 can be associated with the cell or virus of the given cell bead via its barcode sequence.

Figure 1D:
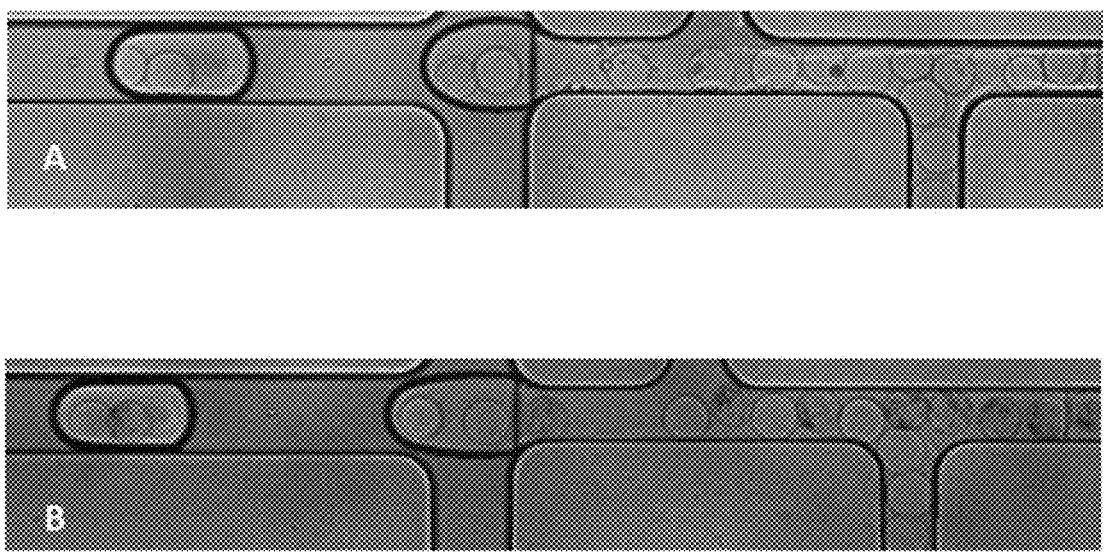
FIG. 1D photographically illustrates droplets comprising barcoded beads and cell beads generated with the architecture shown in FIG. 1C.

FIG. 1D photographically depicts two example runs demonstrating the generation of droplets 125 comprising cell beads and barcode beads using the example method shown in FIG. 1A and microfluidic devices depicted in FIGS. 1B and 1C. In FIG. 1D (panel A), droplets comprising cell beads and barcode beads are shown and in FIG. 1D (panel B) droplets comprising cell beads comprising magnetic materials and barcode beads are shown.

Figure 31:
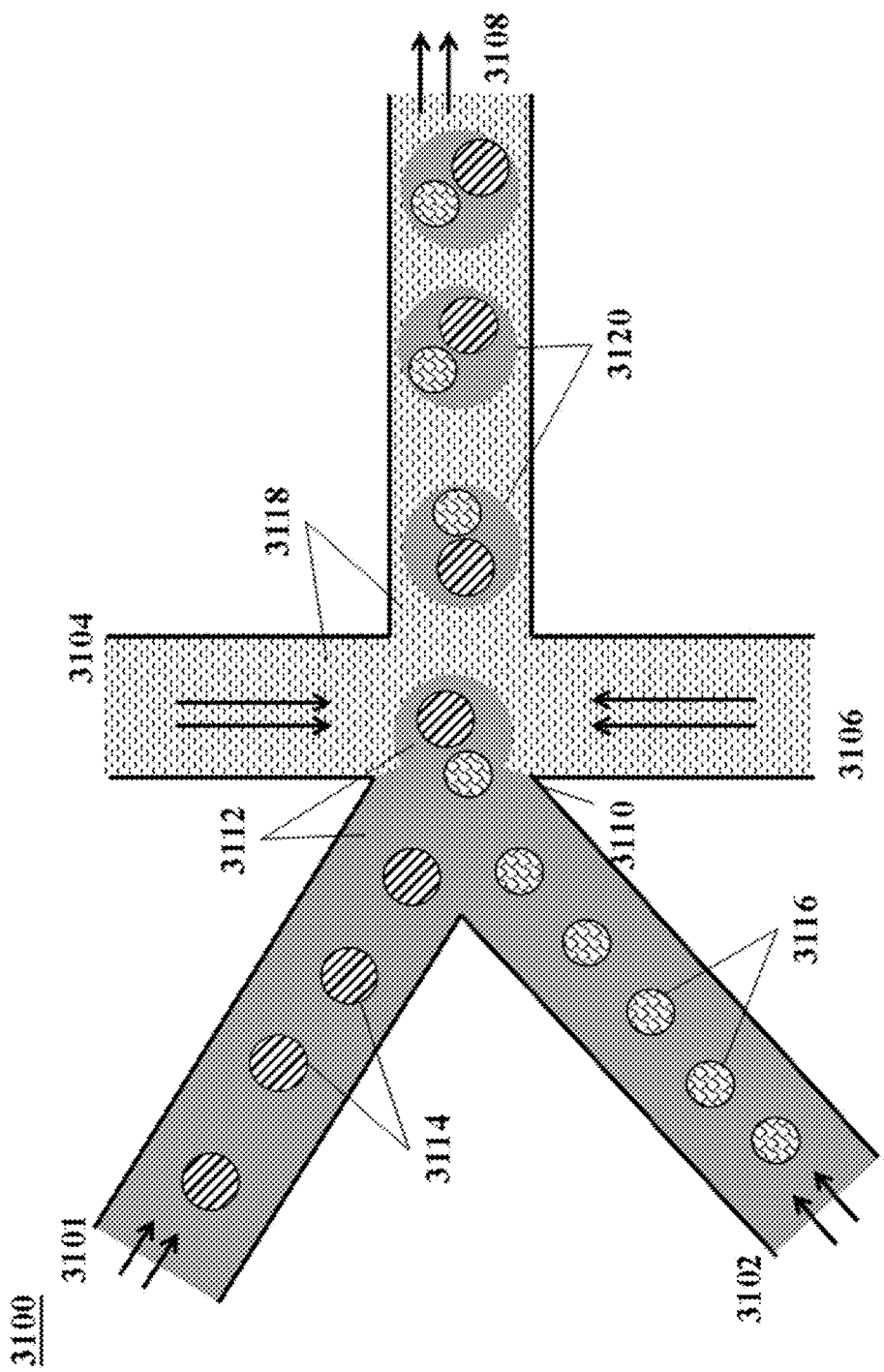
FIG. 31 shows an example of a microfluidic channel structure for delivering cell beads and barcoded beads to droplets.

FIG. 31 shows an example of a microfluidic channel structure 3100 for delivering barcode carrying beads to droplets. The channel structure 3100 can include channel segments 3101, 3102, 3104, 3106 and 3108 communicating at a channel junction 3110. In operation, the channel segment 3101 may transport an aqueous fluid 3112 that includes a plurality of beads 3114 (e.g., with nucleic acid molecules, oligonucleotides, molecular tags) along the channel segment 3101 into junction 3110. The plurality of beads 3114 may be sourced from a suspension of beads. For example, the channel segment 3101 may be connected to a reservoir comprising an aqueous suspension of beads 3114. The channel segment 3102 may transport the aqueous fluid 3112 that includes a plurality of cell beads 3116 along the channel segment 3102 into junction 3110. The plurality of cell beads 3116 may be sourced from a suspension of cell beads. For example, the channel segment 3102 may be connected to a reservoir comprising an aqueous suspension of cell beads 3116. In some instances, the aqueous fluid 3112 in either the first channel segment 3101 or the second channel segment 3102, or in both segments, can include one or more reagents, as further described below. A second fluid 3118 that is immiscible with the aqueous fluid 3112 (e.g., oil) can be delivered to the junction 3110 from each of channel segments 3104 and 3106. Upon meeting of the aqueous fluid 3112 from each of channel segments 3101 and 3102 and the second fluid 3118 from each of channel segments 3104 and 3106 at the channel junction 3110, the aqueous fluid 3112 can be partitioned as discrete droplets 3120 in the second fluid 3118 and flow away from the junction 3110 along channel segment 3108. The channel segment 3108 may deliver the discrete droplets to an outlet reservoir fluidly coupled to the channel segment 3108, where they may be harvested.

As an alternative, the channel segments 3101 and 3102 may meet at another junction upstream of the junction 3110. At such junction, beads and cell beads may form a mixture that is directed along another channel to the junction 3110 to yield droplets 3120. The mixture may provide the beads and cell beads in an alternating fashion, such that, for example, a droplet comprises a single bead and a single cell bead.

Beads, cell beads and droplets may flow along channels at substantially regular flow profiles (e.g., at regular flow rates). Such regular flow profiles may permit a droplet to include a single bead and a single cell bead. Such regular flow profiles may permit the droplets to have an occupancy (e.g., droplets having beads and cell beads) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 3118 can comprise an oil, such as a fluorinated oil, that includes a fluorosurfactant for stabilizing the resulting droplets, for example, inhibiting subsequent coalescence of the resulting droplets 3120.

A discrete droplet that is generated may include an individual cell bead 3116. A discrete droplet that is generated may include a barcode or other reagent carrying bead 3114. A discrete droplet generated may include both an individual cell bead and a barcode carrying bead, such as droplets 3120. In some instances, a discrete droplet may include more than one individual cell bead or no cell bead. In some instances, a discrete droplet may include more than one bead or no bead. A discrete droplet may be unoccupied (e.g., no beads, no cell beads).

Beneficially, a discrete droplet partitioning a cell bead and a barcode carrying bead may effectively allow the attribution of the barcode to macromolecular constituents of the cell bead within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 3100 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A partition may be a droplet. The droplet may be formed by bringing a first phase in contact with a second phase that is immiscible with the first phase. As an alternative, the partition may be a well as part of a plurality of wells. As another alternative, the partition may be a chamber as part of a plurality of chambers. Partitions may be fluidically isolated from one another.

In some embodiments, barcoded oligonucleotides are delivered to a partition via a microcapsule, such as a bead (e.g., gel bead) or a droplet. In some cases, barcoded oligonucleotides are initially associated with the microcapsule and then released from the microcapsule upon application of a stimulus which allows the oligonucleotides to dissociate or to be released from the microcapsule.

A microcapsule, in some embodiments, comprises a bead, such as a droplet comprising the bead. As an alternative, the microcapsule can be a bead (e.g., gel bead). In some embodiments, a bead may be porous, non-porous, solid, semi-solid, semi-fluidic, or fluidic. In some embodiments, a bead may be dissolvable, disruptable, or degradable. In some cases, a bead may not be degradable. The bead may be a solid or semi-solid particle. In some embodiments, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the beads are silica beads. In some cases, the beads are rigid. In some cases, the beads may be flexible and/or compressible.

In some embodiments, the bead may contain molecular precursors (e.g., monomers or polymers), which may form a polymer network via polymerization of the precursors. In some cases, a precursor may be an already polymerized species capable of undergoing further polymerization via, for example, a chemical cross-linkage. In some cases, a precursor comprises one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers.

A bead may comprise natural and/or synthetic materials. For example, a polymer can be a natural polymer or a synthetic polymer. In some cases, a bead comprises both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and combinations (e.g., co-polymers) thereof. Beads may also be formed from materials other than polymers, including lipids, micelles, ceramics, glass-ceramics, material composites, metals, other inorganic materials, and others.

In some cases, a chemical cross-linker may be a precursor used to cross-link monomers during polymerization of the monomers and/or may be used to attach oligonucleotides (e.g., barcoded oligonucleotides) to the bead. In some cases, polymers may be further polymerized with a cross-linker species or other type of monomer to generate a further polymeric network. Non-limiting examples of chemical cross-linkers (also referred to as a "crosslinker" or a "cross-linker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilane, N,N'diallyltartardiamide (DATD), N,N'-Bis(acryloyl)cystamine (BAC), or homologs thereof. In some cases, the crosslinker used in the present disclosure contains cystamine.

Crosslinking may be permanent or reversible, depending upon the particular crosslinker used. Reversible crosslinking may allow for the polymer to linearize or dissociate under appropriate conditions. In some cases, reversible crosslinking may also allow for reversible attachment of a material bound to the surface of a bead. In some cases, a cross-linker may form disulfide linkages. In some cases, the chemical cross-linker forming disulfide linkages may be cystamine or a modified cystamine.

In some embodiments, disulfide linkages can be formed between molecular precursor units (e.g., monomers, oligomers, or linear polymers) or precursors incorporated into a bead and oligonucleotides. Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some embodiments, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some embodiments, the bead may comprise covalent or ionic bonds between polymeric precursors (e.g., monomers, oligomers, linear polymers), oligonucleotides, primers, and other entities. In some cases, the covalent bonds comprise carbon-carbon bonds or thioether bonds.

In some cases, a bead may comprise an acrydite moiety, which in certain aspects may be used to attach one or more oligonucleotides (e.g., barcode sequence, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as an oligonucleotide (e.g., barcode sequence, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment is reversible, such that when the disulfide bond is broken (e.g., in the presence of a reducing agent), the attached species is released from the bead. In other cases, an acrydite moiety comprises a reactive hydroxyl group that may be used for attachment.

Functionalization of beads for attachment of oligonucleotides may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to an oligonucleotide, such as a primer (e.g., a primer for amplifying target nucleic acids, barcoded oligonucleotide, etc) to be incorporated into the bead. In some cases, the primer comprises a P5 sequence for attachment to a sequencing flow cell for Illumina sequencing. In some cases, the primer comprises a P7 sequence for attachment to a sequencing flow cell for Illumina sequencing. In some cases, the primer comprises a barcode sequence. In some cases, the primer further comprises a unique molecular identifier (UMI). In some cases, the primer comprises an R1 primer sequence for Illumina sequencing. In some cases, the primer comprises an R2 primer sequence for Illumina sequencing.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than about 10,000, less than about 100,000, less than about 1,000,000, less than about 10,000,000, less than about 100,000,000, less than about 1,000,000,000, less than about 10,000,000,000, or less than about 100,000,000,000) of reducing agent may be used for reduction. Controlling the number of disulfide linkages that are reduced to free thiols may be useful in ensuring bead structural integrity during functionalization. In some cases, optically-active agents, such as fluorescent dyes may be may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature or temperature change, subjecting the beads to a higher or lower ion concentration, and/or subjecting the beads to an electric field. The de-swelling of the beads may be accomplished, for instance, by transferring the beads in a thermodynamically unfavorable solvent, subjecting the beads to a lower or high temperature or temperature change different from that use to swell the beads, subjecting the beads to a lower or higher ion concentration different from that used to swell the beads, and/or removing the electric field.

Transferring the beads may cause pores in the beads to shrink. Such shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to precursor, another species linked to a precursor, or a precursor itself comprises a labile bond, such as chemically, thermally, or photo-sensitive bonds e.g., disulfide bonds, UV sensitive bonds, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. Barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

Species that do not participate in polymerization may also be encapsulated in beads during bead generation (e.g., during polymerization of precursors). Such species may be entered into polymerization reaction mixtures such that generated beads comprise the species upon bead formation. In some cases, such species may be added to the gel beads after formation. Such species may include, for example, oligonucleotides, reagents for a nucleic acid amplification reaction (e.g., primers (e.g. random primers, primers specific for a given DNA loci), polymerases, nucleotides (e.g. unmodified nucleotides, modified nucleotides, or non-canonical nucleotides), co-factors (e.g., ionic co-factors)) including those described herein, reagents for enzymatic reactions (e.g., enzymes, co-factors, substrates), reagents for reverse transcription (e.g. oligonucleotide primers or reverse transcriptase), or reagents for nucleic acid modification reactions such as polymerization, ligation, digestion, methylation, random mutagenesis, bisulfite conversion, uracil hydrolysis, nucleic acid repair, nucleic acid insertion or cleavage (e.g. via CRISPR/Cas9-mediated or transposon-mediated insertion or cleavage), capping, or decapping. Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. In some cases, barcode sequences (e.g., oligonucleotides comprising barcode sequences) may also be encapsulated within a bead and, in some cases, can be released from a bead via bead degradation and/or by application of a stimulus capable of releasing the species from the bead.

Beads may be of uniform size or heterogeneous size. In some cases, the diameter of a bead may be about 1 µm, 5 µm, 10 µm, 20 µm, 30 µm, 40 µm, 50 µm, 60 µm, 70 µm, 80 µm, 90 µm, 100 µm, 250 µm, 500 µm, or 1 mm. In some cases, a bead may have a diameter of at least about 1 µm, 5 µm, 10 µm, 20 µm, 30 µm, 40 µm, 50 µm, 60 µm, 70 µm, 80 µm, 90 µm, 100 µm, 250 µm, 500 µm, 1 mm, or more. In some cases, a bead may have a diameter of less than about 1 µm, 5 µm, 10 µm, 20 µm, 30 µm, 40 µm, 50 µm, 60 µm, 70 µm, 80 µm, 90 µm, 100 µm, 250 µm, 500 µm, or 1 mm. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain aspects, beads are provided as a population or plurality of beads having a relatively monodisperse size distribution. To provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, or less than 5%.

Beads may be of any suitable shape. Examples of bead shapes include, but are not limited to, spherical, non-spherical, oval, oblong, amorphous, circular, cylindrical, and variations thereof.

In addition to, or as an alternative to the cleavable linkages between the beads and the associated molecules, e.g., barcode containing oligonucleotides, described above, the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead is degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a oligonucleotide, e.g., barcoded oligonucleotide) may result in release of the species from the bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., an oligonucleotide, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent breaks the various disulfide bonds resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

While referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may helpful to avoid exposing such beads to the stimulus or stimuli that cause such degradation prior to the requisite time, in order to avoid premature bead degradation and issues that arise from such degradation, including for example poor flow characteristics and aggregation. By way of example, where beads comprise reducible cross-linking groups, such as disulfide groups, it can be helpful to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be helpful to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than $\frac{1}{10}$th, less than $\frac{1}{50}$th, and even less than $\frac{1}{100}$th of the lower ranges for such materials used in degrading the beads. For example, for DTT, the reducing agent free preparation will typically have less than 0.01 mM, 0.005 mM, 0.001 mM DTT, 0.0005 mM DTT, or even less than 0.0001 mM DTT. In many cases, the amount of DTT will be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

The methods, compositions, devices, and kits of this disclosure may be used with any suitable agent to degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, or 10 mM. The reducing agent may be present at a concentration of at least about 0.1 mM, 0.5 mM, 1 mM, 5 mM, 10 mM, or greater than 10 mM. The reducing agent may be present at a concentration of at most about 0.1 mM, 0.5 mM, 1 mM, 5 mM, or 10 mM.

Any suitable number of barcode molecules (e.g., primer, e.g., barcoded oligonucleotide) can be associated with a bead such that, upon release from the bead, the barcode molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer is limited by the process of producing oligonucleotide bearing beads.

The compartments or partitions can comprise partitions that are flowable within fluid streams. These partitions may comprise, e.g., micro-vesicles that have an outer barrier surrounding an inner fluid center or core, or, in some cases, they may comprise a porous matrix that is capable of entraining and/or retaining materials within its matrix. Partitions can comprise droplets of aqueous fluid within a non-aqueous continuous phase, e.g., an oil phase. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in detail in, e.g., U.S. Patent Application Publication No. 2010/0105112, which is entirely incorporated herein by reference for all purposes.

In the case of droplets in an emulsion, allocating individual cell beads to discrete partitions may generally be accomplished by introducing a flowing stream of cell beads in an aqueous fluid into a flowing stream of a non-aqueous fluid, such that droplets are generated at the junction of the two streams. By providing the aqueous stream at a certain concentration of cell beads, the occupancy of the resulting partitions (e.g., number of cell beads per partition) can be controlled. Where single cell bead partitions are implemented, the relative flow rates of the fluids can be selected such that, on average, the partitions contain less than one cell bead per partition, in order to ensure that those partitions that are occupied, are primarily singly occupied. In some embodiments, the relative flow rates of the fluids can be selected such that a majority of partitions are occupied, e.g., allowing for a small percentage of unoccupied partitions. The flows and channel architectures can be controlled as to ensure a requisite number of singly occupied partitions, less than a certain level of unoccupied partitions and less than a certain level of multiply occupied partitions.

The systems and methods described herein can be operated such that a majority of occupied partitions include no more than one cell bead per occupied partition. In some cases, the partitioning process is conducted such that fewer than 40% of the occupied partitions contain more than one cell bead, fewer than 35% of the occupied partitions contain more than one cell bead, fewer than 30% of the occupied partitions contain more than one cell bead, fewer than 25% of the occupied partitions contain more than one cell bead, fewer than 20% of the occupied partitions contain more than one cell bead, fewer than 15% of the occupied partitions contain more than one cell bead, fewer than 10% of the occupied partitions contain more than one cell bead, or fewer than 5% of the occupied partitions include more than one cell bead per partition.

In some cases, it can be helpful to avoid the creation of excessive numbers of empty partitions or partitions that do not include a cell bead. For example, from a cost perspective and/or efficiency perspective, it may helpful to minimize the number of empty partitions. While this may be accomplished by providing sufficient numbers of cell beads into the partitioning zone, the Poissonian distribution may expectedly increase the number of partitions that may include multiple cell beads. As such, in accordance with aspects described herein, the flow of one or more of the cell beads, or other fluids directed into a partitioning zone can be manipulated to control occupancy of partitions with cell beads such that no more than 60% of the generated partitions are unoccupied, no more than 50% of the generated partitions are unoccupied, no more than 45% of the generated partitions are unoccupied, no more than 40% of the generated partitions are unoccupied, no more than 35% of the generated partitions are unoccupied, no more than 30% of the generated partitions are unoccupied, no more than 25% of the generated partitions are unoccupied, no more than 20% of the generated partitions are unoccupied, or no more than 10% of the generated partitions are unoccupied. These flows can be controlled so as to present non-Poissonian distribution of single occupied partitions while providing lower levels of unoccupied partitions.

The above noted ranges of unoccupied partitions can be achieved while still providing any of the single occupancy rates described above. For example, in many cases, the use of the systems and methods described herein creates resulting partitions (e.g., droplets comprising cell beads) that have multiple occupancy rates of less than 50%, less than 45%, less than 40%, less than 35%, less than 30%, less than 25%, less than 20%, less than 15%, less than 10%, less than 5% or less than 1%.

The above-described occupancy rates are also applicable to partitions that include both cell beads and additional reagents, including, but not limited to, microcapsules or particles (e.g., beads, gel beads) carrying barcoded oligonucleotides. The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded oligonucleotides and a cell bead.

Although described in terms of providing substantially singly occupied partitions, above, in certain cases, it is helpful to provide multiply occupied partitions, e.g., containing two, three, four or more cell beads and/or microcapsules (e.g., beads, gel beads) comprising barcoded oligonucleotides within a single partition. Accordingly, as noted above, the flow characteristics of the cell bead and/or bead containing fluids and partitioning fluids may be controlled to provide for such multiply occupied partitions. In particular, the flow parameters may be controlled to provide a requisite occupancy rate at greater than 50% of the partitions, greater than 55% of the partitions, greater than 60% of the partitions, greater than 65% of the partitions, greater than 70% of the partitions, greater than 75% of the partitions, greater than 80% of the partitions, greater than 85% of the partitions, greater than 90% of the partitions, greater than 95% of the partitions, or higher.

In some cases, additional microcapsules are used to deliver additional reagents to a partition. In such cases, it may be advantageous to introduce different beads into a common channel or droplet generation junction, from different bead sources, i.e., containing different associated reagents, through different channel inlets into such common channel or droplet generation junction. In such cases, the flow and frequency of the different beads into the channel or junction may be controlled to provide for the requisite ratio of microcapsules from each source, while ensuring the requisite pairing or combination of such beads into a partition with the requisite number of cell beads.

The partitions described herein may comprise small volumes, e.g., less than 10 µL, less than 5 µL, less than 1 µL, less than 900 picoliters (pL), less than 800 pL, less than 700 pL, less than 600 pL, less than 500 pL, less than 400 pL, less than 300 pL, less than 200 pL, less than 100 pL, less than 50 pL, less than 20 pL, less than 10 pL, less than 1 pL, less than 500 nanoliters (nL), or even less than 100 nL, 50 nL, or even less.

For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with microcapsules, the sample fluid volume, e.g., including co-partitioned cell beads, within the partitions may be less than 90% of the above described volumes, less than 80%, less than 70%, less than 60%, less than 50%, less than 40%, less than 30%, less than 20%, or even less than 10% the above described volumes.

As is described elsewhere herein, partitioning species may generate a population or plurality of partitions. In such cases, any suitable number of partitions can be generated to generate the plurality of partitions. For example, in a method described herein, a plurality of partitions may be generated that comprises at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions or at least about 1,000,000,000 partitions. Moreover, the plurality of partitions may comprise both unoccupied partitions (e.g., empty partitions) and occupied partitions.

Figure 2:
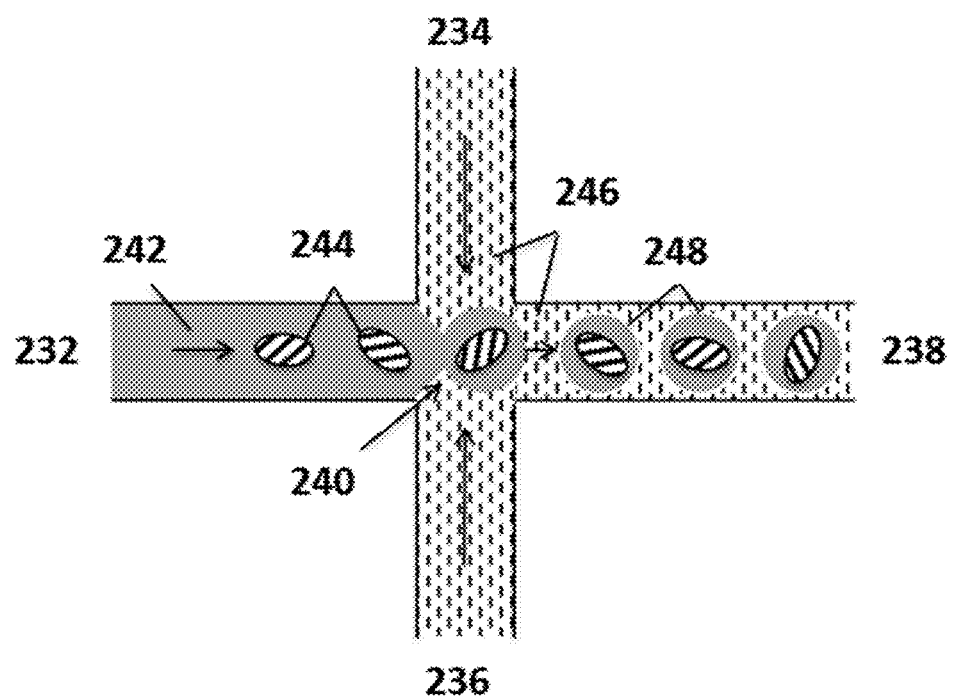
FIG. 2 schematically illustrates a microfluidic channel structure for partitioning individual or small groups of cells or cell beads.

FIG. 2 shows an example of a simplified microfluidic channel structure for partitioning individual cell beads (e.g., a fixed cell, a cross-linked cell, a polymer particle comprising a cell). As described elsewhere herein, in some cases, the majority of occupied partitions include no more than one cell bead per occupied partition and, in some cases, some of the generated partitions are unoccupied. In some cases, though, some of the occupied partitions may include more than one cell bead. In some cases, the partitioning process may be controlled such that fewer than 25% of the occupied partitions contain more than one cell bead, fewer than 20% of the occupied partitions have more than one cell bead, while in some cases, fewer than 10% or even fewer than 5% of the occupied partitions include more than one cell bead per partition. As shown, the channel structure can include channel segments 232, 234, 236 and 238 communicating at a channel junction 240. In operation, a first aqueous fluid 242 that includes suspended cell bead 244, may be transported along channel segment 232 into junction 240, while a second fluid 246 that is immiscible with the aqueous fluid 242 is delivered to the junction 240 from channel segments 234 and 236 to create discrete droplets 118 of the aqueous fluid including individual cell bead 244, flowing into channel segment 238.

This second fluid 246 can comprise an oil, such as a fluorinated oil, that includes a fluorosurfactant for stabilizing the resulting droplets, e.g., inhibiting subsequent coalescence of the resulting droplets. Examples of particularly useful partitioning fluids and fluorosurfactants are described for example, in U.S. Patent Application Publication No. 2010/0105112, which is entirely incorporated herein by reference for all purposes.

In another aspect, in addition to or as an alternative to droplet based partitioning, a cell, virus, components thereof, or macromolecular constituents thereof may be encapsulated within a cell bead. Encapsulation of a cell, virus, components thereof, or macromolecular constituents thereof may be performed by a variety of processes. Such processes combine an aqueous fluid containing the a cell, virus, components thereof, or macromolecular constituents thereof to be analyzed with a polymeric precursor material that may be capable of being formed into a gel or other solid or semi-solid matrix upon application of a particular stimulus to the polymer precursor. Such stimuli include, e.g., thermal stimuli (either heating or cooling), photo-stimuli (e.g., through photo-curing), chemical stimuli (e.g., through cross-linking, polymerization initiation of the precursor (e.g., through added initiators), or the like.

Preparation of cell beads comprising a cell, virus, components thereof, or macromolecular constituents thereof may be performed by a variety of methods. For example, air knife droplet or aerosol generators may be used to dispense droplets of precursor fluids into gelling solutions in order to form cell beads that include individual a cell, virus, components thereof, or macromolecular constituents thereof. Likewise, membrane based encapsulation systems may be used to generate cell beads comprising encapsulated a cell, virus, components thereof, or macromolecular constituents thereof as described herein. Microfluidic systems of the present disclosure, such as that shown in FIG. 2, may be readily used in encapsulating cells as described herein. In particular, and with reference to FIG. 2, the aqueous fluid comprising the cells and the polymer precursor material is flowed into channel junction 240, where it is partitioned into droplets 248 comprising the individual cells 244, through the flow of non-aqueous fluid 246. In the case of encapsulation methods, non-aqueous fluid 246 may also include an initiator to cause polymerization and/or crosslinking of the polymer precursor to form the microcapsule that includes the entrained cells. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, e.g., a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams in channel segments 234 and 236, which initiates the copolymerization of the acrylamide and BAC into a cross-linked polymer network or, hydrogel.

Upon contact of the second fluid stream 246 with the first fluid stream 242 at junction 240 in the formation of droplets, the TEMED may diffuse from the second fluid 246 into the aqueous first fluid 242 comprising the linear polyacrylamide, which will activate the crosslinking of the polyacrylamide within the droplets, resulting in the formation of the gel, e.g., hydrogel, microcapsules 248, as solid or semi-solid beads or particles entraining the cells 244. Although described in terms of polyacrylamide encapsulation, other 'activatable' encapsulation compositions may also be employed in the context of the methods and compositions described herein. For example, formation of alginate droplets followed by exposure to divalent metal ions, e.g., Ca2+, can be used as an encapsulation process using the described processes. Likewise, agarose droplets may also be transformed into capsules through temperature based gelling, e.g., upon cooling, or the like.

In some cases, an encapsulated cell, virus, components thereof, or macromolecular constituents thereof can be selectively releasable from the microcapsule, e.g., through passage of time, or upon application of a particular stimulus, that degrades the microcapsule sufficiently to allow the cell, or its contents to be released from the microcapsule, e.g., into a partition, such as a droplet. For example, in the case of the polyacrylamide polymer described above, degradation of the microcapsule may be accomplished through the introduction of an appropriate reducing agent, such as DTT or the like, to cleave disulfide bonds that cross link the polymer matrix (see, e.g., U.S. Patent Application Publication No. 2014/0378345, which is entirely incorporated herein by reference for all purposes).

In accordance with certain aspects, the cell beads may be contacted with lysis reagents in order to release the contents of cells or viruses associated with the cell bead. In some cases, the lysis agents can be contacted with a cell bead suspension in bulk after cell bead formation. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), a surfactant based lysis solution (e.g., TRITON X-100 (4-(1,1,3,3-Tetramethylbutyl)phenyl-polyethylene glycol), Tween 20, sodium dodecyl sulfate (SDS)) for example, as well as other commercially available lysis enzymes. Electroporation, thermal, acoustic or mechanical cellular disruption may also be used in certain cases. In some cases, such methods give rise to a pore size that is sufficiently small to retain nucleic acid fragments of a particular size, following cellular disruption.

Other reagents can also be contacted with the cell beads, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated cell beads, the cell beads may be exposed to an appropriate stimulus to release the cell beads or their contents from a co-partitioned microcapsule. For example, in some cases, a chemical stimulus may be co-partitioned along with an encapsulated cell bead to allow for the degradation of the microcapsule and release of the cell or its contents into the larger partition. In some cases, this stimulus may be the same as the stimulus described elsewhere herein for release of oligonucleotides from their respective microcapsule (e.g., bead). In alternative aspects, this may be a different and non-overlapping stimulus, in order to allow an encapsulated cell bead release its contents into a partition at a different time from the release of oligonucleotides into the same partition.

Additional reagents may also be co-partitioned with the cell beads. In some instances, reagents may be encapsulated within the cell beads. In other instances, reagents may be outside the cell beads. Reagents may be those useful in modification of a cell bead's nucleic acid (e.g., DNA, RNA, etc.), where such modification may include ligation, digestion, methylation, random mutagenesis, bisulfite conversion, uracil hydrolysis, nucleic acid repair, capping, or decapping. Additional reagents may also include reagents useful in amplification of a cell bead's nucleic acid, including primers (e.g. random primers, primers specific for given DNA loci), polymerases, nucleotides (e.g. unmodified nucleotides, modified nucleotides, or non-canonical nucleotides), or co-factors (e.g., ionic co-factors). Additional reagents may also include proteases to remove proteins bound to a cell bead's nucleic acids and transposons to fragment or insert a known sequence into a cell bead's DNA. Additional reagents may also include a nucleic acid, a Cas9 nuclease and a guide RNA to mediate editing of a cell bead's DNA. Additional reagents may also include endonucleases to fragment a cell bead's DNA, DNA polymerase enzymes and nucleotides used to amplify the cell bead's nucleic acid fragments and to attach the barcodes to the amplified fragments. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

Macromolecular components may be processed (e.g., subjected to nucleic acid amplification) prior to generation of cell beads. Alternatively or in addition, macromolecular components contained within the cell beads may be further processed. Further processing may, in some instances, occur prior to partitioning of the cell beads into discrete partitions. Further processing may also occur following partitioning of the cell beads into discrete partitions and prior to release of the contents of the cell beads into their respective partitions. Alternatively or additionally, further processing may occur once the contents of the cell beads are released into their respective partitions. Further processing may include, for example, nucleic acid modification, where such modification may include ligation, digestion, methylation, random mutagenesis, bisulfite conversion, uracil hydrolysis, nucleic acid repair, capping, or decapping. Further processing may also include nucleic acid amplification, including isothermal amplification (e.g., loop mediated isothermal amplification or multiple displacement amplification) or PCR (e.g., DOP-PCR), where amplification may incorporate unmodified bases, modified bases, or non-canonical bases. Additional processing may also include nucleic acid insertion or cleavage (e.g., via CRISPR/Cas9-mediated or transposon-mediated insertion or cleavage). Additional processing may also include reverse transcription, where reverse transcription may incorporate unmodified bases, modified bases, or non-canonical bases.

Nucleic acid amplification may include performing one or more extension reactions. Such one or more extension reactions may be performed using a primer or multiple primers. Nucleic acid amplification may generate one or more copies of a starting molecule. In some examples, nucleic acid amplification includes a single extension reaction without any additional extension reactions. In such a case, for example, nucleic acid amplification may generate a larger molecule from a smaller starting molecule without generating a copy of the smaller starting molecule or the larger molecule. However, in some cases, nucleic acid amplification may include generating the larger molecule and subsequently generating one or more copies of the larger molecule. Nucleic acid amplification may be exponential amplification. Alternatively, nucleic acid amplification may not be exponential amplification (e.g., may be linear amplification).

Examples of nucleic acid amplification are provided elsewhere herein. Nucleic acid amplification may be isothermal amplification, PCR (e.g., DOP-PCR) or PHASE, for example. In some cases, nucleic acid amplification may not be PCR.

In some cases, a cell bead comprising a nucleic acid molecule may be provided in a partition (e.g., droplet), the nucleic acid molecule may be released from the cell bead in the partition, and the nucleic acid molecule may be recovered from the partition without any processing. The nucleic acid molecule may then be processed once recovered from the partition. For example, the nucleic acid molecule may be subjected to nucleic acid amplification and/or sequencing.

In accordance with the methods and systems described herein, the macromolecular component contents of individual cell beads can be provided with unique identifiers such that, upon characterization of those macromolecular components they may be attributed as having been derived from the same cell bead or particles (and, thus, cell or virus originally associated with the cell bead). The ability to attribute characteristics to a cell, virus, components thereof, or macromolecular constituents thereof of individual cell beads or groups of cell beads is provided by the assignment of unique identifiers specifically to an individual cell bead or groups of cell beads. Unique identifiers, e.g., in the form of nucleic acid barcodes can be assigned or associated with individual cell beads or populations of cell bead, in order to tag or label the cell bead's macromolecular components (and as a result, its characteristics) with the unique identifiers. These unique identifiers can then be used to attribute the cell bead's components and characteristics to the original cell or virus(s) associated with the cell bead. In some aspects, this is performed by co-partitioning the individual cell bead or groups of cell beads with the unique identifiers. In some aspects, the unique identifiers are provided in the form of oligonucleotides that comprise nucleic acid barcode sequences that may be attached to or otherwise associated with the nucleic acid contents of individual cell bead, or to other components of the cell bead, and particularly to fragments of those nucleic acids. The oligonucleotides are partitioned such that as between oligonucleotides in a given partition, the nucleic acid barcode sequences contained therein are the same, but as between different partitions, the oligonucleotides can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

The co-partitioned oligonucleotides can also comprise other functional sequences useful in the processing of the nucleic acids from the co-partitioned cell beads. These sequences include, e.g., targeted or random/universal amplification primer sequences for amplifying the genomic DNA from the individual cell beads within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each includes large numbers of the above described barcoded oligonucleotides releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the oligonucleotides into the partitions, as they are capable of carrying large numbers of oligonucleotide molecules, and may be configured to release those oligonucleotides upon exposure to a particular stimulus, as described elsewhere herein. In some cases, the population of beads will provide a diverse barcode sequence library that includes at least 100 different barcode sequences, at least 500 different barcode sequences, at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each bead can be provided with large numbers of oligonucleotide molecules attached. In particular, the number of molecules of oligonucleotides including the barcode sequence on an individual bead can be at least 100 oligonucleotide molecules, at least 500 oligonucleotide molecules, at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

Moreover, when the population of beads is partitioned, the resulting population of partitions can also include a diverse barcode library that includes at least 100 different barcode sequences, at least 500 different barcode sequences, at least 1,000 different barcode sequences, at least 5,000 different barcode sequences, at least 10,000 different barcode sequences, at least at least 50,000 different barcode sequences, at least 100,000 different barcode sequences, at least 1,000,000 different barcode sequences, at least 5,000,000 different barcode sequences, or at least 10,000,000 different barcode sequences. Additionally, each partition of the population can include at least 100 oligonucleotide molecules, at least 500 oligonucleotide molecules, at least 1,000 oligonucleotide molecules, at least 5,000 oligonucleotide molecules, at least 10,000 oligonucleotide molecules, at least 50,000 oligonucleotide molecules, at least 100,000 oligonucleotide molecules, at least 500,000 oligonucleotides, at least 1,000,000 oligonucleotide molecules, at least 5,000,000 oligonucleotide molecules, at least 10,000,000 oligonucleotide molecules, at least 50,000,000 oligonucleotide molecules, at least 100,000,000 oligonucleotide molecules, and in some cases at least 1 billion oligonucleotide molecules.

In some cases, it may be helpful to incorporate multiple different barcodes within a given partition, either attached to a single or multiple beads within the partition. For example, in some cases, a mixed, but known barcode sequences set may provide greater assurance of identification in the subsequent processing, e.g., by providing a stronger address or attribution of the barcodes to a given partition, as a duplicate or independent confirmation of the output from a given partition.

The oligonucleotides are releasable from the beads upon the application of a particular stimulus to the beads. In some cases, the stimulus may be a photo-stimulus, e.g., through cleavage of a photo-labile linkage that releases the oligonucleotides. In other cases, a thermal stimulus may be used, where elevation of the temperature of the beads environment will result in cleavage of a linkage or other release of the oligonucleotides form the beads. In still other cases, a chemical stimulus is used that cleaves a linkage of the oligonucleotides to the beads, or otherwise results in release of the oligonucleotides from the beads. In one case, such compositions include the polyacrylamide matrices described above for encapsulation of a cell, virus, components thereof, or macromolecular constituents thereof, and may be degraded for release of the attached oligonucleotides through exposure to a reducing agent, such as DTT.

Figure 3:
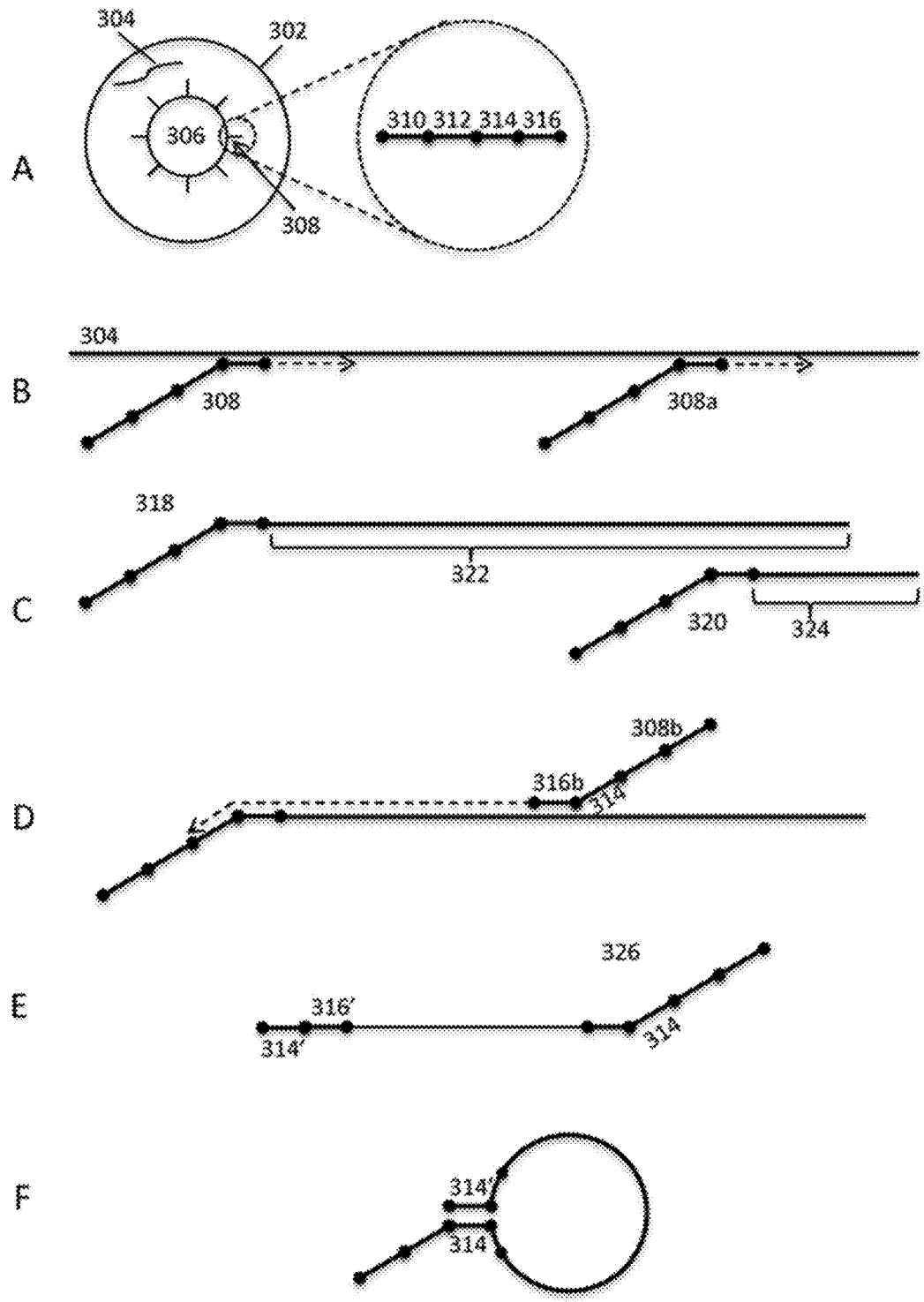
FIGS. 3A-3F schematically illustrate an example process for amplification and barcoding of cell's nucleic acids.

As described herein, the cell or virus of a cell bead may include any nucleic acids within including, for example, the cell or virus's DNA, e.g., genomic DNA, RNA, e.g., messenger RNA, and the like. For example, in some cases, the methods and systems described herein are used in characterizing expressed mRNA, including, e.g., the presence and quantification of such mRNA, and may include RNA sequencing processes as the characterization process. Alternatively or additionally, the reagents partitioned along with the cell bead may include reagents for the conversion of mRNA into cDNA, e.g., reverse transcriptase enzymes and reagents, to facilitate sequencing processes where DNA sequencing is employed. Reagents may be comprised in the cell bead. Reagents may be used (e.g., used for the conversion of mRNA into cDNA) prior to partitioning. Alternatively or additionally, reagents may be used following partitioning. In some cases, where the nucleic acids to be characterized comprise DNA, e.g., gDNA, a schematic illustration of an example of this is shown in FIG. 3.

As shown, oligonucleotides that include a barcode sequence are co-partitioned in, e.g., a droplet 302 in an emulsion, along with a sample nucleic acid 304. A sample nucleic acid may be from a cell bead. As noted elsewhere herein, the oligonucleotides 308 may be provided on a bead 306 that is co-partitioned with the sample nucleic acid 304, which oligonucleotides are releasable from the bead 306, as shown in panel A. The oligonucleotides 308 include a barcode sequence 312, in addition to one or more functional sequences, e.g., sequences 310, 314 and 316. For example, oligonucleotide 308 is shown as comprising barcode sequence 312, as well as sequence 310 that may function as an attachment or immobilization sequence for a given sequencing system, e.g., a P5 sequence used for attachment in flow cells of an Illumina Hiseq® or Miseq® system. As shown, the oligonucleotides also include a primer sequence 316, which may include a random or targeted N-mer for priming replication of portions of the sample nucleic acid 304. Also included within oligonucleotide 308 is a sequence 314 which may provide a sequencing priming region, such as a "read1" or R1 priming region, that is used to prime polymerase mediated, template directed sequencing by synthesis reactions in sequencing systems. The functional sequences may be selected to be compatible with a variety of different sequencing systems, e.g., 454 Sequencing, Ion Torrent Proton or PGM, Illumina X10, etc., and the requirements thereof. In many cases, the barcode sequence 312, immobilization sequence 310 and R1 sequence 314 may be common to all of the oligonucleotides attached to a given bead. The primer sequence 316 may vary for random N-mer primers, or may be common to the oligonucleotides on a given bead for certain targeted applications.

In some cases, the functional sequences may include primer sequences useful for RNA-seq applications. For example, in some cases, the oligonucleotides may include poly-T primers for priming reverse transcription of RNA for RNA-seq. In still other cases, oligonucleotides in a given partition, e.g., included on an individual bead, may include multiple types of primer sequences in addition to the common barcode sequences, such as DNA-sequencing or RNA sequencing primers, e.g., poly-T primer sequences included within the oligonucleotides coupled to the bead. In such cases, materials derived from a single partitioned cell bead may be subjected to DNA or RNA sequencing processes.

Based upon the presence of primer sequence 316, the oligonucleotides can prime the sample nucleic acid as shown in panel B, which allows for extension of the oligonucleotides 308 and 308a using polymerase enzymes and other extension reagents also co-partitioned with the bead 306 and sample nucleic acid 304. As shown in panel C, following extension of the oligonucleotides that, for random N-mer primers, may anneal to multiple different regions of the sample nucleic acid 304; multiple overlapping complements or fragments of the nucleic acid are created, e.g., fragments 318 and 320. Although including sequence portions that are complementary to portions of sample nucleic acid, e.g., sequences 322 and 324, these constructs are generally referred to herein as comprising fragments of the sample nucleic acid 304, having the attached barcode sequences.

The barcoded nucleic acid fragments may then be subjected to characterization, e.g., through sequence analysis, or they may be further amplified in the process, as shown in panel D. For example, additional oligonucleotides, e.g., oligonucleotide 308b, also released from bead 306, may prime the fragments 318 and 320. This is shown for fragment 318. In particular, again, based upon the presence of the random N-mer primer 316b in oligonucleotide 308b (which in many cases can be different from other random N-mers in a given partition, e.g., primer sequence 316), the oligonucleotide anneals with the fragment 318, and is extended to create a complement 326 to at least a portion of fragment 318 which includes sequence 328, that comprises a duplicate of a portion of the sample nucleic acid sequence. Extension of the oligonucleotide 308b continues until it has replicated through the oligonucleotide portion 308 of fragment 318. As noted elsewhere herein, and as illustrated in panel D, the oligonucleotides may be configured to prompt a stop in the replication by the polymerase at a particular point, e.g., after replicating through sequences 316 and 314 of oligonucleotide 308 that is included within fragment 318. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 312 to prevent a non-uracil tolerant polymerase to cease replication of that region. As a result a fragment 326 is created that includes the full-length oligonucleotide 308b at one end, including the barcode sequence 312, the attachment sequence 310, the R1 primer region 314, and the random N-mer sequence 316b. At the other end of the sequence may be included the complement 316' to the random N-mer of the first oligonucleotide 308, as well as a complement to all or a portion of the R1 sequence, shown as sequence 314'. The R1 sequence 314 and its complement 314' are then able to hybridize together to form a partial hairpin structure 328. Because the random N-mers differ among different oligonucleotides, these sequences and their complements may not be expected to participate in hairpin formation, e.g., sequence 316', which is the complement to random N-mer 316, may not be expected to be complementary to random N-mer sequence 316b. This may not be the case for other applications, e.g., targeted primers, where the N-mers may be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 326.

In general, the amplification of the nucleic acids of the cell bead may be performed until the barcoded overlapping fragments within the partition constitute at least 1× coverage of the particular portion or all of the associated cell or virus' genome, at least 2×, at least 3×, at least 4×, at least 5×, at least 10×, at least 20×, at least 40× or more coverage of the genome or its relevant portion of interest. Once the barcoded fragments are produced, they may be directly sequenced on an appropriate sequencing system, e.g., an Illumina Hiseq®, Miseq® or X10 system, or they may be subjected to additional processing, such as further amplification, attachment of other functional sequences, e.g., second sequencing primers, for reverse reads, sample index sequences, and the like.

Figure 4:
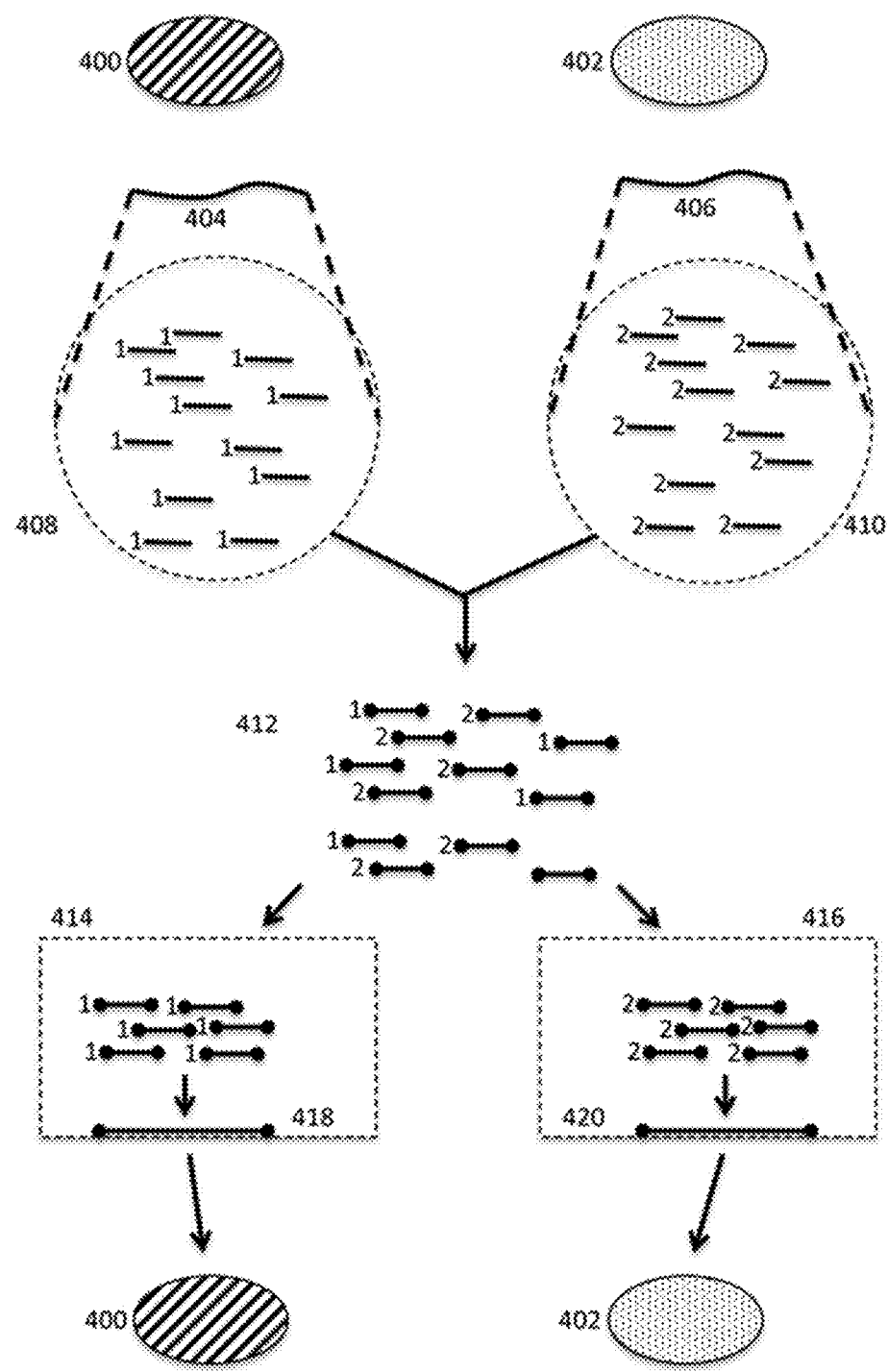
FIG. 4 provides a schematic illustration of use of barcoding of a cell's nucleic acids in attributing sequence data to individual cells or groups of cells for use in their characterization.

All of the fragments from multiple different partitions may then be pooled for sequencing on high throughput sequencers as described herein, where the pooled fragments comprise a large number of fragments derived from the nucleic acids of different cell beads or small cell bead populations, but where the fragments from the nucleic acids of a given cell bead will share the same barcode sequence. In particular, because each fragment is coded as to its partition of origin, and consequently its single cell bead or small population of cell beads, the sequence of that fragment may be attributed back to that cell bead or those cell beads (and, thus, the original cell or population of cells or viruses) based upon the presence of the barcode, which will also aid in applying the various sequence fragments from multiple partitions to assembly of individual genomes for different cell beads. This is schematically illustrated in FIG. 4. As shown in an example, a first nucleic acid 404 from a first cell bead 400, and a second nucleic acid 406 from a second cell bead 402 are each partitioned along with their own sets of barcode oligonucleotides as described above. The nucleic acids may comprise a chromosome, entire genome, transcript or other nucleic acid from the cell bead.

Within each partition, each cell bead's nucleic acids 404 and 406 is then processed to separately provide overlapping set of second fragments of the first fragment(s), e.g., second fragment sets 408 and 410. This processing also provides the second fragments with a barcode sequence that is the same for each of the second fragments derived from a particular first fragment. As shown, the barcode sequence for second fragment set 408 is denoted by "1" while the barcode sequence for fragment set 410 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 408 and 410, may then be pooled for sequencing using, for example, sequence by synthesis technologies available from Illumina or Ion Torrent division of Thermo-Fisher, Inc. Once sequenced, the sequence reads 412 can be attributed to their respective fragment set, e.g., as shown in aggregated reads 414 and 416, at least in part based upon the included barcodes, and in some cases, in part based upon the sequence of the fragment itself. The attributed sequence reads for each fragment set are then assembled to provide the assembled sequence for each cell bead's nucleic acids, e.g., sequences 418 and 420, which in turn, may be attributed to individual cell beads and cell or virus (e.g., cells) encapsulated within the cell beads.

While described in terms of analyzing the genetic material present within or from a cell or virus, the methods and systems described herein may have much broader applicability, including the ability to characterize other aspects of individual cells or viruses or cell or virus populations, by allowing for the allocation of reagents to individual cells or viruses, and providing for the attributable analysis or characterization of those cells or viruses in response to those reagents. These methods and systems are particularly valuable in being able to characterize a cell, virus, components thereof, or macromolecular constituents thereof for, e.g., research, diagnostic, pathogen identification, and many other purposes.

A particularly valuable application of the cell bead processes described herein is in the sequencing and characterization of a diseased cell that is associated with the cell bead. A diseased cell can have altered metabolic properties, gene expression, and/or morphologic features. Exemplary diseases include inflammatory disorders, metabolic disorders, nervous system disorders, and cancer.

Of particular interest are cancer cells. In particular, conventional analytical techniques, including the ensemble sequencing processes alluded to above, are not highly adept at picking small variations in genomic make-up of cancer cells, particularly where those exist in a sea of normal tissue cells. Further, even as between tumor cells, wide variations can exist and can be masked by the ensemble approaches to sequencing (See, e.g., Patel, et al., Single-cell RNA-seq highlights intratumoral heterogeneity in primary glioblastoma, Science DOI: 10.1126/science.1254257 (Published online Jun. 12, 2014), which is entirely incorporated herein by reference for all purposes). Cancer cells may be derived from solid tumors, hematological malignancies, cell lines, or obtained as circulating tumor cells, and subjected to the partitioning processes described above. Upon analysis, one can identify individual cell sequences as deriving from a single cell or small group of cells, and distinguish those over normal tissue cell sequences.

Non-limiting examples of cancer cells include cells of cancers such as Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof.

As with cancer cell analysis, the analysis and diagnosis of fetal health or abnormality through the analysis of fetal cells is a difficult task using conventional techniques. In particular, in the absence of relatively invasive procedures, such as amniocentesis obtaining fetal cell samples can employ harvesting those cells from the maternal circulation. Such circulating fetal cells make up an extremely small fraction of the overall cellular population of that circulation. As a result complex analyses are performed in order to characterize what of the obtained data is likely derived from fetal cells as opposed to maternal cells. By employing the single cell characterization methods and systems described herein, however, one can attribute genetic make up to individual cells, and categorize those cells as maternal or fetal based upon their respective genetic make-up. Further, the genetic sequence of fetal cells may be used to identify any of a number of genetic disorders, including, e.g., aneuploidy such as Down syndrome, Edwards syndrome, and Patau syndrome.

Also of interest are immune cells. Methods and compositions disclosed herein can be utilized for sequence analysis of the immune repertoire. Analysis of sequence information underlying the immune repertoire can provide a significant improvement in understanding the status and function of the immune system.

Non-limiting examples of immune cells which can be analyzed utilizing the methods described herein include B cells, T cells (e.g., cytotoxic T cells, natural killer T cells, regulatory T cells, and T helper cells), natural killer cells, cytokine induced killer (CIK) cells; myeloid cells, such as granulocytes (basophil granulocytes, eosinophil granulocytes, neutrophil granulocytes/hypersegmented neutrophils), monocytes/macrophages, mast cell, thrombocytes/megakaryocytes, and dendritic cells. In some cases, immune cells can be analyzed individually (i.e., as a single cell). In some cases, a single immune cell can be analyzed together with any associated pathogen (e.g., microbe) which may be adhered to the immune cell (e.g., via an immune receptor). In some embodiments, individual T cells are analyzed using the methods disclosed herein. In some embodiments, individual B cells are analyzed using the methods disclosed herein.

Immune cells express various adaptive immunological receptors relating to immune function, such as T cell receptors and B cell receptors. T cell receptors and B cells receptors play a part in the immune response by specifically recognizing and binding to antigens and aiding in their destruction.

The T cell receptor (TCR) is a molecule found on the surface of T cells that is generally responsible for recognizing fragments of antigen as peptides bound to major histocompatibility complex (MHC) molecules. The TCR is generally a heterodimer of two chains, each of which is a member of the immunoglobulin superfamily, possessing an N-terminal variable (V) domain, and a C terminal constant domain. In humans, in 95% of T cells the TCR consists of an alpha ($\alpha$) and beta ($\beta$) chain, whereas in 5% of T cells the TCR consists of gamma and delta ($\gamma/\delta$) chains. This ratio can change during ontogeny and in diseased states as well as in different species. When the TCR engages with antigenic peptide and MHC (peptide/MHC), the T lymphocyte is activated through signal transduction.

Each of the two chains of a TCR contains multiple copies of gene segments—a variable 'V' gene segment, a diversity 'D' gene segment, and a joining T gene segment. The TCR alpha chain is generated by recombination of V and J segments, while the beta chain is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining T gene segment. Each light chain gene contains multiple copies of two different gene segments for the variable region of the protein—a variable 'V' gene segment and a joining T gene segment. The recombination can generate a molecule with one of each of the V, D, and J segments. Furthermore, several bases may be deleted and others added (called N and P nucleotides) at each of the two junctions, thereby generating further diversity. After B cell activation, a process of affinity maturation through somatic hypermutation occurs. In this process progeny cells of the activated B cells accumulate distinct somatic mutations throughout the gene with higher mutation concentration in the CDR regions leading to the generation of antibodies with higher affinity to the antigens. In addition to somatic hypermutation activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

In some embodiments, the methods, compositions and systems disclosed herein are utilized to analyze the various sequences of TCRs and BCRs from immune cells, for example various clonotypes. In some embodiments, methods, compositions and systems disclosed herein are used to analyze the sequence of a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In some embodiments, methods, compositions and systems disclosed herein are used to analyze the sequence of a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions may comprise gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

The ability to characterize individual cells, viruses, components thereof, or macromolecular constituents thereof from larger diverse populations of these entities is also of significant value in both environmental testing as well as in forensic analysis, where samples may, by their nature, be made up of diverse populations of cells or viruses and other material that "contaminate" the sample, relative to the cell(s) or virus(es) for which the sample is being tested, e.g., environmental indicator organisms, toxic organisms, and the like for, e.g., environmental and food safety testing, victim and/or perpetrator cells in forensic analysis for sexual assault, and other violent crimes, and the like.

Additional useful applications of the above described cell bead sequencing and characterization processes are in the field of neuroscience research and diagnosis. In particular, neural cells can include long interspersed nuclear elements (LINEs), or 'jumping' genes that can move around the genome, which cause each neuron to differ from its neighbor cells. Research has shown that the number of LINEs in human brain exceeds that of other tissues, e.g., heart and liver tissue, with between 80 and 300 unique insertions (See, e.g., Coufal, N. G. et al. Nature 460, 1127-1131 (2009), which is entirely incorporated herein by reference for all purposes). These differences have been postulated as being related to a person's susceptibility to neuro-logical disorders (see, e.g., Muotri, A. R. et al. Nature 468, 443-446 (2010), which is entirely incorporated herein by reference for all purposes), or provide the brain with a diversity with which to respond to challenges. As such, the methods described herein may be used in the sequencing and characterization of individual neural cells.

The cell bead analysis methods described herein are also useful in the analysis of gene expression, as noted above, both in terms of identification of RNA transcripts and their quantitation. In particular, using the single cell level analysis methods described herein, one can isolate and analyze the RNA transcripts present in individual cells or viruses, populations of cells or viruses, or subsets of populations of cells or viruses. In particular, in some cases, the barcode oligonucleotides may be configured to prime, replicate and consequently yield barcoded fragments of RNA from individual cells or viruses. For example, in some cases, the barcode oligonucleotides may include mRNA specific priming sequences, e.g., poly-T primer segments that allow priming and replication of mRNA in a reverse transcription reaction or other targeted priming sequences. Alternatively or additionally, random RNA priming may be performed using random N-mer primer segments of the barcode oligonucleotides. Methods for RNA, mRNA and cell feature analysis are provided in U.S. Patent Publication No. 2015/0376609, which is entirely incorporated herein by reference.

In some cases, amplification may be performed using the Partial Hairpin Amplification for Sequencing (PHASE)

method. In a PHASE method, a random N-mer sequence may be used to randomly prime a sample, such as genomic DNA (gDNA). In some embodiments, the random N-mer may comprise a primer. In some cases, the random N-mer may prime a sample. In some cases, the random N-mer may prime genomic DNA. In some cases, the random N-mer may prime DNA fragments. An example PHASE method is shown schematically in FIG. 3. Additional examples of PHASE are provided in U.S. Patent Publication No. 2014/0378345, which is entirely incorporated herein by reference.

Additionally, a random N-mer sequence may also be attached to another oligonucleotide. This oligonucleotide may be a universal sequence and/or may contain one or more primer read sequences that may be compatible with a sequencing device (e.g. Read 1 primer site, Read 2 primer site, Index primer site), one or more barcode sequences, and one or more adaptor segments that may be compatible with a sequencing device (e.g. P5, P7). Alternatively, the oligonucleotide may comprise none of these and may include another sequence.

Via subsequent amplification methods, priming of a sample nucleic acid with a random N-mer may be used to attach an oligonucleotide sequence (e.g., an oligonucleotide sequence comprising a barcode sequence) linked to a random N-mer to the sample nucleic acid, including a sample nucleic acid to be sequenced. Utilizing random primers to prime a sample may introduce significant sequence read errors, due to, for example, the production of undesired amplification products. An example PHASE method is shown schematically in FIG. 3. Additional examples of PHASE are provided in U.S. Patent Publication No. 2014/0378345, which is entirely incorporated herein by reference.

To mitigate undesired amplification products, at least a subsection of an oligonucleotide sequence (e.g., an oligonucleotide comprising a primer) used for PHASE amplification may be substituted with uracil-containing nucleotides in place of thymine containing nucleotides, respectively. In some cases, substitution may be complete (e.g., all thymine containing nucleotides are substituted with uracil containing nucleotides), or may be partial such that a portion of an oligonucleotide's thymine containing nucleotides are substituted with uracil containing nucleotides. In some cases, thymine containing nucleotides in all but the last about 10 to 20, last about 10 to 30, last about 10 to 40, or last about 5 to 40 nucleotides of an oligonucleotide sequence adjacent to a random N-mer sequence are substituted with uracil containing nucleotides, or functional equivalents thereof. In addition, a polymerase that does not accept or process uracil-containing templates may be used for amplification of the sample nucleic acid. In this case, the non-uracil containing portion of about 10 to about 20 nucleotides may be amplified and the remaining portion containing uracil containing nucleotides may not be amplified. In some cases, the portion of an oligonucleotide sequence comprising uracil containing nucleotides may be adjacent to the N-mer sequence. In some cases, the portion of an oligonucleotide sequence comprising uracil containing nucleotides may be adjacent to the barcode sequence. Any portion of an oligonucleotide sequence, including an adaptor segment, barcode, or read primer sequence may comprise uracil containing nucleotides (e.g., substituted for thymine containing nucleotides), depending upon the configuration of the oligonucleotide sequence. In some cases, uracil containing nucleotides can be introduced to oligonucleotides during PHASE amplification with the inclusion of dUTP nucleotides in place of or in combination with dTTPs in amplification reactions.

The dUTP concentration may be increased over time. For instance, the dUTP concentration may be increased at a controlled rate by the inclusion of dCTP deaminase in an amplification reaction mixture. The dUTP concentration may be increased over time by the dCTP-mediated conversion of dCTP into dUTP. This may result in an increased incorporation of dUTP into daughter DNA fragments. The uracil bases may be excised. As the dUTP concentration increases over the course of a reaction, the reaction products may become shorter and thus available for barcoding. The dCTP aminase activity may be modified by adjusting the reaction parameters. For instance, the dCTP aminase activity may be modified by altering the reaction temperature, pH, dCTP concentration, inorganic phosphate concentration, and/or dTTP concentration. The dUTP concentration may also be modified by the production of dUTP in the reaction mixture. For instance, the reaction may be supplied with deoxycytidine monophosphate (dCMP) or deoxycytidine diphosphate (dCDP). A deaminase and/or kinase may then act upon the dCMP or dCDP to produce dUTP.

In some cases, a plurality of targeted constructs comprising a barcode sequence and a targeted N-mer comprising a poly-T sequence may be coupled to a bead (e.g., a gel bead). In some cases, the plurality of constructs may comprise an identical barcode sequence. The beads may be partitioned (e.g., in fluidic droplets) with sample nucleic acid comprising RNA, the bead(s) in each partition degraded to release the coupled constructs into the partition, and the sample RNA captured via the targeted N-mer of the constructs. Partitions may also comprise barcode constructs (e.g., with barcode sequences identical to the targeted constructs) that comprise a random N-mer. In a first amplification cycle, extension of the targeted constructs can occur via reverse transcription within each partition, to generate extension products comprising the targeted construct. The extension products in each partition can then be primed with the barcode constructs comprising the random N-mer to generate partial hairpin amplicons as described above. Post processing (e.g., addition of additional sequences (e.g., P7, R2), addition of a sample index, etc.) of the generated amplicons may be achieved with any method described herein, including bulk amplification methods (e.g., bulk PCR) and bulk ligation.

In some cases, reverse transcription of RNA in a sample may also be used without the use of a targeted barcode construct. For example, sample nucleic acid comprising RNA may be first subject to a reverse transcription reaction with other types of reverse transcription primers such that cDNA is generated from the RNA. The cDNA that is generated may then undergo targeted or non-targeted amplification as described herein. For example, sample nucleic acid comprising RNA may be subject to a reverse transcription reaction such that cDNA is generated from the RNA. The cDNA may then enter a PHASE amplification reaction, using a barcode construct with a random N-mer as described above, to generate partial hairpin amplicons comprising the construct's barcode sequence. Post processing (e.g., addition of additional sequences (e.g., P7, R2), addition of a sample index, etc.) of the generated partial hairpin amplicons may be achieved with any method described herein, including bulk amplification methods (e.g., bulk PCR) and bulk ligation.

Targeted barcode constructs may also be generated toward specific sequences (e.g., gene sequences) on specific strands of a nucleic acid such that strandedness information is retained for sequencer-ready products generated for each strand. For example, a sample nucleic may comprise double stranded nucleic acid (e.g., double-stranded DNA), such that each strand of nucleic acid comprises one or more different target gene sequences. Complementary DNA strands can comprise different gene sequences due to the opposite 5' to 3' directionalities and/or base composition of each strand. Targeted barcode constructs can be generated for each strand (based on 5' to 3' directionality of the strand) based on the targeted N-mer and configuration of the barcode construct.

A first and second set of targeted barcode constructs may be targeted to either of a forward strand and reverse strand of a double-stranded sample nucleic acid. The first set can comprise targeted barcode constructs comprising a P5 sequence, a barcode sequence, and a targeted N-mer to either of a first target sequence or a second target sequence. The second set can comprise targeted barcode constructs comprising a P5 sequence, a barcode sequence, and a targeted N-mer to either of the first target sequence and the second target sequence. Each construct can also comprise any additional sequences between the barcode and the targeted N-mer.

The barcode constructs in the first set can be configured to prime their respective target sequences on the forward strand of the double-stranded sample nucleic acid. The barcode constructs of the second set can be configured to prime their respective target sequences on the reverse strand of the double-stranded sample nucleic acid. The targeted barcode constructs in each set can be configured in opposite directionality corresponding to the opposite directionality of forward and reverse strands of the double-stranded sample nucleic acid. Each barcode construct can prime its respective target sequence on its respective strand of sample nucleic acid to generate barcoded amplicons via an amplification reaction, such as any amplification reaction described herein.

Additional sequences can be added to barcoded amplicons using amplification methods described herein, including bulk amplification, bulk ligation, or a combination thereof. A first primer set corresponds to the first targeted barcode construct set and a second primer set corresponds to the second targeted barcode construct set. Each primer can prime its respective target sequence on its respective strand and bulk amplification (e.g., bulk PCR) initiated to generate sequencer-ready constructs that include the P7 and sample index sequences in analogous fashion to bulk amplification methods described elsewhere herein. Based on the configuration and directionality of the various components of each sequencer-ready construct (e.g., P5, barcode, targeted N-mer, sample insert, etc.), the strand from which the sequencer-ready product is generated can be determined/is retained.

Methods described herein may be useful in whole genome amplification. In some embodiments of whole genome amplification, a random primer (e.g., a random N-mer sequence) can be hybridized to a genomic nucleic acid. The random primer can be a component of a larger oligonucleotide that may also include a universal nucleic acid sequence (including any type of universal nucleic acid sequence described herein) and a nucleic acid barcode sequence. In some cases, the universal nucleic acid sequence may comprise one or more uracil containing nucleotides. Moreover, in some cases, the universal nucleic acid sequence may comprise a segment of at least 1, 2, 3, 4, 5, 6, 7, 8, 9, 10, 11, 12, 13, 14, 15, 16, 17, 18, 19, 20, or more nucleotides that do not comprise uracil. The random primer can be extended (e.g., in a primer extension reaction or any other suitable type of nucleic acid amplification reaction) to form an amplified product.

In some embodiments of whole genome amplification, a genomic component (e.g., a chromosome, genomic nucleic acid such as genomic DNA, a whole genome of an organism, or any other type of genomic component described herein) may be fragmented in a plurality of first fragments. The first fragments can be co-partitioned into a plurality of partitions with a plurality of oligonucleotides. The oligonucleotides in each of the partitions may comprise a primer sequence (including a type of primer sequence described elsewhere herein) and a common sequence (e.g., a barcode sequence). Primer sequences in each partition can then be annealed to a plurality of different regions of the first fragments within each partition. The primer sequences can then be extended along the first fragments to produce amplified first fragments within each partition of the plurality of partitions. The amplified first fragments within the partitions may comprise any suitable coverage (as described elsewhere herein) of the genomic component. In some cases, the amplified first fragments within the partitions may comprise at least 1× coverage, at least 2× coverage, at least 5× coverage, at least 10× coverage, at least 20× coverage, at least 40× coverage, or greater coverage of the genomic component.

In some examples, amplification is performed using methods disclosed in U.S. Patent Application Publication No. 2016/0257984, which is entirely incorporated herein by reference for all purposes. In some cases, amplification may be performed using a priming free amplification by polymerization at nick sites (such as the priming free polymerization methods disclosed in U.S. Patent Application Publication No. 2016/0257984, which is entirely incorporated herein by reference for all purposes). Sequencing libraries produced via priming free amplification may provide superior sequencing results when compared to conventional primer-based amplification library preparation approaches. For instance, the priming free amplification approach may result in more even sequencing coverage across a broad range of GC base content when compared to primer-based amplification results. Improved sequencing coverage evenness may be achieved in priming free amplification, resulting in a more Poissonian distribution when compared to the distributions achieved using primer-based amplification.

Figure 21:
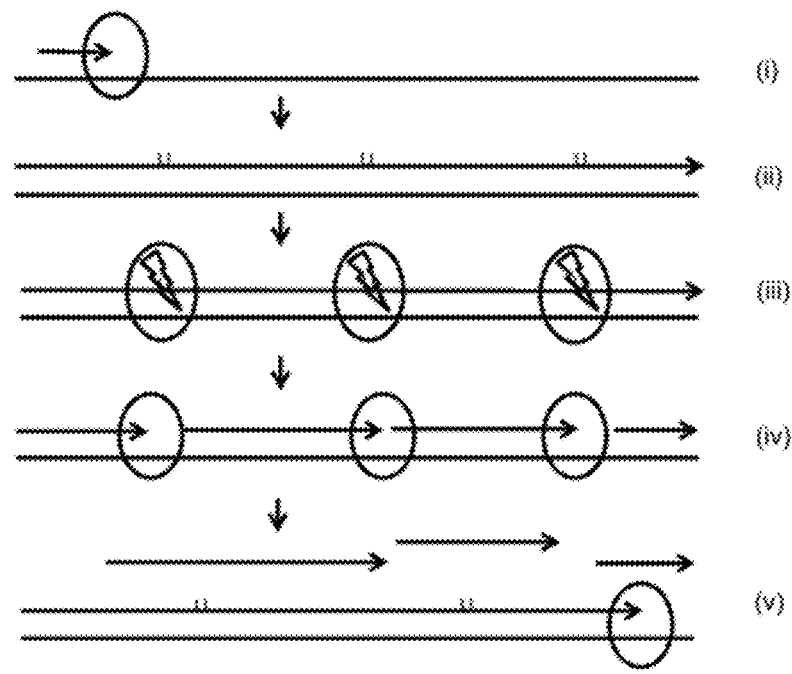
FIGS. 21(i)-21(v) illustrate an example process of library preparation using priming free amplification of templates.

FIG. 21 illustrates the process of library preparation using priming free amplification of templates. Although illustrated as a series of panels in FIG. 21, the reaction processes illustrated may be performed simultaneously with all the reagents present together in the reaction mixture during the priming free amplification by polymerization process. This process may be contrasted with a standard primed amplification process for preparing a sequencing library.

At (i) in FIG. 21, a DNA polymerase, such as phi29 DNA Polymerase (New England Biolabs® Inc. (NEB), Ipswich, Mass.), may be used to perform isothermal amplification. The isothermal amplification may comprise initiation using a hexamer (short arrow) and phi29 DNA polymerase (oval) which has very high processivity and fidelity that may result in even coverage and low error rates. As the polymerase processes along the target sequence (long line), a copied DNA template is produced. In the presence of all deoxyribonucleotide triphosphates (nucleotides) and a small amount of deoxyribouracil triphosphate, the polymerase based incorporation of dUTP results in a growing template strand (long arrow) at (ii) in FIG. 21. The reaction may include an enzyme (oval with bolt) capable of excising dUTP and creating nicks in the copied template DNA strand, but not in the original target sequence. At (iii) in FIG. 21, the nicking by the enzyme capable of excising dUTP may result in the production of a plurality of amplified strands (short arrows), each of which may be shorter than the original template strand. Additionally, phi29 DNA polymerase may engage at the nick sites for additional amplification in a priming independent amplification process. At (v) in FIG. 21, the original target sequence may be recycled as a template upon strand displacement of released amplified fragments owing to the highly processive nature of the phi29 DNA polymerase. Subsequent amplifications may mirror the previously described process to produce additional released amplified fragments.

Figure 22A:
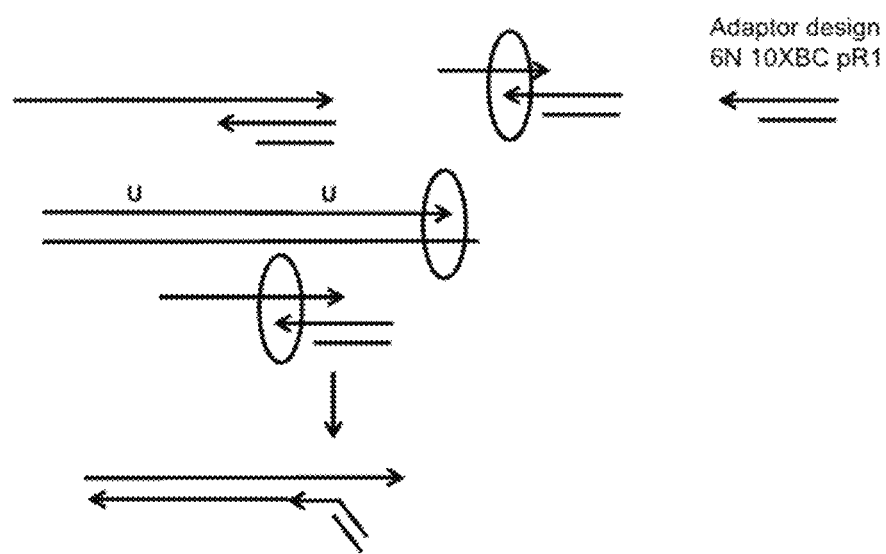
FIG. 22A shows an example method of barcoding amplified templates generated by priming free amplification using an extension barcoding approach.
Figure 22B:
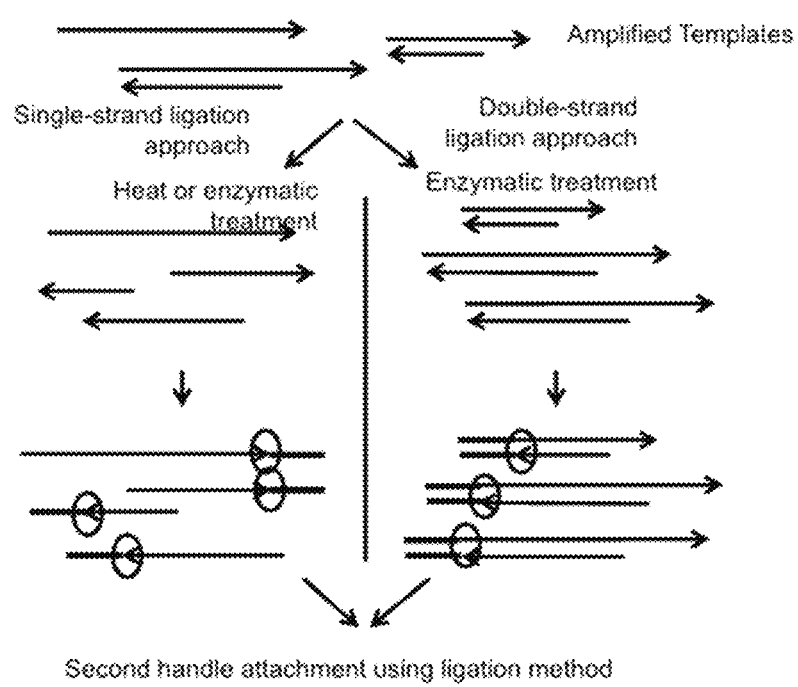
FIG. 22B shows an example method of barcoding amplified templates generated by priming free amplification using a single stranded or double stranded template to barcode ligation approach.
Figure 22C:
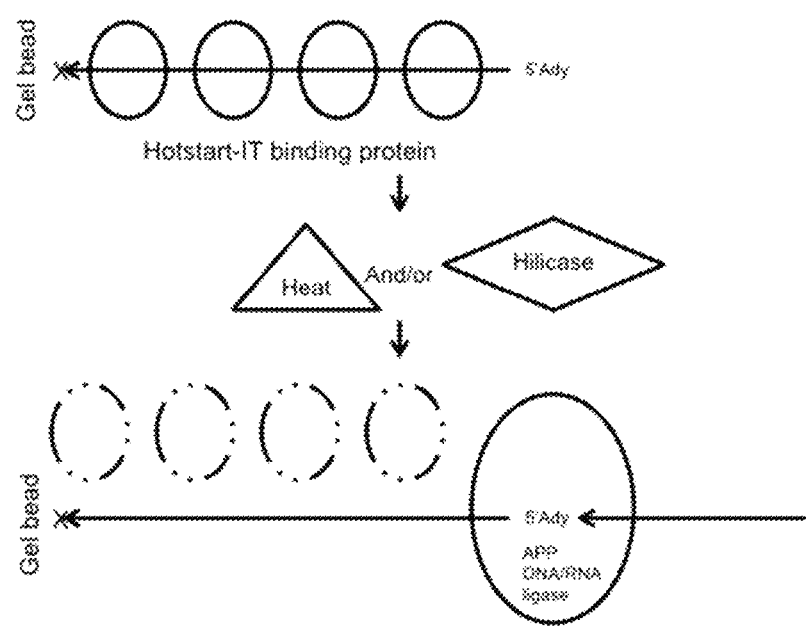
FIG. 22C shows an example method of barcoding amplified templates generated by the priming free amplification by attaching a single strand DNA molecule (with barcode or primer sequence) to a bead from the 3' end.

The priming free amplification methods may be extended to provide a barcoding capability, for instance as shown in FIGS. 22A-C.

FIG. 22A shows a method of barcoding amplified templates generated by the priming free amplification using an extension barcoding approach. Strand displacement and the high processivity of phi29 DNA polymerase may allow the release of amplified fragments, thereby enabling recycling of the template for further amplification. The single strand fragments that are generated during stand displacement may be converted to dsDNA by the hexamer or by the Nmer part of the same polymerase.

FIG. 22B shows a method of barcoding amplified templates generated by the priming free amplification using a single stranded or double stranded template to barcode ligation approach. The template DNA molecules may be converted to either single stranded (using, for instance, changes in temperature or an enzyme) or double stranded (using, for instance, an enzyme). The molecular barcodes, (such as oligonucleotides) may be attached through a ligation process using a ssDNA ligase, dsDNA ligase, or another nucleic acid modifying enzyme. Additional oligonucleotides serving as molecular handles may be added to the first barcode tag in subsequent ligations.

FIG. 22C shows a method of barcoding amplified templates generated by the priming free amplification by attaching a single strand DNA molecule (with barcode or primer sequence) to a bead from the 3' end. The 5' end of the oligo may be pre-adenylated (either chemically or enzymatically). The oligo may be sequestered using Hotstart-IT binding protein which may be released using heat. For barcoding the single-stranded library molecules (single strands generated by heat treatment or helicase), APP DNA/RNA ligase may ligate 5' pre-adenylated oligo with 3' end of the library molecule. This process may be very specific, as oligo-oligo ligation may be avoided by blocking the 3' end. Library molecules may be unable to self-ligate as they are not adenylated. The APP DNA/RNA ligase may be a thermostable 5' App DNA/RNA Ligase including a point mutant of catalytic lysine of RNA ligase from *Methanobacterium thermoautotrophicum*. This enzyme may be ATP independent. It may require a 5' pre-adenylated linker for ligation to the 3'-OH end of either RNA or single stranded DNA (ssDNA).

A further approach to molecular barcoding following the priming free amplification is the use of a topoisomerase enzyme. For instance, topoisomerase I from Vaccinia virus may bind to duplex DNA at specific sites and cleave the phosphodiester backbone after 5'-CCCTT in one strand. Molecular barcoding may be achieved when an adapter sequence (such as an oligonucleotide) is pre-bound to a topoisomerase enzyme. The amplified templates may be prepared for blunt end ligation using, for instance, the Klenow fragment of DNA polymerase.

In some cases, amplification may be performed using the degenerate oligonucleotide primed-polymerase chain reaction (DOP-PCR) method. DOP-PCR uses a partially degenerate sequence in a PCR protocol with two different annealing temperatures. The first PCR cycles are performed using a low annealing temperature. These cycles are then followed by a large number of PCR cycles with a higher annealing temperature. The use of the lower first annealing temperature may ensure that fragments that are specifically tagged in the first PCR cycles are amplified at the higher second annealing temperature. The DOP-PCR method may allow random amplification of DNA from any source.

In addition to the use of two annealing temperatures, DOP-PCR is characterized by the use of modified PCR primers. The DOP-PCR primer consists of three regions. The 5'-end carries a recognition sequence for XhoI (C.TC-GAG), a restriction endonuclease that cuts rarely within the human genome. The sequence is then followed by a middle portion containing six nucleotides of degenerate sequence (NNNNNN, where N=A, C, G, or T in approximately equal proportions) and a 3'-end sequence containing six specific bases (ATGTGG) which primes the reaction approximately every 4 kb. At a sufficiently low annealing temperature the six specific nucleotides included in the 3'-end of the degenerate oligonucleotide will anneal to the genomic strand allowing the primer to initiate PCR. The PCR fragments are then generated which contain the full length of the oligoprimer at one end and its complementary sequence at the other end. Subsequently, the temperature is increased to the level required for the full length of the degenerate primer to anneal.

In contrast to the pairs of target-specific primer sequences used in traditional PCR, a single primer, which has defined sequences at its 5'-end (containing an XhoI restriction site) and 3'-end and a random hexamer sequence between them, is used here. DOP-PCR comprises two different cycling stages. In the first low stringency phase, low-temperature annealing and extension in the first five to eight cycles occurs at many binding sites in the genome. The 3'-end of the primer binds at sites in the genome complementary to the 6-bp well-defined sequence at the 3'-end of the primer (~10(6) sites in the human genome). The adjacent random hexamer sequence (displaying all possible combinations of the nucleotides A, G, C, and T) can then anneal and tags these sequences with the DOP primer. In the second stage, the PCR annealing temperature is raised, which increases priming specificity during amplification of the tagged sequence.

Additional examples of the DOP-PCR method are provided, for example, in Arneson et al, Whole-genome amplification by degenerate oligonucleotide primed PCR (DOP-PCR), CSH Protoc DOI: 10.1101/pdb.prot4919 (Published Jan. 1, 2008), which is entirely incorporated herein by reference for all purposes.

Although operations with various barcode designs have been discussed individually, individual beads can include barcode oligonucleotides of various designs for simultaneous use.

In addition to characterizing individual cells or viruses or cell or virus sub-populations from larger populations, the processes and systems described herein may also be used to characterize individual cells or viruses as a way to provide an overall profile of a cellular, or other organismal population. A variety of applications require the evaluation of the presence and quantification of different cells or viruses or organism types within a population of cells or viruses, including, for example, microbiome analysis and characterization, environmental testing, food safety testing, epidemiological analysis, e.g., in tracing contamination or the like. In particular, the analysis processes described above may be used to individually characterize, sequence and/or identify large numbers of individual cells or viruses within a population. This characterization may then be used to assemble an overall profile of the originating population, which can provide important prognostic and diagnostic information.

For example, shifts in human microbiomes, including, e.g., gut, buccal, epidermal microbiomes, etc., have been identified as being both diagnostic and prognostic of different conditions or general states of health. Using the cell bead analysis methods and systems described herein, one can again, characterize, sequence and identify individual cells in an overall population, and identify shifts within that population that may be indicative of diagnostic ally relevant factors. By way of example, sequencing of bacterial 16S ribosomal RNA genes has been used as a highly accurate method for taxonomic classification of bacteria. Using the targeted amplification and sequencing processes described above can provide identification of individual cells within a population of cells. One may further quantify the numbers of different cells within a population to identify current states or shifts in states over time. See, e.g., Morgan et al, PLoS Comput. Biol., Ch. 12, December 2012, 8(12):e1002808, and Ram et al., Syst. Biol. Reprod. Med., June 2011, 57(3):162-170, each of which is entirely incorporated herein by reference for all purposes. Likewise, identification and diagnosis of infection or potential infection may also benefit from the cell bead analyses described herein, e.g., to identify microbial species present in large mixes of other cells and/or nucleic acids, from any diagnostically relevant environment, e.g., cerebrospinal fluid, blood, fecal or intestinal samples, or the like.

The foregoing analyses may also be particularly useful in the characterization of potential drug resistance of different cells or pathogens, e.g., cancer cells, bacterial pathogens, etc., through the analysis of distribution and profiling of different resistance markers/mutations across cell populations in a given sample. Additionally, characterization of shifts in these markers/mutations across populations of cells over time can provide valuable insight into the progression, alteration, prevention, and treatment of a variety of diseases characterized by such drug resistance issues.

Similarly, analysis of different environmental samples to profile the microbial organisms, viruses, or other biological contaminants that are present within such samples, can provide important information about disease epidemiology, and potentially aid in forecasting disease outbreaks, epidemics an pandemics.

As described above, the methods, systems and compositions described herein may also be used for analysis and characterization of other aspects of individual cells or viruses or populations of cells or viruses. In an example process, a sample is provided that contains cells associated with cell beads that are to be analyzed and characterized as to their cell surface proteins. Also provided is a library of antibodies, antibody fragments, or other molecules having a binding affinity to the cell surface proteins or antigens (or other cell features) for which the cell is to be characterized (also referred to herein as cell surface feature binding groups). For ease of discussion, these affinity groups are referred to herein as binding groups. The binding groups can include a reporter molecule that is indicative of the cell surface feature to which the binding group binds. In particular, a binding group type that is specific to one type of cell surface feature will comprise a first reporter molecule, while a binding group type that is specific to a different cell surface feature will have a different reporter molecule associated with it. In some aspects, these reporter molecules will comprise oligonucleotide sequences. Oligonucleotide based reporter molecules can provide advantages of being able to generate significant diversity in terms of sequence, while also being readily attachable to most biomolecules, e.g., antibodies, etc., as well as being readily detected, e.g., using sequencing or array technologies. In the example process, the binding groups include oligonucleotides attached to them. Thus, a first binding group type, e.g., antibodies to a first type of cell surface feature, will have associated with it a reporter oligonucleotide that has a first nucleotide sequence. Different binding group types, e.g., antibodies having binding affinity for other, different cell surface features, will have associated therewith reporter oligonucleotides that comprise different nucleotide sequences, e.g., having a partially or completely different nucleotide sequence. In some cases, for each type of cell surface feature binding group, e.g., antibody or antibody fragment, the reporter oligonucleotide sequence may be known and readily identifiable as being associated with the known cell surface feature binding group. These oligonucleotides may be directly coupled to the binding group, or they may be attached to a bead, molecular lattice, e.g., a linear, globular, cross-slinked, or other polymer, or other framework that is attached or otherwise associated with the binding group, which allows attachment of multiple reporter oligonucleotides to a single binding group.

In the case of multiple reporter molecules coupled to a single binding group, such reporter molecules can comprise the same sequence, or a particular binding group will include a known set of reporter oligonucleotide sequences. As between different binding groups, e.g., specific for different cell surface features, the reporter molecules can be different and attributable to the particular binding group.

Attachment of the reporter groups to the binding groups may be achieved through any of a variety of direct or indirect, covalent or non-covalent associations or attachments. For example, in the case of oligonucleotide reporter groups associated with antibody based binding groups, such oligonucleotides may be covalently attached to a portion of an antibody or antibody fragment using chemical conjugation techniques (e.g., Lightning-Link® antibody labeling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available (See, e.g., Fang, et al., *Fluoride-Cleavable Biotinylation Phosphoramidite for 5'-end-Labeling and Affinity Purification of Synthetic Oligonucleotides*, Nucleic Acids Res. Jan. 15, 2003; 31(2):708-715, DNA 3' End Biotinylation Kit, available from Thermo Scientific, which is entirely incorporated herein by reference for all purposes). Likewise, protein and peptide biotinylation techniques have been developed and are readily available (See, e.g., U.S. Pat. No. 6,265,552, which is entirely incorporated herein by reference for all purposes).

The reporter oligonucleotides may be provided having any of a range of different lengths, depending upon the diversity of reporter molecules or a given analysis, the sequence detection scheme employed, and the like. In some cases, these reporter sequences can be greater than about 5 nucleotides in length, greater than or equal to about 10 nucleotides in length, greater than or equal to about 20, 30, 40, 50, 60, 70, 80, 90, 100, 120, 150 or 200 nucleotides in length. In some cases, these reporter nucleotides may be less than about 250 nucleotides in length, less than or equal to about 200, 180, 150, 120 100, 90, 80, 70, 60, 50, 40, or 30 nucleotides in length. In many cases, the reporter oligonucleotides may be selected to provide barcoded products that are already sized, and otherwise configured to be analyzed on a sequencing system. For example, these sequences may be provided at a length that ideally creates sequenceable products of a length for particular sequencing systems. Likewise, these reporter oligonucleotides may include additional sequence elements, in addition to the reporter sequence, such as sequencer attachment sequences, sequencing primer sequences, amplification primer sequences, or the complements to any of these.

In operation, a cell-containing sample is incubated with the binding molecules and their associated reporter oligonucleotides, for any of the cell surface features to be analyzed. Following incubation, the cells are washed to remove unbound binding groups. Following washing, the cells (or components) are encapsulated into cell beads and the cell beads partitioned into separate partitions, e.g., droplets, along with the barcode carrying beads described above, where each partition includes a limited number of cells, e.g., in some cases, a single cell. Upon releasing the barcodes from the beads and the cell or cell components from the cell beads, they will prime the amplification and barcoding of the reporter oligonucleotides. As noted above, the barcoded replicates of the reporter molecules may additionally include functional sequences, such as primer sequences, attachment sequences or the like.

The barcoded reporter oligonucleotides are then subjected to sequence analysis to identify which reporter oligonucleotides bound to the cells within the partitions. Further, by also sequencing the associated barcode sequence, one can identify that a given cell surface feature likely came from the same cell as other, different cell surface features, whose reporter sequences include the same barcode sequence, i.e., they were derived from the same partition.

Based upon the reporter molecules that emanate from an individual partition based upon the presence of the barcode sequence, one may then create a cell surface profile of individual cells from a population of cells. Profiles of individual cells or populations of cells may be compared to profiles from other cells, e.g., 'normal' cells, to identify variations in cell surface features, which may provide diagnostically relevant information. In particular, these profiles may be particularly useful in the diagnosis of a variety of disorders that are characterized by variations in cell surface receptors, such as cancer and other disorders.

In one application, the methods and systems described herein may be used to characterize cell or virus features, such as cell surface features, e.g., proteins, receptors, etc. In particular, the methods described herein may be used to attach reporter molecules to these cell features, that when partitioned as described above, may be barcoded and analyzed, e.g., using DNA sequencing technologies, to ascertain the presence, and in some cases, relative abundance or quantity of such cell or virus features within an individual cell or virus or population of cells or viruses.

In a particular example, a library of potential cell binding ligands, e.g., antibodies, antibody fragments, cell surface receptor binding molecules, or the like, maybe provided associated with a first set of nucleic acid reporter molecules, e.g., where a different reporter oligonucleotide sequence is associated with a specific ligand, and therefore capable of binding to a specific cell surface feature. In some aspects, different members of the library may be characterized by the presence of a different oligonucleotide sequence label, e.g., an antibody to a first type of cell surface protein or receptor may have associated with it a first known reporter oligonucleotide sequence, while an antibody to a second receptor protein may have a different known reporter oligonucleotide sequence associated with it. Prior to co-partitioning, the cells may be incubated with the library of ligands, that may represent antibodies to a broad panel of different cell surface features, e.g., receptors, proteins, etc., and which include their associated reporter oligonucleotides. Unbound ligands are washed from the cells, and the cells are then co-partitioned along with the barcode oligonucleotides described above. As a result, the partitions will include the cell or cells, as well as the bound ligands and their known, associated reporter oligonucleotides.

One may then subject the reporter oligonucleotides to the barcoding operations described above for cellular nucleic acids, to produce barcoded, reporter oligonucleotides, where the presence of the reporter oligonucleotides can be indicative of the presence of the particular cell surface feature, and the barcode sequence will allow the attribution of the range of different cell surface features to a given individual cell or population of cells based upon the barcode sequence that was co-partitioned with that cell or population of cells. As a result, one may generate a cell-by-cell profile of the cell surface features within a broader population of cells. This aspect of the methods and systems described herein is described in greater detail below.

Figure 5:
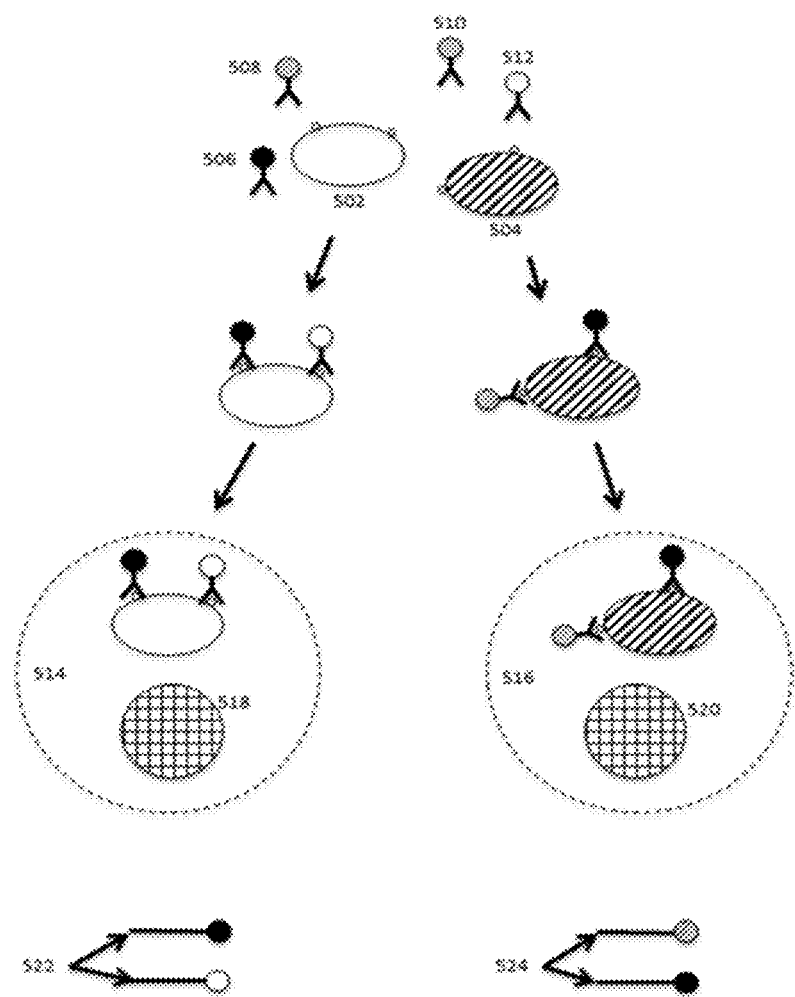
FIG. 5 provides a schematic illustration of cells associated with labeled cell-binding ligands.

This example is schematically illustrated in FIG. 5. As shown, a population of cells, represented by cells or cell components 502 and 504 are incubated with a library of cell surface associated reagents, e.g., antibodies, cell surface binding proteins, ligands or the like, where each different type of binding group includes an associated nucleic acid reporter molecule associated with it, shown as ligands and associated reporter molecules 506, 508, 510 and 512 (with the reporter molecules being indicated by the differently shaded circles). Where the cell expresses the surface features that are bound by the library, the ligands and their associated reporter molecules can become associated or coupled with the cell surface. Individual cells are encapsulated into cell beads, in some cases subject to lysis and/or denaturing conditions, and the resulting cell beads are then partitioned into separate partitions, e.g., droplets 514 and 516, along with their associated ligand/reporter molecules, as well as an individual barcode oligonucleotide bead as described elsewhere herein, e.g., beads 522 and 524, respectively. The cellular material is released from the cell beads and the barcoded oligonucleotides are released from the beads and used to attach the barcode sequence the reporter molecules present within each partition with a barcode that is common to a given partition, but which varies widely among different partitions. For example, as shown in FIG. 5, the reporter molecules that associate with cell or cell components 502 in partition 514 are barcoded with barcode sequence 518, while the reporter molecules associated with cell or cell components 504 in partition 516 are barcoded with barcode 520. As a result, one is provided with a library of oligonucleotides that reflects the surface ligands of the cell, as reflected by the reporter molecule, but which is substantially attributable to an individual cell by virtue of a common barcode sequence, allowing a single cell level profiling of the surface characteristics of the cell. This process is not limited to cell surface receptors but may be used to identify the presence of a wide variety of specific cell structures, chemistries or other characteristics. Cell bead processing and analysis methods and systems described herein can be utilized for a wide variety of applications, including analysis of specific individual cells, analysis of different cell types within populations of differing cell types, analysis and characterization of large populations of cells for environmental, human health, epidemiological forensic, or any of a wide variety of different applications.

Cells may be treated with cell surface associated reagents prior to being processed such that the cells or components of the cells are encapsulated within cell beads. Upon partitioning of cell beads with barcoded beads as described elsewhere herein, barcodes from the barcode beads can be used to generate barcoded constructs derived from reporter molecules associated with cell surface associated reagents.

Also provided herein are kits for analyzing individual cells or viruses or small populations of cells or viruses. The kits may include one, two, three, four, five or more, up to all of partitioning fluids, including both aqueous buffers and non-aqueous partitioning fluids or oils, nucleic acid barcode libraries that are releasably associated with beads, as described herein, microfluidic devices, reagents for disrupting cells amplifying nucleic acids, and providing additional functional sequences on fragments of cellular nucleic acids or replicates thereof, as well as instructions for using any of the foregoing in the methods described herein.

In encapsulating single cell beads and single barcode beads within a droplet, it may be useful to utilize methods and systems which allow one or more chemical or biochemical operations enacted on the encapsulated material of the single cell bead to proceed to completion prior to allowing the encapsulated material to interact with the barcodes of the barcode bead. For instance, chemicals used in preparing a cell for barcoding may be chemically incompatible with the beads or barcodes themselves. As an example, prior to or contemporaneous to co-partitioning cell beads and barcode beads, lysis agents (which, may, for example, degrade barcodes), such as sodium hydroxide (NaOH), may be used to lyse a cell encapsulated in a cell bead in order to allow the macromolecular constituents of the encapsulated be released for later interaction with the bead and its barcodes.

Furthermore, reagents may be used to perform one or more additional chemical or biochemical operation following lysis of a cell encapsulated in a cell bead. Reagents may include any reagents useful in performing an operation (e.g., a reaction), such as, for example, nucleic acid modification (e.g., ligation, digestion, methylation, random mutagenesis, bisulfite conversion, uracil hydrolysis, nucleic acid repair, capping, or decapping), nucleic acid amplification (e.g., isothermal amplification or PCR), nucleic acid insertion or cleavage (e.g., via CRISPR/Cas9-mediated or transposon-mediated insertion or cleavage), or reverse transcription. Additionally, it may be useful to utilize methods and systems that allow the preparation of target sequence or sequencing reads specific to macromolecular constituents of interest at a higher rate than non-target specific reads. For instance, the methods and systems may be characterized by their suppression of no template control (NTC) effects.

The systems and methods described herein may allow for the production of one or more droplets containing a single cell bead and a single barcode bead. The systems and methods may also allow for the production of one or more droplets containing a single cell bead and more than barcode one bead, one or more droplets containing more than one cell bead and a single barcode bead, or one or more droplets containing more than one cell bead and more than one barcode bead.

Figure 7:
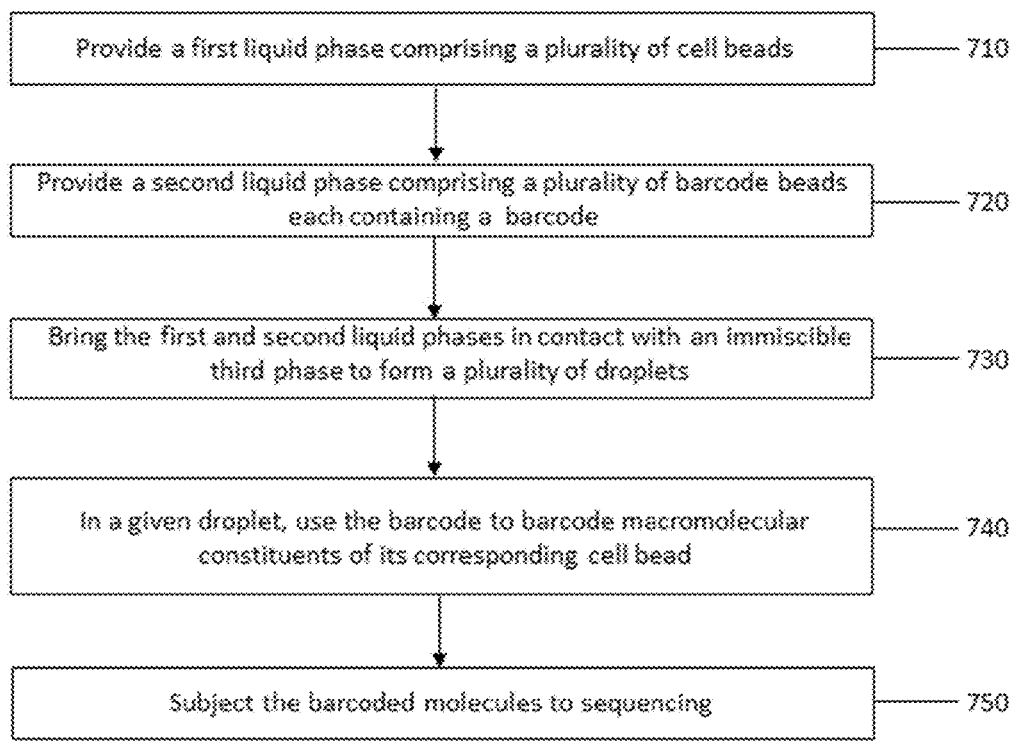
FIG. 7 shows a flowchart for a method of producing droplets containing a cell bead and a barcode bead and generating sequence reads from macromolecular components of the cell bead.

FIG. 7 shows a flowchart for a method 700 of producing droplets containing a cell bead and a barcode bead (e.g., gel bead) comprising a barcode sequence and generating sequence reads from macromolecular components of the cell bead.

In operation 710, a first liquid phase comprising a plurality of cell beads is provided. The first liquid phase may be aqueous. The first liquid phase may comprise a cellular growth medium. The first liquid phase may comprise a minimal growth medium.

In operation 720, a second liquid phase comprising a plurality of barcode beads can be provided. The second liquid phase may be aqueous. The second liquid phase may comprise a cellular growth medium. The second liquid phase may comprise a minimal growth medium. The barcode beads each contain a barcode to barcode one or more macromolecular constituents of the plurality of cell beads. In some cases, the first liquid phase and the second liquid phase are the same phase. In some cases, the first liquid phase and the second liquid phase are mixed to provide a mixed phase.

In operation 730, the first liquid phase and the second liquid phase can be brought together with a third liquid phase that is immiscible with the first and second liquid phase. The third liquid phase may interact with the first and second liquid phases in such a manner as to partition each of the plurality of cell beads and the plurality of barcode beads into a plurality of droplets. The third liquid phase may comprise an oil. The third liquid phase may comprise a fluorinated hydrocarbon. In some cases, a given droplet may include a single cell bead and a single barcode bead. In some cases, at least 80%, at least 90%, at least 95%, at least 99%, at least 99.5%, at least 99.9%, at least 99.95%, or at least 99.99% of the droplets may contain a single cell bead. Moreover, while the first liquid phase and second liquid phase are partitioned into droplets in this example, other types of partitions can be implemented at operation 730, including those described elsewhere herein, such as a well.

In operation 740, the barcode can be used to barcode one or more macromolecular constituents of a given cell bead in a given droplet. In some cases, the macromolecular constituents of the cell bead are subjected to conditions sufficient for nucleic acid amplification for barcoding. In such cases, a barcode can function as a primer in such amplification. In other cases, ligation can be used for barcoding. In some cases, the macromolecular constituents are released from the cell bead prior to amplification. In some cases, the barcode is used to identify one or more macromolecular constituents of the cell bead. In some cases, a barcoded macromolecule is subjected to nucleic acid sequencing to identify one or more macromolecular components. In some cases, the sequencing is untargeted sequencing. In some cases, the sequencing is targeted sequencing. In some cases, droplets comprise an agent that can release the macromolecular constituents from the cell bead during or prior to barcoding. In some cases, a given barcoded sequencing read can be used to identify the cell (which may have been encapsulated in a cell bead) from which the barcoded sequencing read was generated. Such capability can link particular sequences to particular cells.

In operation 750, the barcoded macromolecules (or derivatives thereof) can be subjected to sequencing to generate reads. The sequencing may be performed within a droplet (or partition). The sequencing may be performed outside of a droplet. For instance, the sequencing may be performed by releasing the barcoded macromolecules from a droplet (e.g., by breaking an emulsion comprising the droplets) and sequencing the barcoded macromolecules using a sequencer, such as an Illumina sequencer or any other sequencer described herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

In some cases, the sequencing is nucleic acid sequencing. In some cases, the nucleic acid sequencing is massively parallel sequencing. In some cases, the nucleic acid sequencing is digital polymerase chain reaction (PCR) sequencing. The sequencing may produce target specific reads from macromolecular constituents of interest from a cell bead and non-target specific reads of other macromolecular sequences. The target specific reads may correspond to one or more nucleic acid sequences from a cell bead. In some cases, the non-target specific reads may arise from macromolecules external to the cell bead. For instance, the non-target specific reads may correspond to one or more exogenous nucleic acid sequences. As another example, the non-target specific reads may arise from no-template control effects. The reads may be characterized by a target specific read to non-target specific read ratio. The target specific read to non-target specific read ratio may be greater than 5, greater than 10, greater than 100, greater than 1,000, greater than 10,000, greater than greater than 1,000,000, greater than greater than 10,000,000, greater than 100,000,000, or greater than 1,000,000,000.

Figure 8:
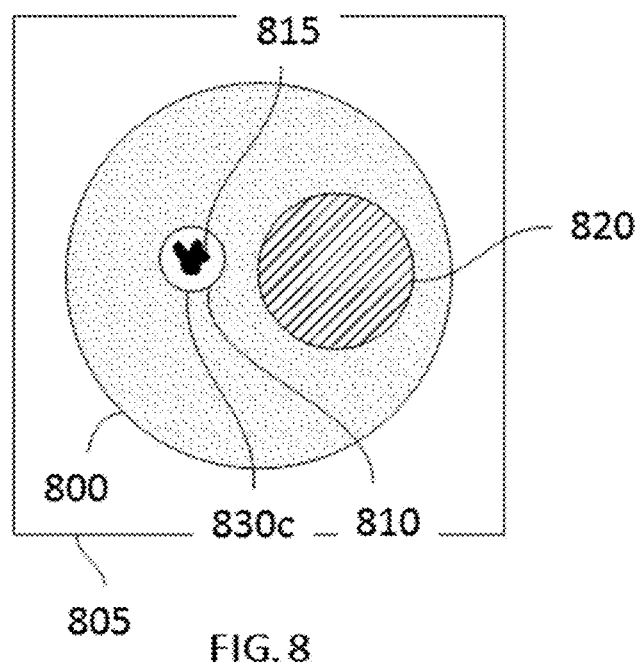
FIG. 8 shows a droplet containing a cell bead and a barcode bead produced using the method of FIG. 7.

FIG. 8 shows a droplet containing a cell bead and a barcode bead produced using the method 700. A droplet 800 of aqueous liquid is formed inside a volume 805 of a liquid that is immiscible with the aqueous liquid. The droplet contains a barcode bead 820. The droplet also contains a cell bead 810 having an outer surface 830c and containing one or more macromolecular constituents 815.

Figure 9:
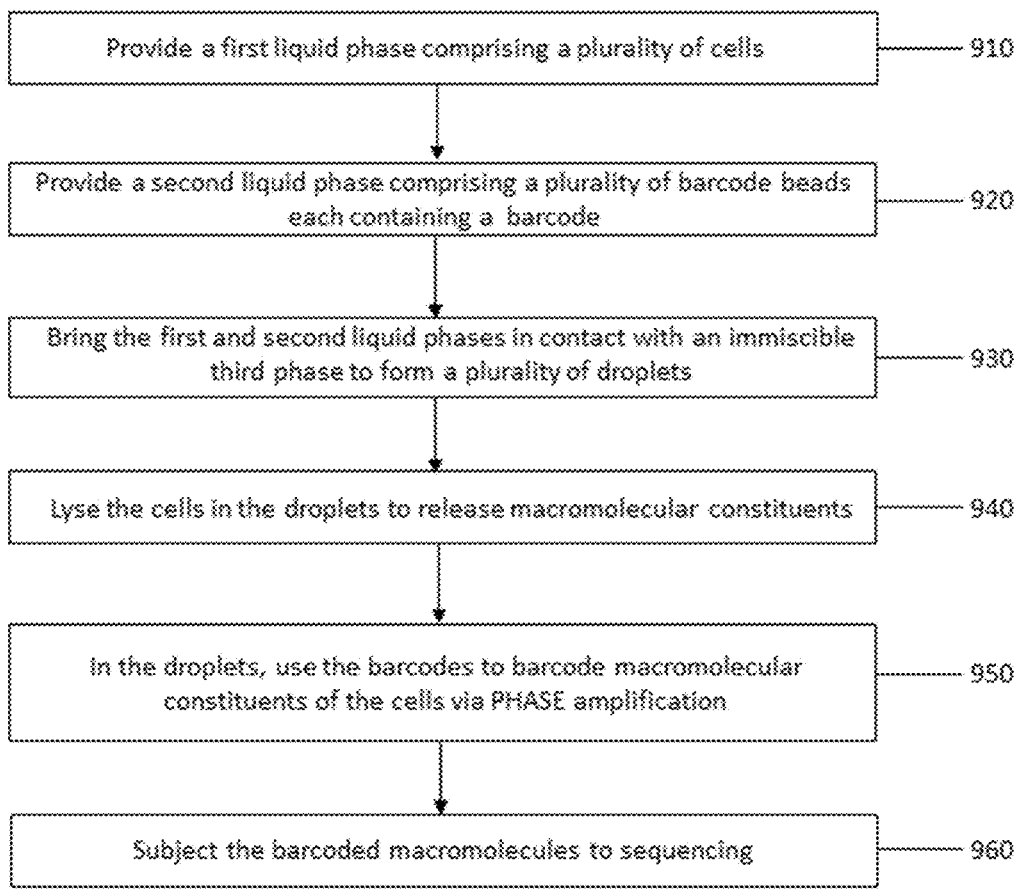
FIG. 9 shows a flowchart for a method of producing droplets containing a cell and a barcode bead and generating sequence reads from macromolecular components of the cell.

FIG. 9 shows a flowchart depicting an example method 900 of producing droplets containing a cell and a barcode bead (e.g., gel bead) comprising a barcode sequence and generating sequence reads from macromolecular components of the cell using the PHASE amplification technique described elsewhere herein. In some cases, the method 900 comprises the following operations.

In operation 910, a first liquid phase comprising a plurality of cells is provided. The first liquid phase may be aqueous. The first liquid phase may comprise a cellular growth medium. The first liquid phase may comprise a minimal growth medium.

In operation 920, a second liquid phase comprising a plurality of barcode beads can be provided. The second liquid phase may be aqueous. The second liquid phase may comprise a cellular growth medium. The second liquid phase may comprise a minimal growth medium. The barcode beads each contain a barcode to barcode one or more macromolecular constituents of the plurality of cells. In some cases, the first liquid phase and the second liquid phase are the same phase. In some cases, the first liquid phase and the second liquid phase are mixed to provide a mixed phase.

In operation 930, the first liquid phase and the second liquid phase can be brought together with a third liquid phase that is immiscible with the first and second liquid phase. The third liquid phase may interact with the first and second liquid phases in such a manner as to partition each of the plurality of cells and the plurality of barcode beads into a plurality of droplets. The third liquid phase may comprise an oil and may also comprise a surfactant. The third liquid phase may comprise a fluorinated hydrocarbon. In some cases, a given droplet may include a single cell and a single barcode bead. In some cases, at least 80%, at least 90%, at least 95%, at least 99%, at least 99.5%, at least 99.9%, at least 99.95%, or at least 99.99% of the droplets may contain a single cell. In operation 930, the first liquid phase and the second liquid phase are brought together with a third liquid phase that is immiscible with the first and second liquid phase. The third liquid phase may interact with the first and second liquid phases in such a manner as to partition each of the plurality of cells and the plurality of barcode beads into a plurality of droplets. The third liquid phase may comprise an oil. The third liquid phase may comprise a fluorinated hydrocarbon. In some cases, a given droplet may include a single cell and a single barcode bead. In some cases, at least 80%, at least 90%, at least 95%, at least 99%, at least 99.5%, at least 99.9%, at least 99.95%, or at least 99.99% of the droplets may contain a single cell. Moreover, while the first liquid phase and second liquid phase are partitioned into droplets in this example, other types of partitions can be implemented at operation 930, including those described elsewhere herein, such as a well.

In operation 940, the cell can be subject to lysis. Lysis may be completed as described elsewhere herein, including with a lysis agent. A lysis agent may be included within a droplet such that lysis occurs within the droplet. Lysis of the cell within the droplet can release macromolecular constituents from the cell for additional processing, such as barcoding.

In operation 950, the barcode can be used to barcode one or more macromolecular constituents of a given cell in a given droplet. Barcoding can be completed via PHASE amplification as described elsewhere herein. Barcode beads can comprise oligonucleotides having a barcode sequence and a primer sequence that hybridizes with macromolecular constituents released from cells. These oligonucleotides may be released from barcode beads, including within droplets. In some cases, the cell is subjected to conditions sufficient for nucleic acid amplification. In some cases, the barcode is used to identify one or more macromolecular constituents of the cell. In some cases, the barcode is subjected to nucleic acid sequencing to identify one or more macromolecular components. In some cases, the sequencing is untargeted sequencing. In some cases, the sequencing is targeted sequencing.

In operation 960, the barcoded macromolecules (or derivatives thereof) can be subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell from which the barcoded sequencing read was generated. Such capability can link particular sequences to particular cells. Additional details and examples regarding nucleic acid sequencing methods and the use of barcodes for identification are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 10:
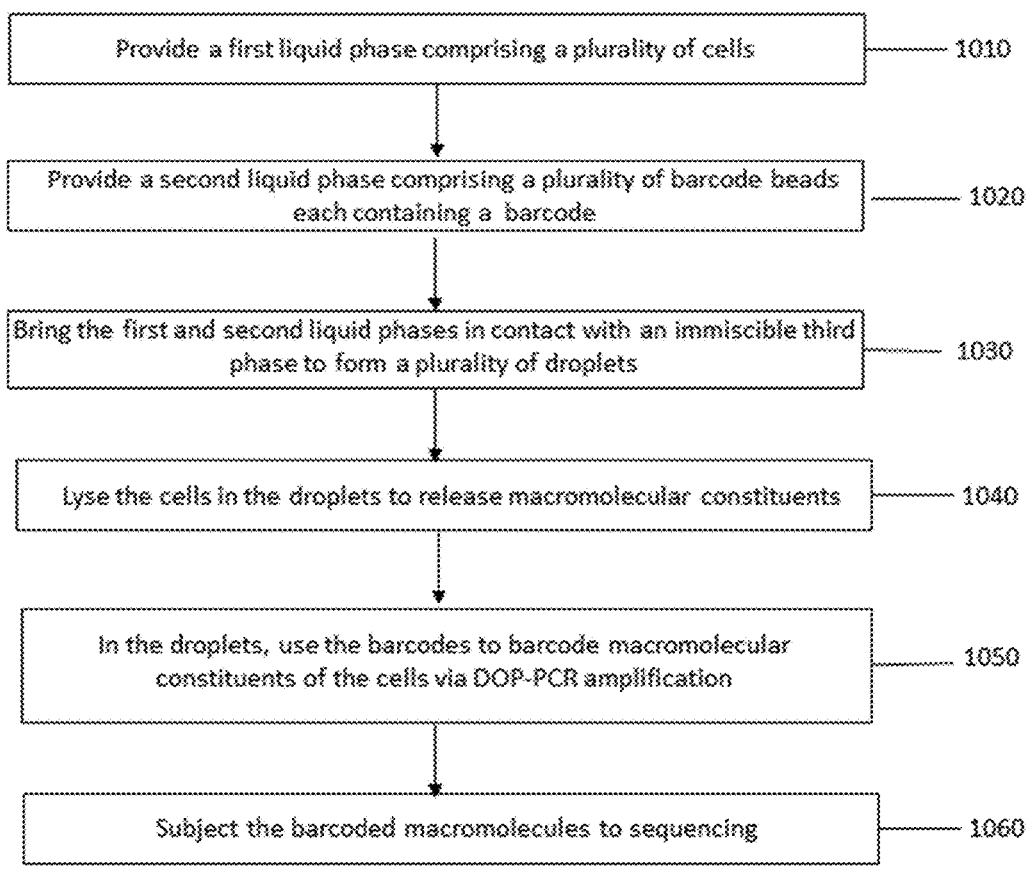
FIG. 10 shows a flowchart for a method of producing droplets containing a cell and a barcode bead and generating sequence reads from macromolecular components of the cell.

FIG. 10 shows a flowchart depicting an example method 1000 of producing droplets containing a cell and a barcode bead (e.g., gel bead) comprising a barcode sequence and generating sequence reads from macromolecular components of the cell using the degenerate-oligonucleotide-primed PCR (DOP-PCR) amplification technique described elsewhere herein. In some cases, the method 1000 comprises the following operations.

In operation 1010, a first liquid phase comprising a plurality of cells is provided. The first liquid phase may be aqueous. The first liquid phase may comprise a cellular growth medium. The first liquid phase may comprise a minimal growth medium.

In operation 1020, a second liquid phase comprising a plurality of barcode beads can be provided. The second liquid phase may be aqueous. The second liquid phase may comprise a cellular growth medium. The second liquid phase may comprise a minimal growth medium. The barcode beads each contain a barcode to barcode one or more macromolecular constituents of the plurality of cells. In some cases, the first liquid phase and the second liquid phase are the same phase. In some cases, the first liquid phase and the second liquid phase are mixed to provide a mixed phase.

In operation 1030, the first liquid phase and the second liquid phase can be brought together with a third liquid phase that is immiscible with the first and second liquid phase. The third liquid phase may interact with the first and second liquid phases in such a manner as to partition each of the plurality of cells and the plurality of barcode beads into a plurality of droplets. The third liquid phase may comprise an oil and may also comprise a surfactant. The third liquid phase may comprise a fluorinated hydrocarbon. In some cases, a given droplet may include a single cell and a single barcode bead. In some cases, at least 80%, at least 90%, at least 95%, at least 99%, at least 99.5%, at least 99.9%, at least 99.95%, or at least 99.99% of the droplets may contain a single cell. In operation 1030, the first liquid phase and the second liquid phase are brought together with a third liquid phase that is immiscible with the first and second liquid phase. The third liquid phase may interact with the first and second liquid phases in such a manner as to partition each of the plurality of cells and the plurality of barcode beads into a plurality of droplets. The third liquid phase may comprise an oil. The third liquid phase may comprise a fluorinated hydrocarbon. In some cases, a given droplet may include a single cell and a single barcode bead. In some cases, at least 80%, at least 90%, at least 95%, at least 99%, at least 99.5%, at least 99.9%, at least 99.95%, or at least 99.99% of the droplets may contain a single cell. Moreover, while the cells are partitioned into droplets in this example, other types of partitions can be implemented at operation 1030, including those described elsewhere herein, such as a well.

In operation 1040, the cell can be subjected to lysis. Lysis may be completed as described elsewhere herein, including with a lysis agent. A lysis agent may be included within a droplet such that lysis occurs within the droplet. Lysis of the cell within the droplet can release macromolecular constituents from the cell for additional process, such as barcoding.

In operation 1050, the barcode can be used to barcode one or more macromolecular constituents of a given cell in a given droplet. Barcoding can be completed via DOP-PCR amplification. Barcode beads can comprise oligonucleotides having a barcode sequence and a primer sequence that hybridizes with macromolecular constituents released from cells. These oligonucleotides may be released from beads, including within droplets. In some cases, the macromolecular constituents of the cell are subjected to conditions sufficient for nucleic acid amplification. In some cases, the barcode is used to identify one or more macromolecular constituents of the cell. In some cases, the barcode is subjected to nucleic acid sequencing to identify one or more macromolecular components. In some cases, the sequencing is untargeted sequencing. In some cases, the sequencing is targeted sequencing.

In operation 1060, the barcoded macromolecules (or derivatives thereof) can be subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell from which the barcoded sequencing read was generated. Such capability can link particular sequences to particular cells. Additional details and examples regarding nucleic acid sequencing methods and the use of barcodes for identification are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 11:
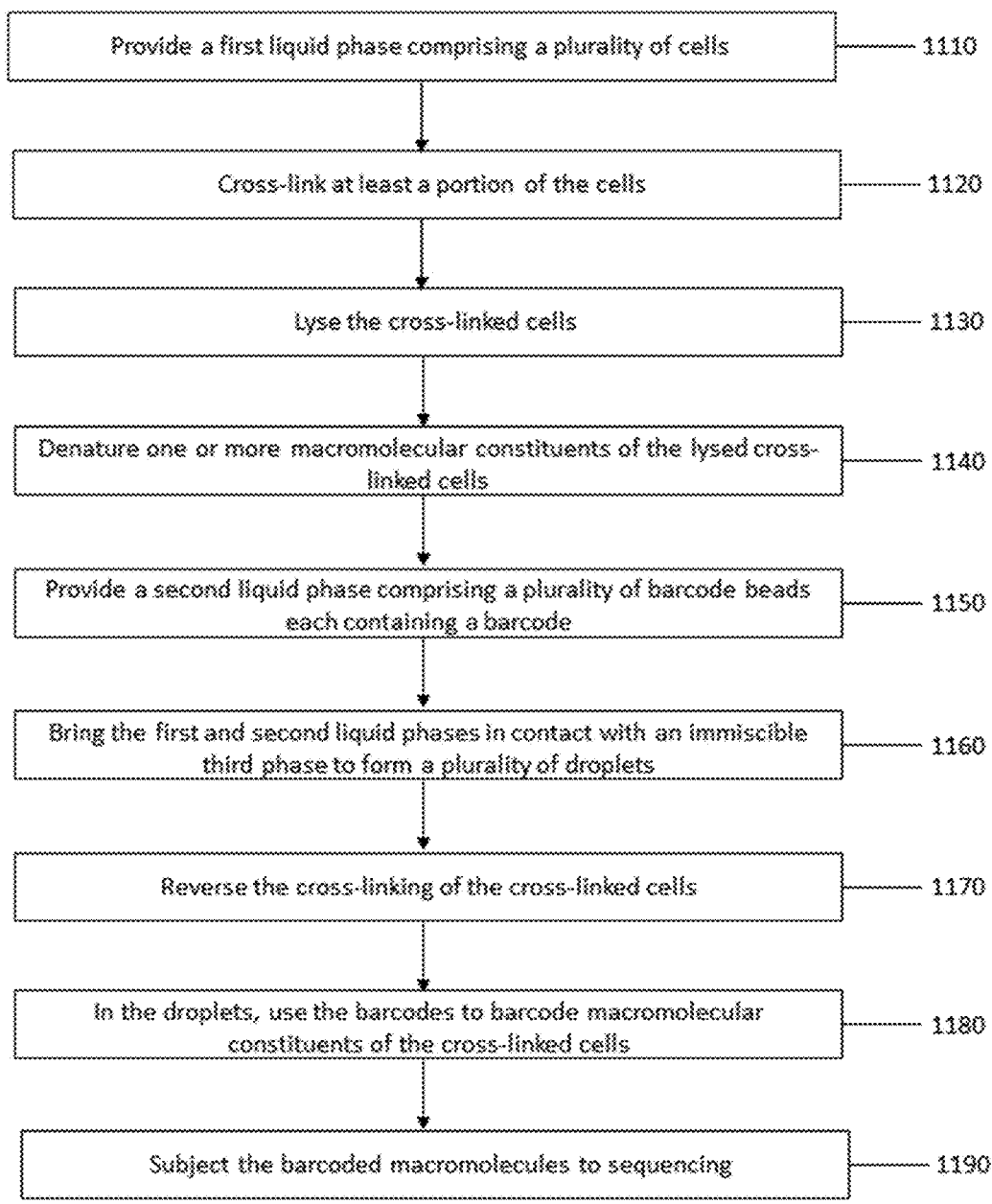
FIG. 11 shows a flowchart for a method of producing droplets containing a cross-linked cell and a barcode bead and generating sequence reads from macromolecular components the cross-linked cell.

FIG. 11 shows a flowchart depicting an example method 1100 of producing droplets containing a cell bead and a barcode bead (e.g., a gel bead) comprising a barcode sequence and generating sequence reads from macromolecular components of a the cell bead. The cell bead is generated by cross-linking of at least a portion of a cell. In some cases, the method 1100 may comprise the following operations.

In operation 1110, a first liquid phase comprising a plurality of cells is provided. The first liquid phase may be aqueous. The first liquid phase may comprise a cellular growth medium. The first liquid phase may comprise a minimal growth medium.

In operation 1120, the cells can be subjected to conditions sufficient to cross-link at least a portion of the cells. In some cases, the cells are subjected to conditions sufficient to cross-link at least a portion of a membrane. In some cases, the cells are subjected to conditions sufficient to cross-link the entirety of a membrane. The cross-linking may be achieved by exposing the cells to diothiobis(succinimidyl-propionate) (DSP). The cross-linking may be achieved by exposing the cells to any cross-linking agent. The cross-linked portion of the cells may be diffusively permeable to chemical or biochemical reagents. The cross-linked portion may be diffusively impermeable to macromolecular constituents of the cells. In this manner, the cross-linked portion may act to allow the cells to be subjected to chemical or biochemical operations while spatially confining the macromolecular constituents to a region of the droplet defined by the cross-linked portion.

In operation 1130, the cross-linked cells can be subjected to conditions sufficient to lyse the cross-linked cells. In some cases, lysis may be completed in a droplet, such as, for example, via a lysis agent in a droplet. The lysis of the cross-linked cells may occur subsequent to subjecting the cross-linked cells to conditions sufficient to cross-link the cells. In some cases, the lysis of the cross-linked cells may occur contemporaneously with subjecting the cells to conditions sufficient to cross-link the cells. In some cases, lysis may be completed in bulk with multiple cross-linked cells treated in one pot. The lysis may disrupt components of the cross-linked cell that aid in containing macromolecular constituents of the cells. However, the cross-linking of the cell may provide a barrier such that the "released" materials are still retained within the cross-linked cell. The lysis may be achieved by exposing the cross-linked cells to sodium hydroxide (NaOH), potassium hydroxide (KOH), or any other alkaline agent. The lysis may be achieved by exposing the cross-linked cells to a detergent, such as sodium dodecyl sulfate (SDS), 4-(1,1,3,3-Tetramethylbutyl)phenyl-polyethylene glycol (TRITON X-100) or any non-ionic surfactant, or a saponin. The lysis may be achieved by exposing the cross-linked cells to an enzyme, such as a proteinase or a lytic enzyme (such as a lysozyme, cellulose, or zymolase). The lysis may be achieved by exposing the cross-linked cells to freeze thawing. The lysis may be achieved by exposing the cross-linked cells to electromagnetic radiation, such as ultraviolet (UV) light. The lysis may be achieved by exposing the cross-linked cells to heat. The lysis may be achieved by exposing the cross-linked cells to any other lysis agent.

In operation 1140, the lysed, cross-linked cells can be subjected to conditions sufficient to denature one or more macromolecular constituents of the lysed, cross-linked cells. In some cases, denaturation is achieved in bulk, where more than one cross-linked cell is subjected to denaturation conditions in a single pot. The denaturing may be achieved by exposing the cross-linked cells to sodium hydroxide (NaOH). The denaturing may be achieved by exposing the cross-linked cells to any other denaturing agent. In some examples, operation 1140 is completed contemporaneous to operation 1130. In some examples, a denaturing agent can both denature macromolecular constituents and lyse the cross-linked cells.

In operation 1150, a second liquid phase comprising a plurality of barcode beads can be provided. The second liquid phase may be aqueous. The second liquid phase may comprise a cellular growth medium. The second liquid phase may comprise a minimal growth medium. The barcode beads each contain a barcode to barcode one or more macromolecular constituents of the plurality of cross-linked cells. In some cases, the first liquid phase and the second liquid phase are the same phase. In some cases, the first liquid phase and the second liquid phase are mixed to provide a mixed phase.

In operation 1160, the first liquid phase and the second liquid phase can be brought together with a third liquid phase that is immiscible with the first and second liquid phase. The third liquid phase may interact with the first and second liquid phases in such a manner as to partition each of the plurality of cross-linked cells and the plurality of barcode beads into a plurality of droplets. The third liquid phase may comprise an oil and may also comprise a surfactant. The third liquid phase may comprise a fluorinated hydrocarbon. In some cases, a given droplet may include a single cross-linked cell and a single barcode bead. In some cases, at least 80%, at least 90%, at least 95%, at least 99%, at least 99.5%, at least 99.9%, at least 99.95%, or at least 99.99% of the droplets may contain a single cross-linked cell. Moreover, while cross-linked cells are partitioned into droplets in this example, other types of partitions can be implemented at operation 1160, including those described elsewhere herein, such as a well.

In operation 1170, the cross-linked cells can be subjected to conditions sufficient to reverse the cross-linking. The reversal of the cross-linking may be achieved by exposing the cross-linked cells to a reducing agent (e.g., dithiothreitol (DTT)), which may be present in a droplet. The reversal of the cross-linking may be achieved by exposing the cross-linked cells to any substance capable of reversing cross-linking. Reversal of cross-linking can release the macromolecular constituents of the cross-linked cells to the interiors of the droplets. In some cases, operation 1170 also includes releasing barcodes from the barcode beads, which may be achieved with the same stimulus, such as, for example used to reverse cross-linking of the cells. In some cases, the stimuli are different. Released barcodes can then participate in barcoding as in operation 1180.

In operation 1180, the barcode can be used to barcode one or more macromolecular constituents of a given cross-linked cell in a given droplet. In some cases, the macromolecular constituents are subjected to conditions sufficient for nucleic acid amplification for barcoding. In such cases, the barcodes released from the barcode beads can function as primers in such amplification. In some cases, ligation is used for barcoding. In some cases, the barcode is used to identify one or more macromolecular constituents of the cross-linked cell. In some cases, the barcode is subjected to nucleic acid sequencing to identify one or more macromolecular components. In some cases, the sequencing is untargeted sequencing. In some cases, the sequencing is targeted sequencing.

In operation 1190, the barcoded macromolecules (or derivatives thereof) can be subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell (which may have been a cross-linked cell) from which the barcoded sequencing read was generated. Such capability can link particular sequences to particular cells. Additional details and examples regarding nucleic acid sequencing methods and the use of barcodes for identification are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 12:
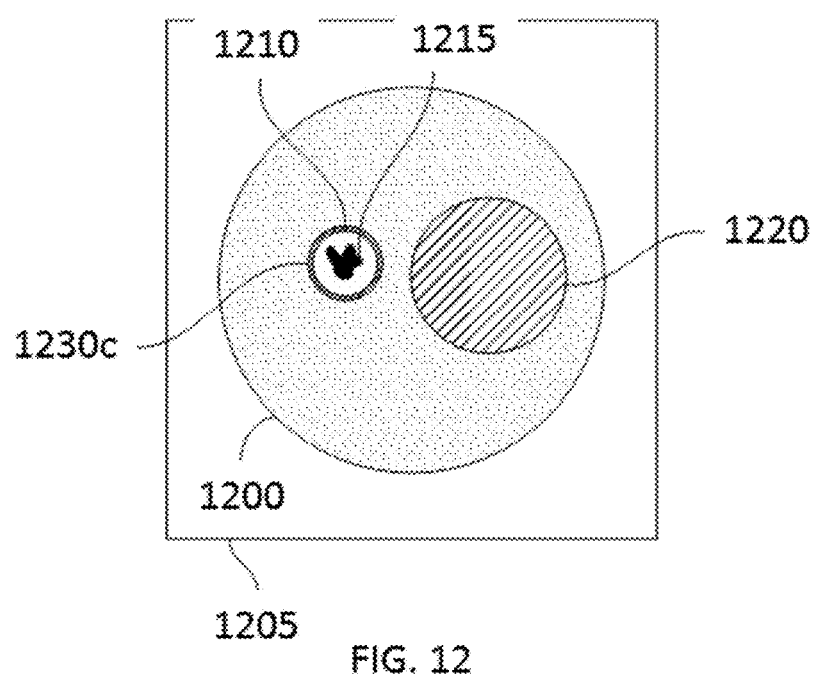
FIG. 12 shows a droplet containing a cross-linked cell and a barcode bead produced using the method of FIG. 11.

FIG. 12 shows a droplet containing a cross-linked cell and a barcode bead produced using the method 1100. A droplet 1200 of aqueous liquid is formed inside a volume 1205 of a liquid that is immiscible with the aqueous liquid. The droplet contains a single gel bead 1220. The droplet also contains a single cross-linked cell 1210 containing one or more macromolecular constituents 1215. A portion of the cross-linked cell is crosslinked to form a crosslinked outer portion 1230c.

Figure 13:
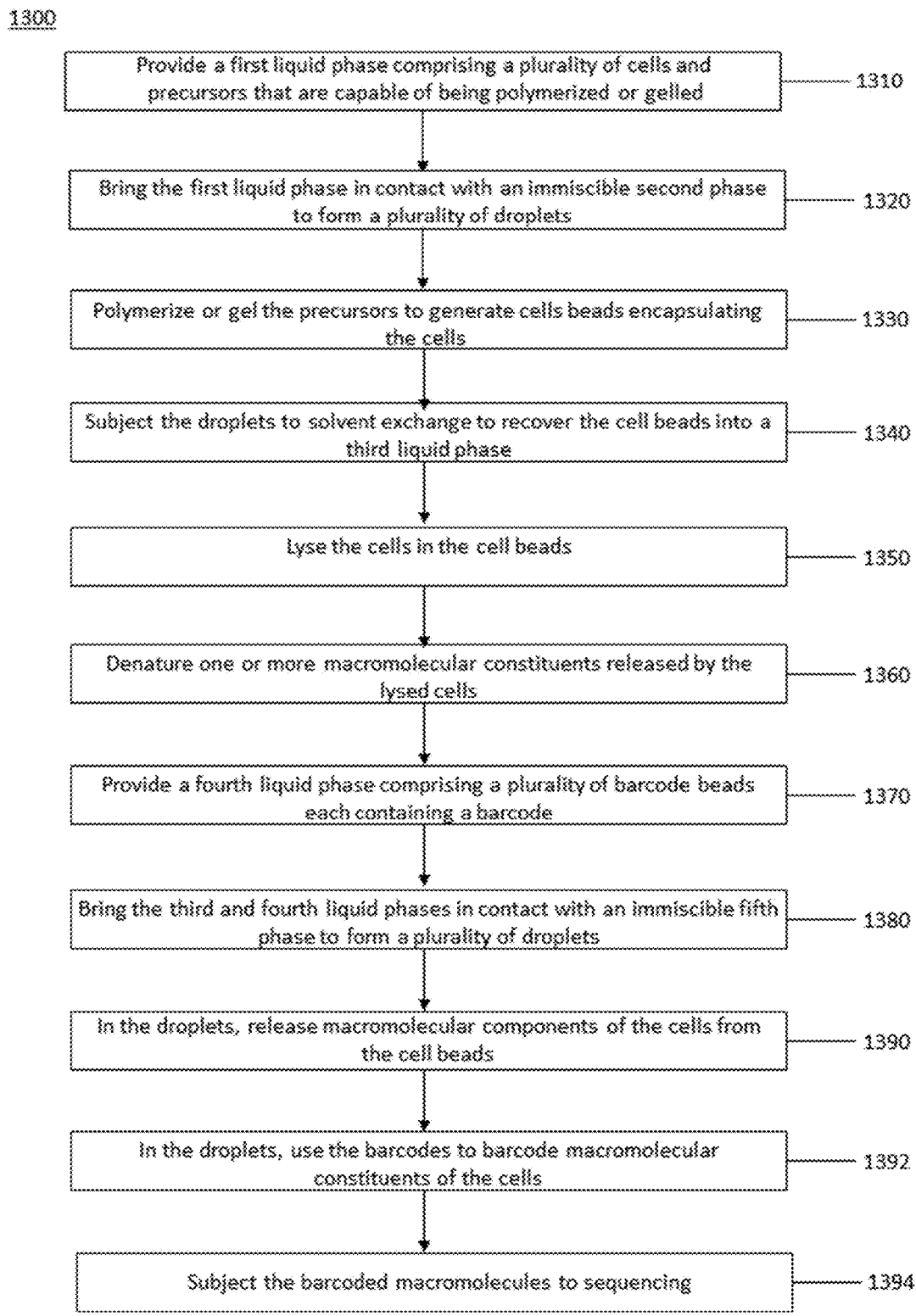
FIG. 13 shows a flowchart for a method of producing droplets containing a cell bead and a barcode bead and generating sequence reads from macromolecular components of the cell bead.

FIG. 13 shows a flowchart that depicts an example method 1300 of producing droplets containing a cell bead (e.g., comprising a cell or components of a cell) and a barcode bead (e.g., gel bead) comprising barcode sequences and generating sequence reads from macromolecular components of a cell of which cell or components have been encapsulated by a polymer or gel. In some cases, the method 1300 may comprise the following operations.

In operation 1310, a first liquid phase comprising a plurality of cells is provided. The first liquid phase may be aqueous. The first liquid phase may comprise a cellular growth medium. The first liquid phase may comprise a minimal growth medium. The first liquid phase may further comprise precursors that are capable of being polymerized or gelled. The precursors that are capable of being polymerized or gelled may comprise poly(acrylamide-co-acrylic acid). The first liquid phase may further comprise a first agent that is completely or partially capable of polymerizing or gelling the precursors, such as an acylating agent. The acylating agent may comprise 4-(4,6-dimethoxy-1,3,5-triazin-2-yl)-4-methylmorpholinium chloride (DMTMM). The first liquid phase may comprise other salts of 4-(4,6-dimethoxy-1,3,5-triazin-2-yl)-4-methylmorpholinium. Additional examples of precursors include polyacrylamide, species comprising a disulfide bond (e.g., cystamine (2,2'-dithiobis(ethylamine), disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. Moreover, in some cases, precursors are pre-formed polymer chains that can be crosslinked (e.g., via gelation) to form larger structures such as beads. In some cases, precursors may be monomeric species that are polymerized to form larger structures such as beads.

The first liquid phase may further comprise one or more of a magnetic particle, reagents for reverse transcription (e.g., oligonucleotide primers or reverse transcriptase), reagents for nucleic acid amplification (e.g., primers (e.g. random primers, primers specific for given DNA loci), polymerases, nucleotides (e.g. unmodified nucleotides, modified nucleotides, or non-canonical nucleotides), co-factors (e.g., ionic co-factors)) or reagents for nucleic acid modification, including ligation, digestion, methylation, random mutagenesis, bisulfite conversion, uracil hydrolysis, nucleic acid repair, nucleic acid insertion or cleavage (e.g. via CRISPR/Cas9-mediated or transposon-mediated insertion or cleavage), capping and decapping.

In operation 1320, the first liquid phase can be brought into contact with an immiscible second liquid phase to form a plurality of droplets. The third liquid phase may comprise an oil and may also comprise a surfactant. The third liquid phase may comprise a fluorinated hydrocarbon. In some cases, a given droplet may include a single cell and precursors that are capable of being polymerized or gelled. In some cases, at least 80%, at least 90%, at least 95%, at least 99%, at least 99.5%, at least 99.9%, at least 99.95%, or at least 99.99% of the droplets may contain a single cell.

In operation 1330, the droplets can be subjected to conditions sufficient to polymerize or gel the precursors. The conditions sufficient to polymerize or gel the precursors may comprise exposure to heating, cooling, electromagnetic radiation, or light. The conditions sufficient to polymerize or gel the precursors may comprise any conditions sufficient to polymerize or gel the precursors. Following polymerization or gelling, a polymer or gel may be formed around the cells or cell components, such that they are encapsulated in cell beads. The polymer or gel may be diffusively permeable to chemical or biochemical reagents. The polymer or gel may be diffusively impermeable to macromolecular constituents of the cells or cell components. In this manner, the polymer or gel may act to allow the cell beads to be subjected to chemical or biochemical operations while spatially confining the contents of the cells beads to a region defined by the polymer or gel.

The cell beads may be functionalized to bind to targeted analytes, such as nucleic acids, proteins, or other analytes. The polymer or gel of the cell beads may be polymerized or gelled via a passive mechanism. The polymer or gel may be stable in alkaline conditions or at elevated temperature. The polymer or gel may have mechanical properties similar to the mechanical properties (e.g., tensile strength) of a bead. The polymer or gel may be of a lower density than an oil. The cell beads may be of a density that is roughly similar to that of a buffer. The cell beads may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The cell beads may be biocompatible. The polymer or gel of the cell beads may maintain or enhance cell viability. The cell beads may be biochemically compatible. The polymer or gel of the cell beads may be polymerized and/or depolymerized thermally, chemically, enzymatically, and/or optically.

In some examples, the resulting cell beads may comprise poly(acrylamide-co-acrylic acid) crosslinked with disulfide linkages. The preparation of these cell beads may comprise a two-operation reaction. In the first activation operation, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking operation, the ester formed in the first operation may be exposed to a disulfide crosslinking agent. For instance, the ester may be exposed to cystamine (2,2'-dithiobis(ethylamine)). Following the two operations, an encapsulated cell or its components are surrounded by polymeric strands, such as polyacrylamide strands linked together by disulfide bridges thereby resulting in a cell bead. In this manner, the cell may be encased inside of the cell bead. In some cases, one or more magnetic (e.g., paramagnetic) particles may be encapsulated within a cell bead such, as for example, by also including such particles within a droplet along with polymeric precursors.

Cell beads may be or include a cell, cell derivative, cellular material and/or material derived from the cell in, within, or encased in a matrix, such as a polymeric matrix. A cell encapsulated by a bead may be a live cell.

In operation 1340, cell beads generated from precursors in droplets are suspended in the second liquid phase may be resuspended into an aqueous environment by a solvent exchange process. Such processing can promote the processing of cell beads with additional aqueous phase materials. The solvent exchange process may comprise the operations of collecting cell beads in droplets (for instance, in an Eppendorf tube or other collection vessel), removing excess oil (for instance, by pipetting), adding a ligation buffer (such as a 3× ligation buffer), vortexing, adding a buffer (such as a 1×1H,1H,2H,2H-perfluoro-1-octanol (PFO) buffer), vortexing, centrifugation, and separation. The separation operation may comprise magnetic separation via attraction of encapsulated magnetic particles. The magnetic separation may be accomplished by using a magnetic separating apparatus to pull cell beads containing magnetic particles away from unwanted remaining oil and solvents. For instance, the magnetic separation apparatus may be used to pull cell beads containing magnetic particles away from the ligation buffer and PFO to allow removal of the ligation buffer and PFO (for instance by pipetting). The cell beads containing magnetic particles may then be suspended in a ligation buffer and vortexed. The cell beads containing paramagnetic particles may again be separated magnetically and the ligation buffer may be removed. This cycle of re-suspension, vortexing, and magnetic separation may be repeated until the cell beads are free or substantially free of oil phase and suspended in aqueous medium. For instance, the cycle may be repeated 1, 2, 3, 4, 5, 6, 7, 8, 9, 10, or more than 10 times. The cell beads may then be processed in aqueous phases and with additional materials.

Once the cell beads are in an aqueous medium, the cell beads may be further treated. For instance, the cell beads in aqueous solution may be filtered (for instance, using a 70 µm filter) to remove clumps and/or large cell beads from the solution. In some cases, additional reagents may be added to and/or removed from the aqueous medium to further process the cell beads. Further processing can include, without limitation, reverse transcription, nucleic acid amplification, and nucleic acid modification of macromolecular constituents within the cell beads.

In operation 1350, the cell beads can be subjected to conditions sufficient to lyse the cells encapsulated in the cell beads. In some cases, lysis is completed via a lysis agent present in a droplet. In some cases, lysis is completed in bulk, for example with the aid of a lysis agent that contacts a plurality of cell beads in one pot. In some cases, the lysis of the cells occurs subsequent to subjecting the cells to conditions sufficient to encapsulate the cells in the polymer or gel. The lysis may release macromolecular constituents of the lysed cells. The lysis may be achieved by exposing the cell beads to sodium hydroxide (NaOH), potassium hydroxide (KOH), or any other alkaline agent. The lysis may be achieved by exposing the cell beads to a detergent, such as sodium dodecyl sulfate (SDS), 4-(1,1,3,3-Tetramethylbutyl) phenyl-polyethylene glycol (TRITON X-100) or any non-ionic surfactant, or a saponin. The lysis may be achieved by exposing the cell beads to an enzyme, such as a proteinase or a lytic enzyme (such as a lysozyme, cellulose, or zymolase). The lysis may be achieved by exposing the cell beads to freeze thawing. The lysis may be achieved by exposing the cell beads to electromagnetic radiation, such as ultraviolet (UV) light. The lysis may be achieved by exposing the cell beads to heat.

The lysis may be achieved by exposing the cell beads to any other lysis agent. A cell bead may retain species released from lysed cells within the cell bead, such as, for example, via its polymeric or gel structure.

In operation 1360, the cell beads can be subjected to conditions sufficient to denature one or more macromolecular constituents released by the lysed cells. In some cases, denaturation occurs in bulk where more than one cell bead is subjected to denaturation conditions in a single pot. In some cases, denaturation is achieved via a denaturation agent present in a droplet. The denaturing may be achieved by exposing the cell beads to sodium hydroxide (NaOH). The denaturing may be achieved by exposing the cell beads to any other denaturing agent. In some cases, operation 1360 is completed contemporaneously with operation 1350. In some examples, a denaturing agent can both denature macromolecular constituents and lyse the cells within the cell beads.

In operation 1370, a fourth liquid phase comprising a plurality of barcode beads can be provided. The fourth liquid phase may be aqueous. The fourth liquid phase may comprise a cellular growth medium. The fourth liquid phase may comprise a minimal growth medium. The barcode beads each contain a barcode to barcode one or more macromolecular constituents of the plurality of cell beads. In some cases, the third liquid phase and the fourth liquid phase are the same phase. In some cases, the third liquid phase and the fourth liquid phase are mixed to provide a mixed phase.

In operation 1380, the third liquid phase and the fourth liquid phase can be brought together with a fifth liquid phase that is immiscible with the third and fourth liquid phases. The fifth liquid phase may interact with the third and fourth liquid phases in such a manner as to partition cells beads encapsulating cellular material and the plurality of barcode beads into a plurality of droplets. The fifth liquid phase may comprise an oil and may also comprise a surfactant. The fifth liquid phase may comprise a fluorinated hydrocarbon. In some cases, a given droplet may include a single cell bead and a single barcode bead. In some cases, at least 80%, at least 90%, at least 95%, at least 99%, at least 99.5%, at least 99.9%, at least 99.95%, or at least 99.99% of the droplets may contain a single cell bead. Moreover, while the cell beads and barcode beads are partitioned into droplets in this example, other types of partitions can be implemented in operation 1380, including those described elsewhere herein, such as a well.

In operation 1390, the cell beads are subjected to conditions sufficient to release the macromolecular constituents from cell beads. The release of the macromolecular constituents may be achieved by exposing cell beads to a reducing agent (e.g., dithiothreitol (DTT)), which may be present in a droplet. The release of the macromolecular constituents may be achieved by exposing the cell beads to any substance capable of releasing the macromolecular constituents. In some cases, operation 1390 also includes releasing barcodes from the barcode beads, which may be achieved with the same stimulus, such as, for example, that used to release macromolecular constituents from cell beads. In some cases, the stimuli are different. Released barcodes can then participate in barcoding as in operation 1392.

In operation 1392, the barcode is used to barcode one or more macromolecular constituents of a given cell bead in a given droplet. In some cases, the macromolecular constituents of the cell bead are subjected to conditions sufficient for nucleic acid amplification for barcoding. In such cases, the barcode may function as a primer during such amplification. In other cases, ligation can be used for barcoding. In some cases, the barcode is used to identify one or more macromolecular constituents of the cell bead. In some cases, the barcode is subjected to nucleic acid sequencing to identify one or more macromolecular components. In some cases, the sequencing is untargeted sequencing. In some cases, the sequencing is targeted sequencing.

In operation 1394, barcoded macromolecules (or derivatives thereof) are subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell (which may have been encapsulated in a cell bead) from which the barcoded sequencing read was generated. Such capability can link particular sequences to particular cells. Additional details and examples regarding nucleic acid sequencing methods are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 14:
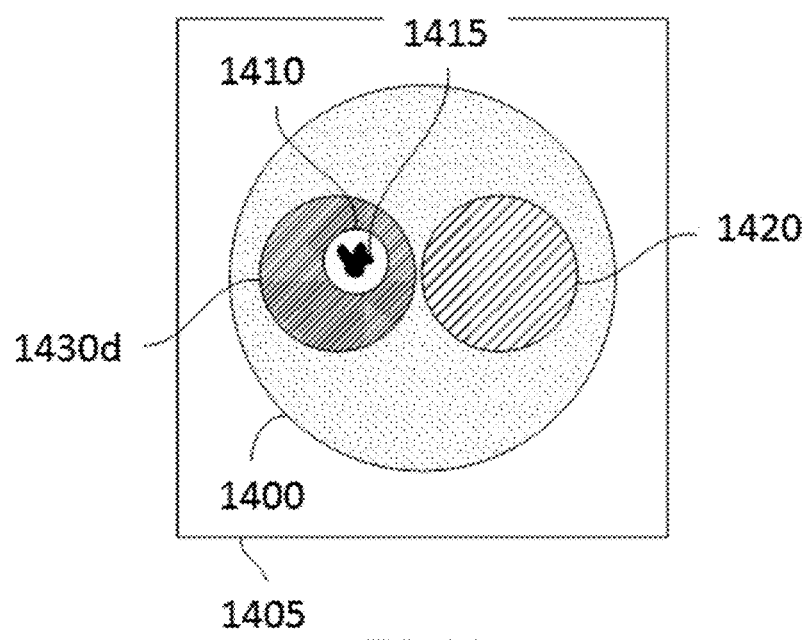
FIG. 14 shows a droplet containing a cell bead and a barcode bead produced using the method of FIG. 13.

FIG. 14 shows a droplet containing a single cell bead and a single barcode bead produced using the method 1300. A droplet 1400 of aqueous liquid is formed inside a volume 1405 of a liquid that is immiscible with the aqueous liquid. The droplet contains a single barcode bead 1420. The droplet also contains a cell 1410 containing one or more macromolecular constituents 1415. The cell may be surrounded by a gel or polymer 1430d and is encapsulated within a cell bead 1430d.

Figure 25:
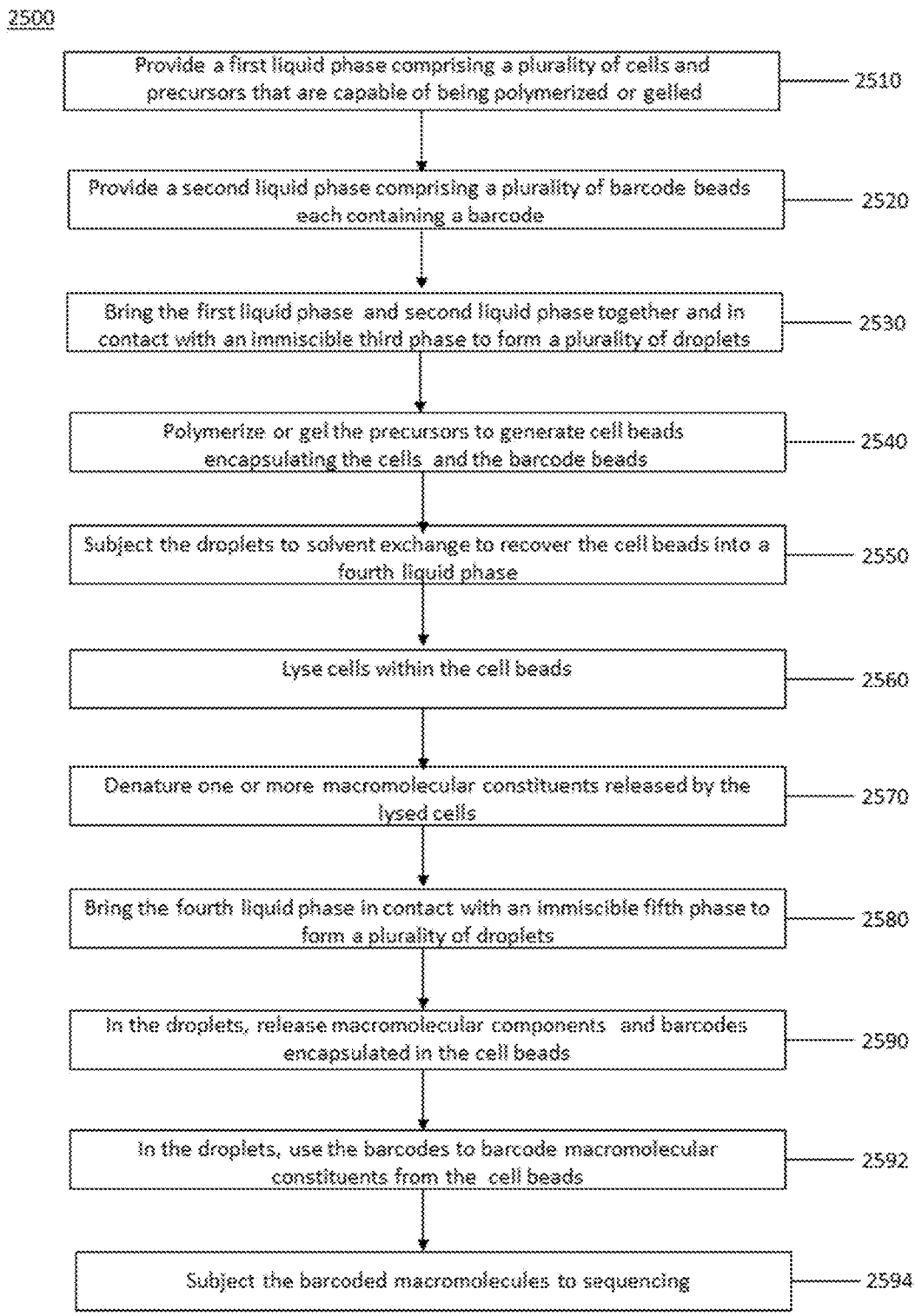
FIG. 25 shows a flowchart for an example method of producing droplets containing cell beads.

FIG. 25 shows a flowchart that depicts an example method 2500 of producing droplets containing a cell bead comprising a cell and a barcode bead (e.g., gel bead) comprising barcode sequences and generating sequence reads from macromolecular components of the cell. In some cases, the method 2500 comprises the following operations.

In operation 2510, a first liquid phase comprising a plurality of cells is provided. The first liquid phase may be aqueous. The first liquid phase may comprise a cellular growth medium. The first liquid phase may comprise a minimal growth medium. The first liquid phase may further comprise precursors that are capable of being polymerized or gelled. The precursors that are capable of being polymerized or gelled may comprise poly(acrylamide-co-acrylic acid). The first liquid phase may further comprise a first agent that is completely or partially capable of polymerizing or gelling the precursors, such as an acylating agent. The acylating agent may comprise 4-(4,6-dimethoxy-1,3,5-triazin-2-yl)-4-methylmorpholinium chloride (DMTMM). The first liquid phase may comprise other salts of 4-(4,6-dimethoxy-1,3,5-triazin-2-yl)-4-methylmorpholinium. Additional examples of precursors include polyacrylamide, species comprising a disulfide bond (e.g., cystamine (2,2'-dithiobis(ethylamine), disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. Moreover, in some cases, precursors are pre-formed polymer chains that can be crosslinked (e.g., via gelation) to form larger structures such as beads. In some cases, precursors may be monomeric species that are polymerized to form larger structures such as beads.

The first liquid phase may further comprise one or more of a magnetic particle, reagents for reverse transcription (e.g., oligonucleotide primers or reverse transcriptase), reagents for nucleic acid amplification (e.g., primers (e.g. random primers, primers specific for given DNA loci), polymerases, nucleotides (e.g. unmodified nucleotides, modified nucleotides, or non-canonical nucleotides), co-factors (e.g., ionic co-factors)) or reagents for nucleic acid modification, including ligation, digestion, methylation, random mutagenesis, bisulfite conversion, uracil hydrolysis, nucleic acid repair, nucleic acid insertion or cleavage (e.g. via CRISPR/Cas9-mediated or transposon-mediated insertion or cleavage), capping and decapping.

In operation 2520, a second liquid phase comprising a plurality of barcode beads can be provided. The second liquid phase may be aqueous. The second liquid phase may comprise a cellular growth medium. The second liquid phase may comprise a minimal growth medium. The barcode beads each contain a barcode to barcode one or more macromolecular constituents of the plurality of cell beads. In some cases, the first liquid phase and the third liquid phase are the same phase. In some cases, the first liquid phase and the second liquid phase are mixed to provide a mixed phase.

In operation 2530, the first liquid phase and second liquid phase can be brought together, if not already mixed, and two are brought into contact with an immiscible second liquid phase to form a plurality of droplets. The third liquid phase may comprise an oil and may also comprise a surfactant. The third liquid phase may comprise a fluorinated hydrocarbon. In some cases, a given droplet may include a single cell and precursors that are capable of being polymerized or gelled. In some cases, at least 80%, at least 90%, at least 95%, at least 99%, at least 99.5%, at least 99.9%, at least 99.95%, or at least 99.99% of the droplets may contain a single cell.

In operation 2540, the droplets are subjected to conditions sufficient to polymerize or gel the precursors. The conditions sufficient to polymerize or gel the precursors may comprise exposure to heating, cooling, electromagnetic radiation, or light. The conditions sufficient to polymerize or gel the precursors may comprise any conditions sufficient to polymerize or gel the precursors. Following polymerization or gelling, a polymer or gel may be formed around the cells and barcode beads, such that the cells and barcode beads are encapsulated in cell beads. The polymer or gel of the cell beads may be diffusively permeable to chemical or biochemical reagents. The polymer or gel of the cell beads may be diffusively impermeable to macromolecular constituents of the cells. In this manner, the polymer or gel may act to allow the cells to be subjected to chemical or biochemical operations while spatially confining the macromolecular constituents to a region of the droplet defined by the polymer or gel.

The polymer or gel of the cell beads may be functionalized to bind to targeted analytes, such as nucleic acids, proteins, or other analytes. The polymer or gel of the cell beads may be polymerized or gelled via a passive mechanism. The polymer or gel of the cell beads may be stable in alkaline conditions or at elevated temperature. The polymer or gel of the cell beads may be of a lower density than an oil. The polymer or gel of the cell beads may be of a density that is roughly similar to that of a buffer. The polymer or gel of the cell beads may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel of the cell beads may be biocompatible. The polymer or gel of the cell beads may maintain or enhance cell viability. The polymer or gel of the cell beads may be biochemically compatible. The polymer or gel of the cell beads may be polymerized and/or depolymerized thermally, chemically, enzymatically, and/or optically.

In some examples, the resulting cell beads may comprise poly(acrylamide-co-acrylic acid) crosslinked with disulfide linkages. The preparation of this polymer may comprise a two-operation reaction. In the first activation operation, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking operation, the ester formed in the first operation may be exposed to a disulfide crosslinking agent. For instance, the ester may be exposed to cystamine (2,2'-dithiobis(ethylamine)). Following the two operations, an encapsulated cell and barcode bead is surrounded by polymeric strands, such as polyacrylamide strands linked together by disulfide bridges thereby resulting in a cell bead comprising the cell and barcode bead. In this manner, the cell and barcode bead may be encased inside of the cell bead. In some cases, one or more magnetic (e.g., paramagnetic) particles may be encapsulated within the cell bead such, as for example, by also including such particles within a droplet along with polymeric precursors.

Cell beads may be or include a cell, cell derivative, cellular material and/or material derived from the cell in, within, or encased in a matrix, such as a polymeric matrix. A cell encapsulated by a bead may be a live cell.

In operation 2550, cell beads generated from precursors, cells and barcode beads in droplets are suspended in the third liquid phase and may be resuspended into a fourth liquid phase (e.g., an aqueous phase) by a solvent exchange process. Such processing can promote the processing of cell beads with additional aqueous phase materials. The solvent exchange process may comprise the operations of collecting cell beads in droplets (for instance, in an Eppendorf tube or other collection vessel), removing excess oil (for instance, by pipetting), adding a ligation buffer (such as a 3× ligation buffer), vortexing, adding a buffer (such as a 1×1H,1H,2H, 2H-perfluoro-1-octanol (PFO) buffer), vortexing, centrifugation, and separation. The separation operation may comprise magnetic separation via attraction of encapsulated magnetic particles. The magnetic separation may be accomplished by using a magnetic separating apparatus to pull cell beads containing magnetic particles away from unwanted remaining oil and solvents. For instance, the magnetic separation apparatus may be used to pull cell beads containing magnetic particles away from the ligation buffer and PFO to allow removal of the ligation buffer and PFO (for instance by pipetting). The cell beads containing magnetic particles may then be suspended in a ligation buffer and vortexed. The cell beads containing paramagnetic particles may again be separated magnetically and the ligation buffer may be removed. This cycle of re-suspension, vortexing, and magnetic separation may be repeated until the cell beads are free or substantially free of oil phase and suspended in aqueous medium. For instance, the cycle may be repeated 1, 2, 3, 4, 5, 6, 7, 8, 9, 10, or more than 10 times. The cell beads may then be processed in aqueous phases and with additional materials in aqueous phases.

Once the cell beads are in an aqueous medium, the cell beads may be further treated. For instance, the cell beads in aqueous solution may be filtered (for instance, using a 70 µm filter) to remove clumps and/or large cell beads from the solution. In some cases, additional reagents may be added to and/or removed from the aqueous medium to further process the cell beads. Further processing can include, without limitation, reverse transcription, nucleic acid amplification, and nucleic acid modification of macromolecular constituents within the cell beads.

In operation 2560, the cell beads can be subjected to conditions sufficient to lyse the cells encapsulated in the cell beads. In some cases, lysis is completed via a lysis agent present in a droplet. In some cases, lysis is completed in bulk, for example with the aid of a lysis agent that contacts a plurality of cell beads in one pot. In some cases, the lysis of cells of the cell beads occurs subsequent to subjecting the cells to conditions sufficient to encapsulate the cells in the polymer or gel. The lysis may release macromolecular constituents of the lysed cells of the cell beads. The lysis may be achieved by exposing the cell beads to sodium hydroxide (NaOH), potassium hydroxide (KOH), or any other alkaline agent. The lysis may be achieved by exposing the cell beads to a detergent, such as sodium dodecyl sulfate (SDS), 4-(1,1,3,3-Tetramethylbutyl)phenyl-polyethylene glycol (TRITON X-100) or any non-ionic surfactant, or a saponin. The lysis may be achieved by exposing the cell beads to an enzyme, such as a proteinase or a lytic enzyme (such as a lysozyme, cellulose, or zymolase). The lysis may be achieved by exposing the cell beads to freeze thawing. The lysis may be achieved by exposing the cell beads to electromagnetic radiation, such as ultraviolet (UV) light. The lysis may be achieved by exposing the cell beads to heat. The lysis may be achieved by exposing the cell beads to any other lysis agent. A cell bead may retain species released from lysed cells within the cell bead, such as, for example, via its polymeric or gel structure.

In operation 2570, the cell beads can be subjected to conditions sufficient to denature one or more macromolecular constituents released by the lysed cells within the cell beads. In some cases, denaturation occurs in bulk where more than one cell bead is subjected to denaturation conditions in a single pot. In some cases, denaturation is achieved via a denaturation agent present in a droplet. The denaturing may be achieved by exposing the cell beads to sodium hydroxide (NaOH). The denaturing may be achieved by exposing the cell beads to any other denaturing agent. In some cases, operation 2570 is completed contemporaneously with operation 2560. In some examples, a denaturing agent can both denature macromolecular constituents and lyse the cells of the cell beads.

In operation 2580, the fourth liquid phase, having the cell beads, is brought into contact with a fifth liquid phase that is immiscible with the fourth liquid phase. The fifth liquid phase may interact with the fourth liquid phase in such a manner as to partition cell beads into a plurality of droplets. The fifth liquid phase may comprise an oil and may also comprise a surfactant. The fifth liquid phase may comprise a fluorinated hydrocarbon. In some cases, a given droplet may include a single cell bead. In some cases, at least 80%, at least 90%, at least 95%, at least 99%, at least 99.5%, at least 99.9%, at least 99.95%, or at least 99.99% of the droplets may contain a single cell bead. In some cases, additional precursors are added to the fourth liquid phase, droplets generated and the precursors polymerized or gelled (including as described herein) to generate even larger cell beads comprising the cell bead. The larger cell beads can be stored for future use. Moreover, while the cell beads are partitioned into droplets in this example, other types of partitions can be implemented at operation 2580, including those described elsewhere herein, such as a well.

In operation 2590, the cell beads can then be subjected to conditions sufficient to release the barcode beads and macromolecular constituents of cells from the cell beads. The release of the macromolecular constituents may be achieved by exposing the cell beads to a reducing agent (e.g., dithiothreitol (DTT)), which may be present in the droplet. The release of the macromolecular constituents may be achieved by exposing the cell beads to any substance capable of releasing the macromolecular constituents. In some cases, operation 2590 also includes releasing barcodes from the barcode beads, which may be achieved with the same stimulus, such as, for example, used to reverse cross-linking of the cell bead. In some cases, the stimuli are different. Released barcodes can then participate in barcoding as in operation 2592.

In operation 2592, the barcodes is used to barcode one or more macromolecular constituents of a given cell bead in a given droplet. In some cases, the macromolecular constituents of the cell bead are subjected to conditions sufficient for nucleic acid amplification for barcoding. In such cases, a barcode may function a primer during such amplification. In some cases, ligation is used for barcoding. In some cases, the barcode is used to identify one or more macromolecular constituents of the cell bead. In some cases, the barcode is subjected to nucleic acid sequencing to identify one or more macromolecular components. In some cases, the sequencing is untargeted sequencing. In some cases, the sequencing is targeted sequencing.

In operation 2594, barcoded macromolecules (or derivatives thereof) are subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell from which the barcoded sequencing read was generated. Such capability can link particular sequences to particular cells. Additional details and examples regarding nucleic acid sequencing methods are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 26A:
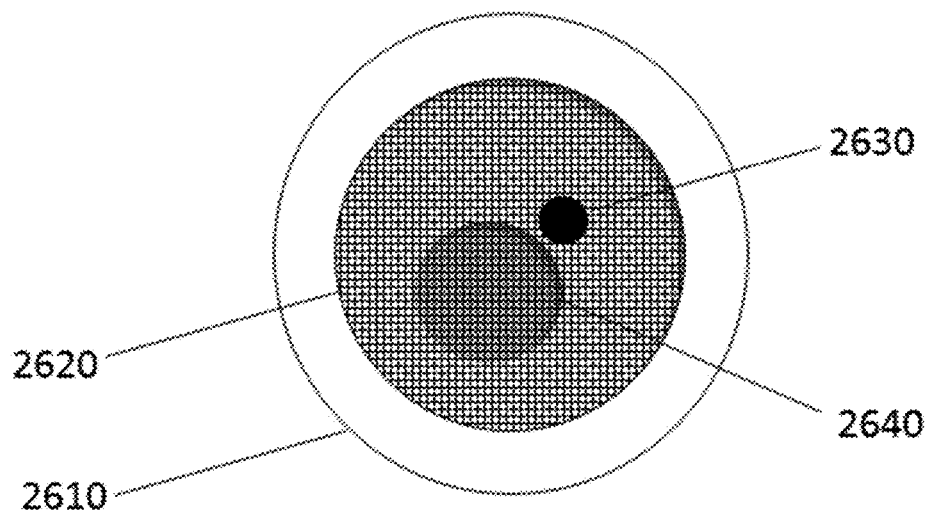
FIG. 26A schematically depicts an example droplet comprising a cell bead.
Figure 26B:
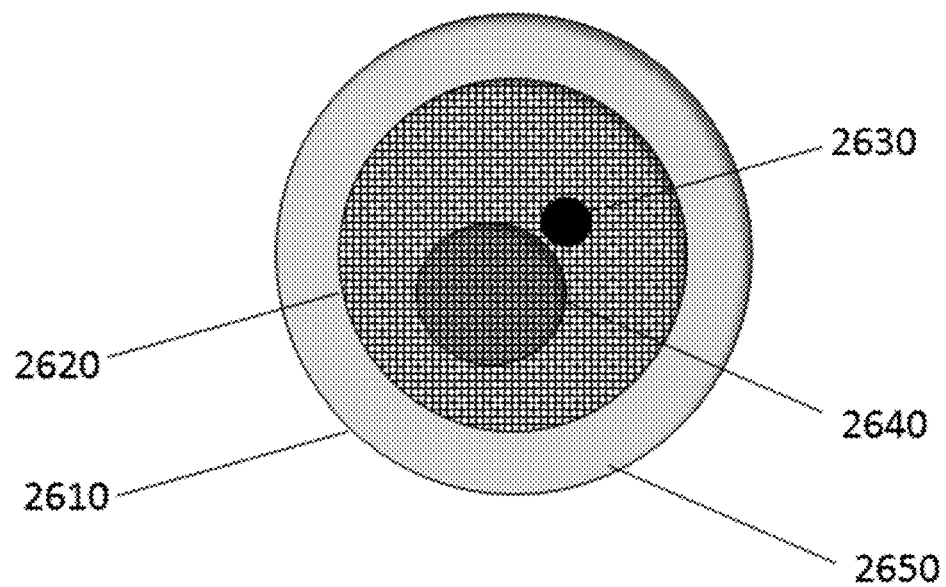
FIG. 26B schematically depicts an example first cell bead comprising a second cell bead.

FIG. 26A shows a droplet 2610 containing a cell bead 2620 that encapsulates a cell 2630 and a single gel bead 2640 comprising a barcode sequence produced using the method 2500. FIG. 26B shows a larger cell bead 2650 comprising the elements of droplet 2610 in FIG. 26A, where the larger cell bead 2650 has been generated from precursors present in a droplet and subsequently polymerized or gelled.

Figure 15:
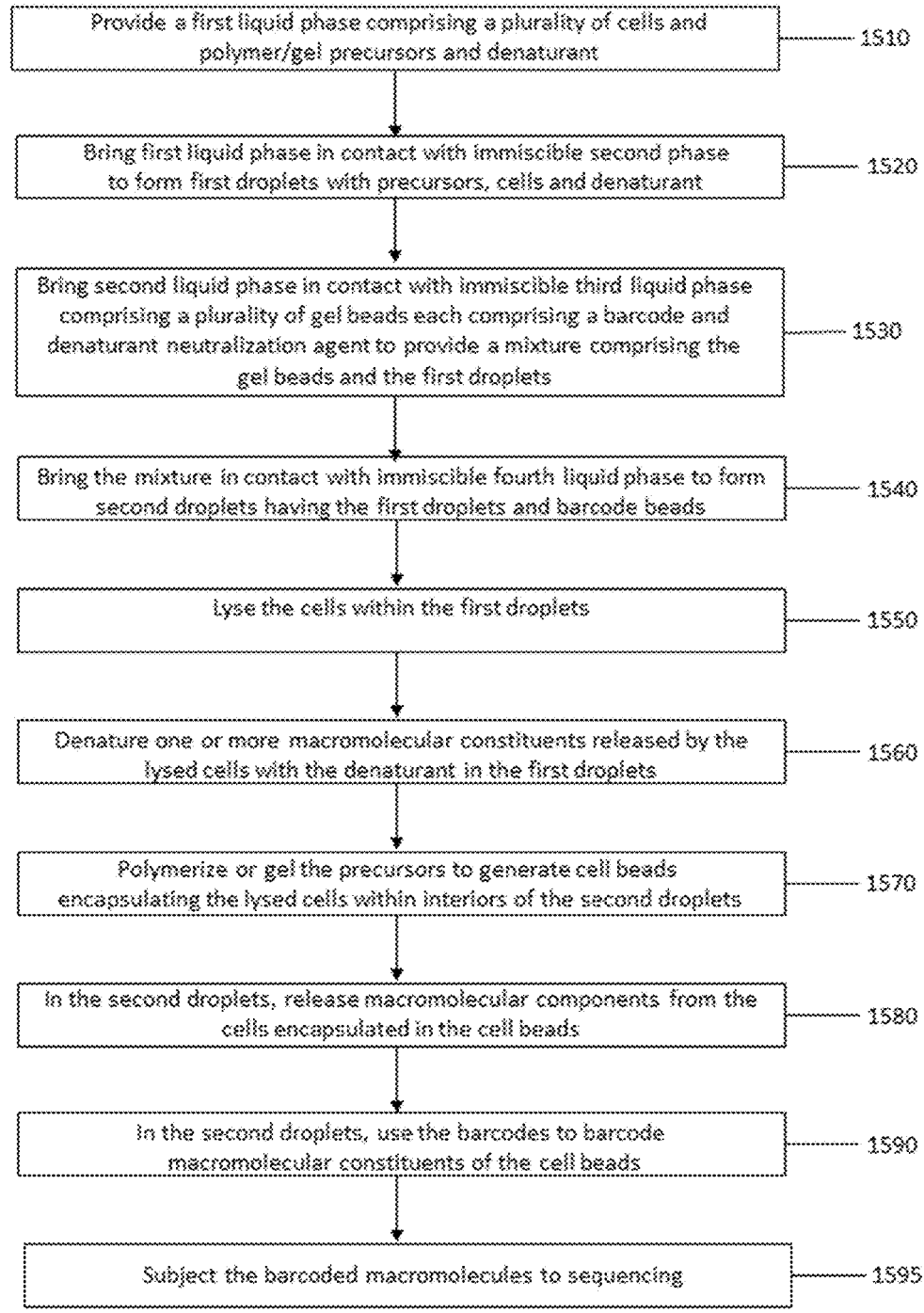
FIG. 15 shows a flowchart for a method of producing droplets containing a cell bead, a barcode bead and generating sequence reads from macromolecular components of the cell bead.

FIG. 15 shows a flowchart depicting an example method 1500 of producing droplets containing a droplet containing a cell bead, a barcode bead (e.g., a gel bead), and generating sequence reads from macromolecular components a cell associated with the cell bead. In some cases, the method 1500 may comprise the following operations.

In operation 1510, a first liquid phase comprising a plurality of cells, precursors capable of being polymerized or gelled and a denaturant is provided. The first liquid phase may be aqueous. The first liquid phase may comprise a cellular growth medium. The first liquid phase may comprise a minimal growth medium.

In operation 1520, the first liquid phase can be brought together with a second liquid phase that is immiscible with the first liquid phase. The first liquid phase may interact with the second liquid phase in such a manner as to partition each of the plurality of cells into a plurality of first droplets that also include polymer or gel precursors and denaturant. The second liquid phase may comprise an oil. The second liquid phase may comprise a fluorinated hydrocarbon. In some cases, a given first droplet may include a single cell. In some cases, at least 80%, at least 90%, at least 95%, at least 99%, at least 99.5%, at least 99.9%, at least 99.95%, or at least 99.99% of the first droplets may contain a single cell.

In operation 1530, the second liquid phase can be brought into contact with an immiscible third phase comprising a plurality of barcode beads comprising barcodes and a denaturant neutralization agent. The third liquid phase may be aqueous. The barcode beads each contain a barcode to barcode one or more macromolecular constituents of the plurality of cells. In some cases, the first liquid phase and the third liquid phase are the same phase. The bringing together of the second liquid phase and the third liquid phase can generate a mixture comprising the barcode beads and the first droplets.

In operation, 1540, the mixture generated in operation 1530 can be brought into contact with an immiscible fourth liquid phase to form second droplets having the first droplets and beads (e.g., a droplet within a droplet configuration). The fourth liquid phase may interact with the mixture in such a manner as to partition each of the first droplets and the plurality of barcode beads into a plurality of second droplets. The fourth liquid phase may comprise an oil and may also include a surfactant. The fourth liquid phase may comprise a fluorinated hydrocarbon. In some cases, a given second droplet may include a single first droplet and a single barcode bead. In some cases, at least 80%, at least 90%, at least 95%, at least 99%, at least 99.5%, at least 99.9%, at least 99.95%, or at least 99.99% of the second droplets may contain a single first droplet.

In operation 1550, the cells in the first droplets can be subjected to conditions sufficient to lyse the cells. In some cases, lysis is completed with the aid of a lysis agent in a droplet. The lysis may release macromolecular constituents of the lysed cell bead into the first droplet. The lysis may be achieved via the action of the denaturant (e.g., sodium hydroxide (NaOH), potassium hydroxide (KOH), or any other alkaline agent) also present in the first droplet. In some cases, the lysis may be achieved with a detergent present in the first droplet, such as sodium dodecyl sulfate (SDS), 4-(1,1,3,3-Tetramethylbutyl)phenyl-polyethylene glycol (TRITON X-100) or any non-ionic surfactant, or a saponin. The lysis may be achieved with an enzyme in the first droplet, such as a proteinase or a lytic enzyme (such as a lysozyme, cellulose, or zymolase). The lysis may be achieved by exposing first droplet to freeze thawing. The lysis may be achieved by exposing the first droplet to electromagnetic radiation, such as ultraviolet (UV) light. The lysis may be achieved by exposing the first droplet to heat. The lysis may be achieved by exposing the contents of the first droplet to any other lysis agent.

In operation 1560, the lysed cells can then be subjected to conditions sufficient to denature one or more macromolecular constituents released by the lysed cells. In some examples, lysis is completed with the aid of a denaturation agent present in the first droplet, such as, for example sodium hydroxide (NaOH). In some cases, the denaturation agent is present outside the first droplet. In some examples, the same denaturing agent can both denature macromolecular constituents and lyse the cells.

In operation 1570, the droplets generated in operation 1540 can be subjected to conditions sufficient to polymerize or gel the precursors within first droplets. Polymerization or gelling of the precursors can generate cell beads that encapsulate released/denatured macromolecular components from the lysed cells. In cases where a first droplet generated in operation 1520 comprises a single cell, the resulting generated from that droplet will also comprise macromolecular constituents of the single cell. The conditions sufficient to polymerize or gel the precursors may comprise exposing the first droplets to heating, cooling, electromagnetic radiation, or light. The conditions sufficient to polymerize or gel the precursors may comprise any exposing the first droplets conditions sufficient to polymerize or gel the precursors. Following polymerization or gelling, a polymer or gel may be formed around the material released from cell lysis to generate a cell bead. The cell bead may be diffusively permeable to chemical or biochemical reagents. The cell bead may be diffusively impermeable to macromolecular constituents of the cell bead. In this manner, the polymer or gel may act to allow the cell bead to be subjected to chemical or biochemical operations while spatially confining the macromolecular constituents to a region of the droplet defined by the polymer or gel. The polymer or gel of the cell bead may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel of the cell bead may comprise any other polymer or gel. In some cases, polymerization of the precursors in the first droplets generates cell beads comprising the macromolecular constituents of cells and also releases the cells beads from the first droplets and into the interiors of the second droplets. Upon release of the cell beads from the first droplets, denaturant neutralization agent present in interiors of the second droplets neutralizes the denaturant that is also released with the cell beads. Polymerization may also be coupled to or precede a solvent exchange process that aids in releasing cell beads from the first droplets and into the interiors of the second droplets.

In operation 1580, the cell beads can be subjected to conditions sufficient to release the macromolecular constituents from cell beads. The release of the macromolecular constituents may be achieved by exposing the cell beads to a reducing agent (e.g., dithiothreitol (DTT)), which may be present in a droplet. The release of the macromolecular constituents may be achieved by exposing the cell beads to any substance capable of releasing the macromolecular constituents. In some cases, operation 1580 also includes releasing barcodes from the barcode beads in the second droplets which may be achieved with the same stimulus, such as, for example, used to reverse cross-linking of the cell bead. In some cases, the stimuli are different. Released barcodes can then participate in barcoding as in operation 1590.

In operation 1590, barcodes can be used to barcode one or more macromolecular constituents of a given single cell bead in a given second droplet. In some cases, the macromolecular constituents of the cell bead are subjected to conditions sufficient for nucleic acid amplification for barcoding. In such cases, a barcode can function as a primer in such amplification. In other cases, ligation may be used for barcoding. In some cases, the barcode is used to identify one or more macromolecular constituents of the cell bead. In some cases, the barcode is subjected to nucleic acid sequencing to identify one or more macromolecular components. In some cases, the sequencing is untargeted sequencing. In some cases, the sequencing is targeted sequencing.

In operation 1595, the barcoded macromolecules (or derivatives thereof) are subjected to sequencing to generate reads. The sequencing may be performed within a second droplet. The sequencing may be performed outside of a second droplet. For instance, the sequencing may be performed by releasing the barcoded macromolecules from a second droplet and sequencing the barcoded macromolecules using a sequencer, such as an Illumina sequencer or any other sequencer described herein. In some cases, a given barcoded sequencing read can be used to identify the cell from which the barcoded sequencing read was generated. Such capability can link particular sequences to particular cells. Additional details and examples regarding nucleic acid sequencing methods are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 16:
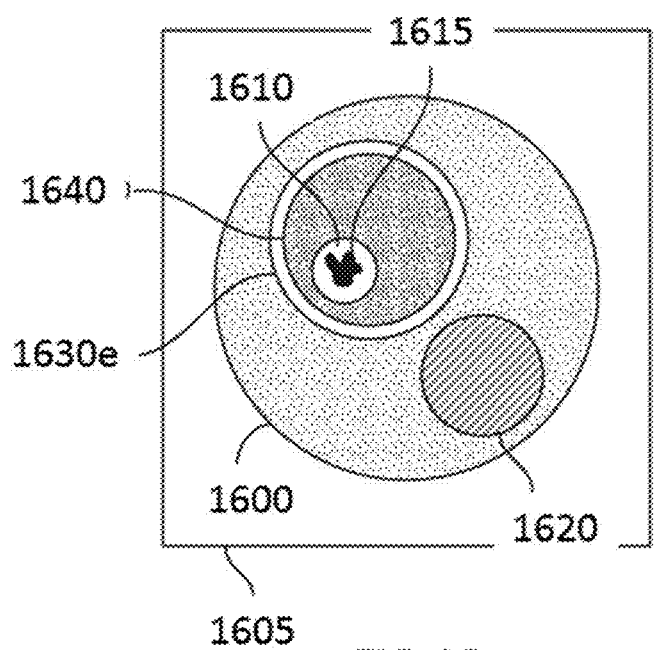
FIG. 16 shows a droplet containing a cell bead in its own droplet and a barcode bead produced using the method of FIG. 15.

FIG. 16 shows a droplet containing a single cell bead and a single barcode bead produced using the method 1500. An external droplet 1600 of aqueous liquid is formed inside a first volume 1605 of a liquid that is immiscible with the aqueous liquid. The external droplet contains a single barcode bead 1620. Within the external droplet is an internal droplet 1640 of aqueous liquid that comprises a cell bead. The internal droplet is partitioned from the external droplet by a second volume 1630e of a liquid that is immiscible with the external droplet and internal droplet. The internal droplet contains a single cell 1610, encapsulated within the cell bead, containing one or more macromolecular constituents 1615.

Figure 17:
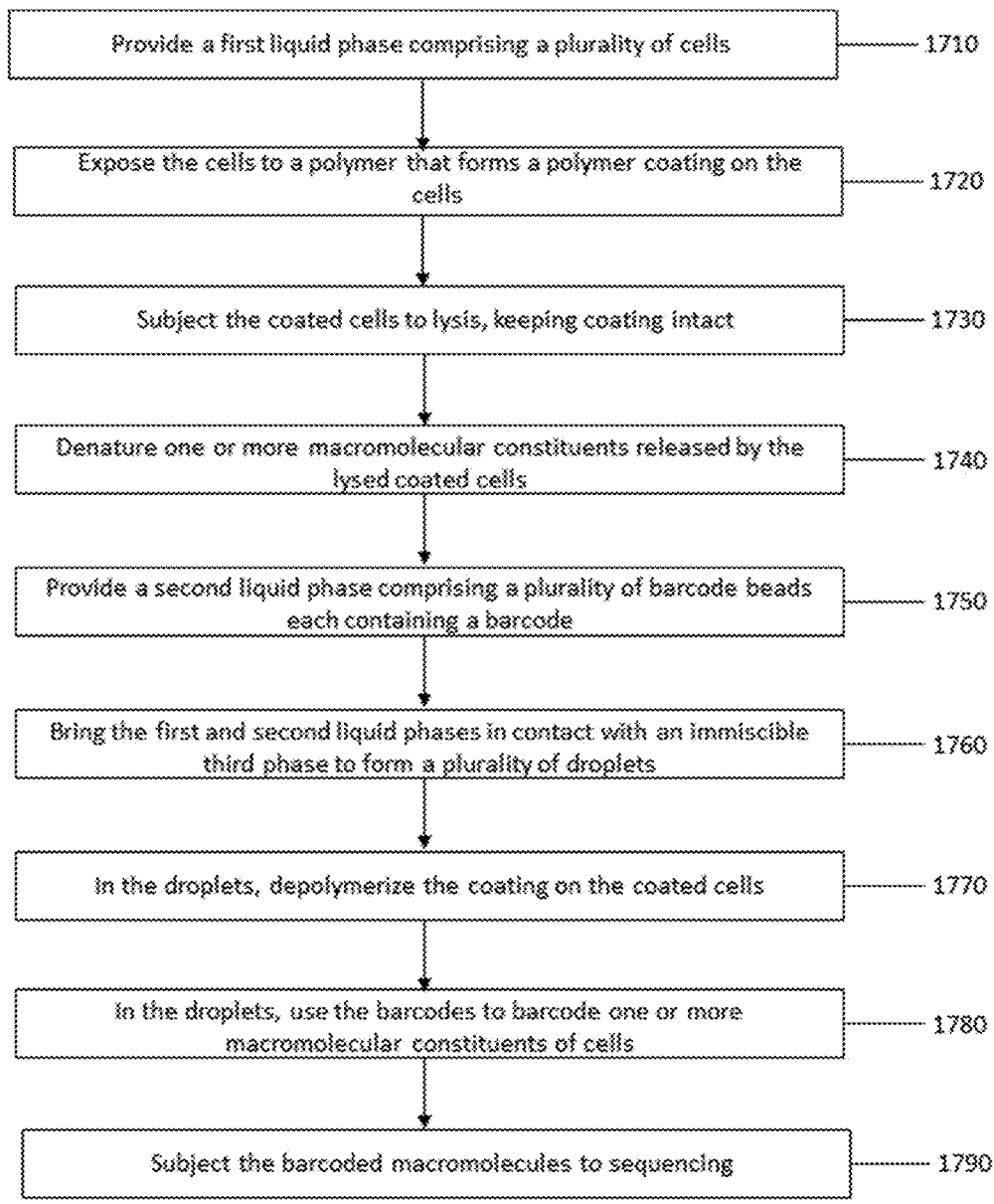
FIG. 17 shows a flowchart for a method of producing droplets containing a coated cell and a barcode bead and generating sequence reads from macromolecular components the coated cell.

FIG. 17 shows a flowchart depicting an example method 1700 of producing droplets containing a cell bead, in the form of a polymer-coated cell, and a barcode bead (e.g., a gel bead) and generating sequence reads from macromolecular components of a cell associated with the cell bead. In some cases, the method 1700 may comprise the following operations.

In operation 1710, a first liquid phase comprising a plurality of cells is provided. The first liquid phase may be aqueous. The first liquid phase may comprise a cellular growth medium. The first liquid phase may comprise a minimal growth medium.

In operation 1720, the cells can be exposed to a polymer that selectively associates with the cells to form a coating on the cells. The polymer may be electrically charged. The polymer may comprise a cation. The polymer may comprise a polycation. The coating may be formed by electrostatic interactions between the cells and the charged polymer. The polymer may be cholesterol. The polymer may be a lipid-modified copolymer. The coating may be formed by hydrophobic interactions between the cells and the polymer. The polymer may be a protein-modified copolymer. The coating may be formed by protein interactions between surface antigens of the cells and the protein-modified copolymer. The coating may comprise one or more layers of coating. The coating may be diffusively permeable to chemical or biochemical reagents. The coating may be diffusively impermeable to macromolecular constituents of the cells. In this manner, the coating may act to allow the coated cells to be subjected to chemical or biochemical operations while spatially confining the macromolecular constituents to a region encapsulated by the coating. The coating may comprise any other polymer capable of interacting with the cells.

In operation 1730, the coated cells can be subjected to conditions sufficient to lyse the cells. In some examples, lysis is completed with the aid of a lysis agent in a droplet. In some cases, lysis of coated cells is completed in bulk. The lysis of the cells may occur subsequent to subjecting the cells to conditions sufficient to encapsulate the cells in the polymer coating. The lysis may release macromolecular constituents of the lysed coated cells. Though, the coating of the cells may retain the macromolecular constituents released from the cells within the confines of the coating. The lysis may be achieved by exposing the coated cells to sodium hydroxide (NaOH), potassium hydroxide (KOH), or any other alkaline agent. The lysis may be achieved by exposing the coated cells to a detergent, such as sodium dodecyl sulfate (SDS), 4-(1,1,3,3-Tetramethylbutyl)phenyl-polyethylene glycol (TRITON X-100) or any non-ionic surfactant, or a saponin. The lysis may be achieved by exposing the coated cells to an enzyme, such as a proteinase or a lytic enzyme (such as a lysozyme, cellulose, or zymolase). The lysis may be achieved by exposing the coated cells to freeze thawing. The lysis may be achieved by exposing the coated cells to electromagnetic radiation, such as ultraviolet (UV) light. The lysis may be achieved by exposing the coated cells to heat. The lysis may be achieved by exposing the coated cells to any other lysis agent. The lysis may occur subsequent to forming a coating of the coated cells.

In operation 1740, the lysed coated cells can be subjected to conditions sufficient to denature one or more macromolecular constituents released by the lysed coated cells. In some examples, denaturation is completed with the aid of a denaturation agent in a droplet. In some cases, denaturation is completed in bulk. The denaturing may be achieved by exposing the coated cells to sodium hydroxide (NaOH). The denaturing may be achieved by exposing the coated cells to any other denaturing agent. In some examples, operation 1740 is completed contemporaneous to operation 1730. In some examples, a denaturing agent can both denature macromolecular constituents and lyse the coated cells.

In operation 1750, a second liquid phase comprising a plurality of barcode beads can be provided. The second liquid phase may be aqueous. The second liquid phase may comprise a cellular growth medium. The second liquid phase may comprise a minimal growth medium. The barcode beads each contain a barcode to barcode one or more macromolecular constituents of the plurality of coated cells. In some cases, the first liquid phase and the second liquid phase are the same phase. In some cases, the first liquid phase and the second liquid phase are mixed to provide a mixed phase.

In operation 1760, the first liquid phase and the second liquid phase are brought together with a third liquid phase that is immiscible with the first and second liquid phase. The third liquid phase may interact with the first and second liquid phases in such a manner as to partition each of the plurality of coated cells and the plurality of barcode beads into a plurality of droplets. The third liquid phase may comprise an oil and may also comprise a surfactant. The third liquid phase may comprise a fluorinated hydrocarbon. In some cases, a given droplet may include a single coated cell and a single barcode bead. In some cases, at least 80%, at least 90%, at least 95%, at least 99%, at least 99.5%, at least 99.9%, at least 99.95%, or at least 99.99% of the droplets may contain a single coated cell.

In operation 1770 and in the droplets, the coated cells are subjected to conditions sufficient to depolymerize the coating. The depolymerization of the coating may be achieved by exposing the coated cells to a reducing agent (e.g., dithiothreitol (DTT)), which may be in a partition. The depolymerization of the coating may be achieved by exposing the coated cells to any substance capable of depolymerizing the coating. In some cases, operation 1770 also includes releasing barcodes from the barcode beads, which may be achieved with the same stimulus, such as, for example, used to reverse cross-linking of the coated cell. In some cases, the stimuli are different. Released barcodes can then participate in barcoding as in operation 1780.

In operation 1780, the barcode is used to barcode one or more macromolecular constituents of a given cell in a given droplet. In some cases, the macromolecular constituents of the cell is subjected to conditions sufficient for nucleic acid amplification for barcoding. In such cases, a barcode can function as a primer in such amplification. In other cases, ligation can be used for barcoding. In some cases, the barcode is used to identify one or more macromolecular constituents of the cell. In some cases, the barcode is subjected to nucleic acid sequencing to identify one or more macromolecular components. In some cases, the sequencing is untargeted sequencing. In some cases, the sequencing is targeted sequencing.

In operation 1790, the barcoded macromolecules (or derivatives thereof) are subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell from which the barcoded sequencing read was generated. Such capability can link particular sequences to particular cells. Additional details and examples regarding nucleic acid sequencing methods are described elsewhere herein.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets.

Figure 18:
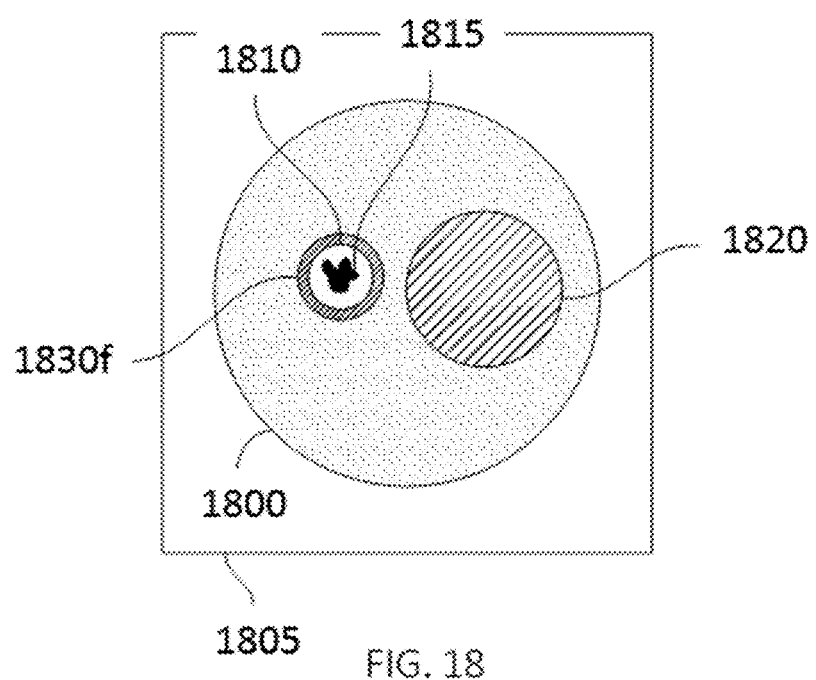
FIG. 18 shows a droplet containing a coated cell and a barcode bead produced using the method of FIG. 17.

FIG. 18 shows a droplet containing a single coated cell and a single barcode bead produced using the method 1700. A droplet 1800 of aqueous liquid is formed inside a volume 1805 of a liquid that is immiscible with the aqueous liquid. The droplet contains a single barcode bead 1820. The droplet also contains a single coated cell 1810 containing one or more macromolecular constituents 1815. The coated cell is surrounded by a coating 1830f.

Figure 19:
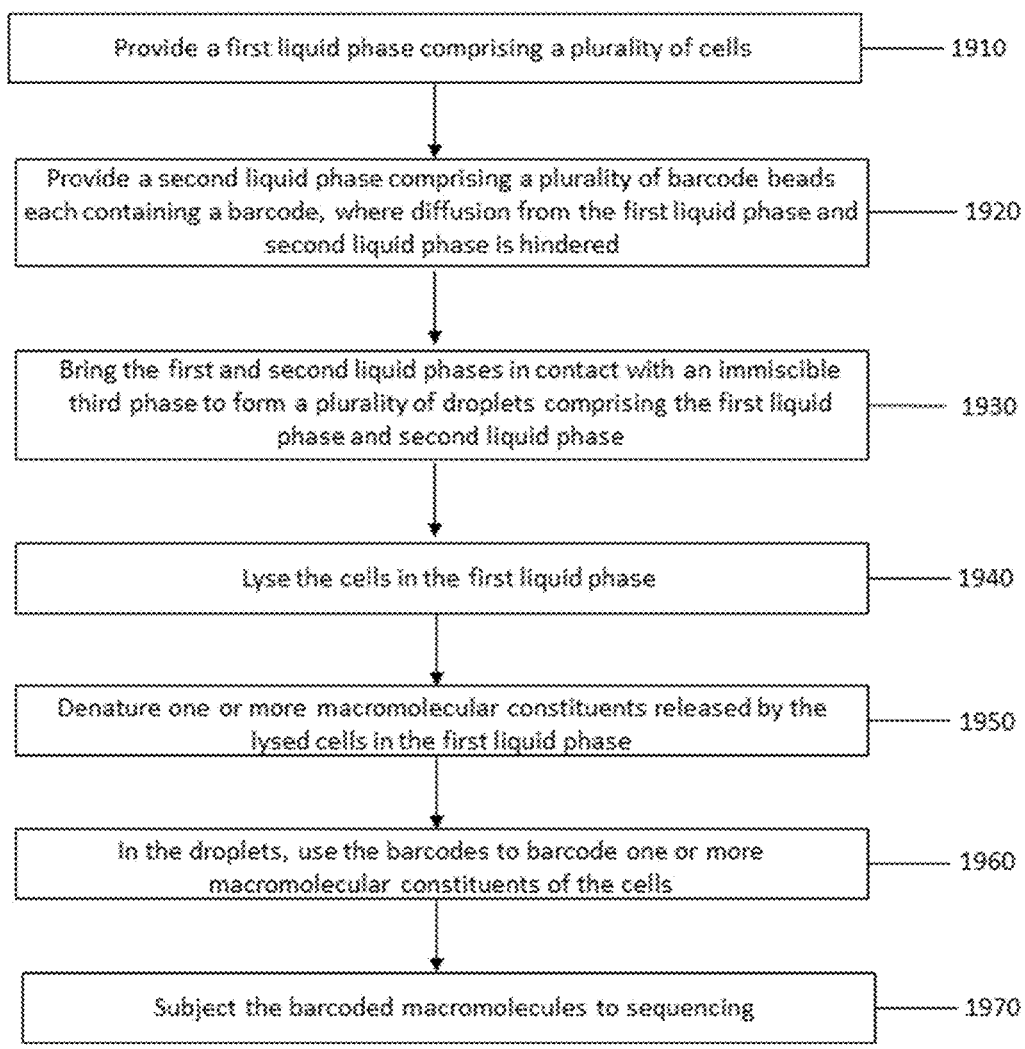
FIG. 19 shows a flowchart for a method of producing droplets containing a cell and barcode bead and generating sequence reads from macromolecular components of the cell.

FIG. 19 shows a flowchart that depicts an example method 1900 of producing droplets containing cell and a single barcode bead and generating sequence reads from macromolecular components of the cell. In this example, a droplet comprising aqueous fluids having different viscosities can segregate an included cell to particular regions within the droplet. In this example, two miscible phases are provided in the droplet, but which two miscible phases are of sufficiently different physical properties (e.g., have substantially different viscosities) that diffusion between the two phases is limited. In some examples, the two miscible phases are phases of an aqueous two phase system (ATPS). Examples of such two miscible phases include an aqueous phase and an aqueous phase comprising one or more of glycerol, ficoll, dextran and polyethylene glycol (PEG). In this manner, incompatible chemical or biochemical reagents may be sequestered into the different phases. Additionally, the slowed diffusion may allow for the timed exposure of the cell in the droplet or barcode bead to chemical or biochemical reagents. In some cases, the method 1900 may comprise the following operations.

In operation 1910, a first liquid phase comprising a plurality of cells is provided. The first liquid phase may be aqueous. The first liquid phase may comprise a cellular growth medium. The first liquid phase may comprise a minimal growth medium. In some examples, the first liquid phase may comprise one of two miscible liquid phases between which two liquid phases diffusion of molecules from one phase to the other is limited. For example the first liquid phase may comprise one component of an ATPS or may comprise one or more viscosity enhancing agents, such as glycerol, ficoll, dextran or polyethylene glycol (PEG).

In operation 1920, a second liquid phase comprising a plurality of barcode beads can be provided. The second liquid phase may be aqueous. In some examples, the second liquid phase may be the other component of the ATPS described above or may not include a viscosity enhancing agent, such as glycerol, ficoll, dextran and polyethylene glycol (PEG). The second liquid phase may comprise a cellular growth medium. The second liquid phase may comprise a minimal growth medium. The barcode beads each contain a barcode to barcode one or more macromolecular constituents of the plurality of cells.

In operation 1930, the first liquid phase and the second liquid phase are brought together with a third liquid phase that is immiscible with the first and second liquid phase. The third liquid phase may interact with the first and second liquid phases in such a manner as to partition each of the plurality of cells and the plurality of barcode beads into a plurality of droplets. The third liquid phase may comprise an oil and may comprise a surfactant. The third liquid phase may comprise a fluorinated hydrocarbon. In some cases, a given droplet may include a single cells and a single barcode bead. In some cases, at least 80%, at least 90%, at least 95%, at least 99%, at least 99.5%, at least 99.9%, at least 99.95%, or at least 99.99% of the droplets may contain a single cell.

In operation 1940, the cells are subjected to conditions sufficient to lyse the cells. In some examples, lysis is achieved via the aid of a lysis agent present in the first liquid phase within a droplet. The lysis may release macromolecular constituents of the lysed cells. However, given the difference in viscosities between the two fluids of the droplets, diffusion of these macromolecular constituents may be limited. The lysis may be achieved by exposing the cells to sodium hydroxide (NaOH), potassium hydroxide (KOH), or any other alkaline agent, which may be in the droplet. The lysis may be achieved by exposing the cells to a detergent, such as sodium dodecyl sulfate (SDS), 4-(1,1,3,3-Tetramethylbutyl)phenyl-polyethylene glycol (TRITON X-100) or any non-ionic surfactant, or a saponin, which may be in the droplet. The lysis may be achieved by exposing the cells to an enzyme, such as a proteinase or a lytic enzyme (such as a lysozyme, cellulose, or zymolase), which may be in the droplet. The lysis may be achieved by exposing the cells to freeze thawing. The lysis may be achieved by exposing the cells to electromagnetic radiation, such as ultraviolet (UV) light. The lysis may be achieved by exposing the cells to heat. The lysis may be achieved by exposing the cells to any other lysis agent.

In operation 1950, the lysed cells can be subjected to conditions sufficient to denature one or more macromolecular constituents released by the lysed cells. In some cases, denaturation is completed via the aid of a denaturation agent present in the first liquid phase within a droplet. The denaturing may be achieved by exposing the cells to sodium hydroxide (NaOH), which may be in the droplet. The denaturing may be achieved by exposing the cells to any other denaturing agent, which may be in the droplet. In some examples, operation 1950 is completed contemporaneous to operation 1940. In some examples, a denaturing agent can both denature macromolecular constituents and lyse the cells.

In operation 1960, the barcodes are used to barcode one or more macromolecular constituents of a given cell in a given droplet. Barcoding can be timed by the limited diffusion of the macromolecular constituents between the two phases within the droplet. After sufficient time has passed for mixing of the macromolecular constituents with barcode beads, barcoding can proceed. In some cases, the macromolecular constituents are subjected to conditions sufficient for nucleic acid amplification for barcoding. In such cases, a barcode can function as a primer in such amplification. In other cases, ligation may be used for barcoding. In some cases, barcodes are used to identify one or more macromolecular constituents of the cells. In some cases, barcodes are subjected to nucleic acid sequencing to identify one or more macromolecular components. In some cases, the sequencing is untargeted sequencing. In some cases, the sequencing is targeted sequencing. In some cases, operation 1960 also includes releasing barcodes from the barcode beads, which may be achieved with a stimulus such as a reducing agent (e.g. DTT). Released barcodes can then participate in barcoding.

In operation 1970, the barcoded macromolecules (or derivatives thereof) are subjected to sequencing to generate reads. The sequencing may be performed within a droplet. The sequencing may be performed outside of a droplet. For instance, the sequencing may be performed by releasing the barcoded macromolecules from a droplet and sequencing the barcoded macromolecules using a sequencer, such as an Illumina sequencer or any other sequencer described herein. In some cases, a given barcoded sequencing read can be used to identify the cell from which the barcoded sequencing read was generated. Such capability can link particular sequences to particular cells. Additional details and examples regarding nucleic acid sequencing methods are described elsewhere herein.

Figure 20:
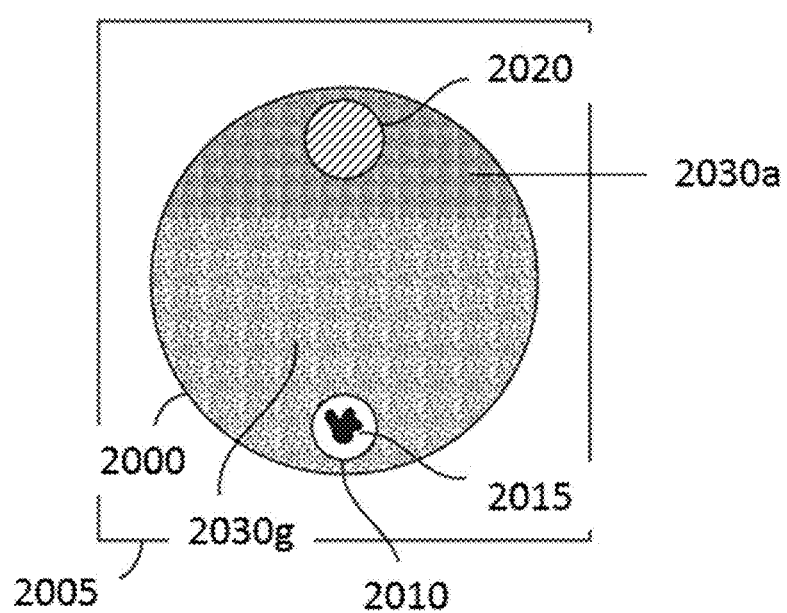
FIG. 20 shows a droplet containing a cell and a barcode bead produced using the method of FIG. 19.

In some cases, prior to sequencing, the barcoded macromolecules may be further processed. For example, the barcoded macromolecules are subjected to nucleic acid amplification (e.g., PCR) prior to sequencing. In some cases, additional sequences are ligated to barcoded macromolecules. Such further processing may be performed in a droplet or external to the droplet, such as by releasing the barcoded macromolecules from the droplets. FIG. 20 shows a droplet containing a single cell and a single barcode bead produced using the method 2000. A droplet 2000 of aqueous liquid is formed inside a volume 2005 of a liquid that is immiscible with the aqueous liquid. The droplet contains a single gel bead 2020. The droplet also contains a single cell 2010 containing one or more macromolecular constituents 2015. The droplet also contains two different aqueous phases that separately confine the barcode bead 2020 and the cell 2010. Phase 2030$g$ comprises the cell 2010 and phase 2030$a$ comprises the barcode bead 2020.

The disclosure also provides compositions, systems and methods for generating cell beads in cell beads. Such methods, compositions and systems can be useful for positioning cells encapsulated in cell beads at the center or substantially at the center of the cells beads. In some cases, centering of a cell can prevent the contents of the cell beads (e.g., cells, components of cells, biomolecules derived from cells, nucleic acids from cells) from diffusing or leaking out of the cell bead. Loss of these materials can lead to partial or complete loss of the sequencing information for the contents of a given cell bead. For example, leakage of nucleic acids from cells at the edges of cell beads can lead to noisy profiles derived from sequencing and/or potential false positive calls. By centering cells within cell beads, a greater depth of cell bead material encapsulates cells, providing a larger diffusion distance and, thus, greater diffusion barrier for diffusion of encapsulated materials. Moreover, a cell bead in cell bead approach, itself, adds additional material that surrounds the cell, also resulting in a greater diffusion barrier. In general, cell beads in cell beads can be generated by a similar process used to generate single gel beads, as described elsewhere herein. First order cell beads can be generated as described herein, and then subjected to the same process for cell bead generation again to generate cell beads in cell beads.

Figure 27:
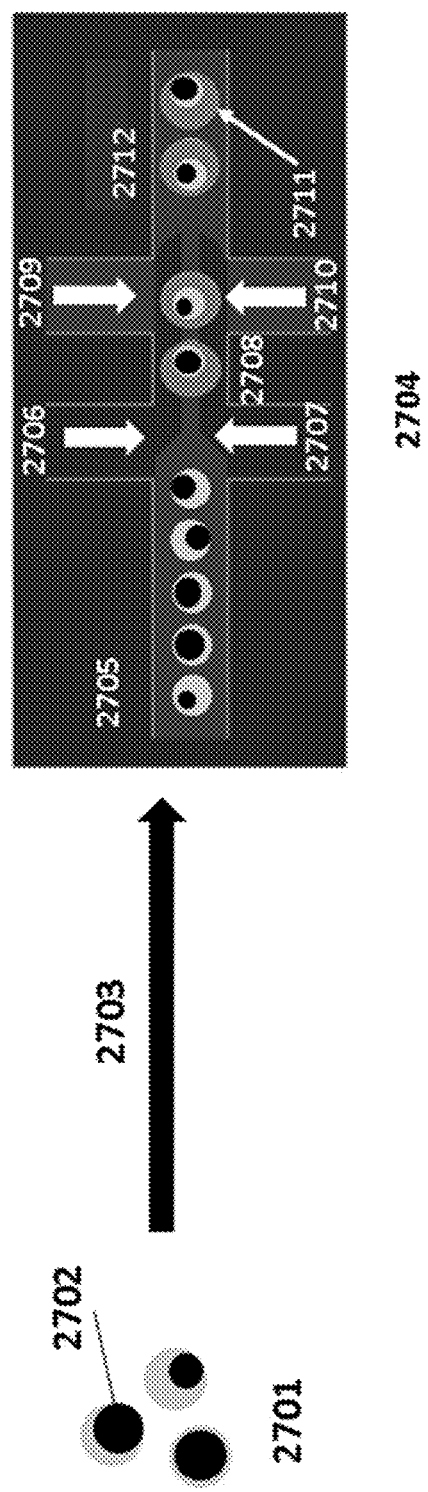
FIG. 27 schematically depicts an example method for generating a cell bead in cell bead.

An example method and microfluidic device architecture for generating cell beads in cell beads are schematically depicted in FIG. 27. As shown in FIG. 27, cell beads 2701, which contain cells 2702 may be generated in any suitable manner, including in a manner described herein, are provided in an aqueous phase. The cell beads 2701 are then provided 2703 to a microfluidic device 2704. The device comprises microfluidic channels arranged in a double-cross configuration. The cell beads 2701 are provided to the microfluidic device where they flow in a first channel 2705 of the microfluidic device 2704 to a first channel intersection with second and third channels 2706 and 2707. The second and third channels 2706 and 2707 provide polymeric or gel precursors that come together with the stream of cell beads 2701 from the first microfluidic channel 2705.

The stream comprising the cell beads 2701 and polymeric or gel precursors then flows through a fourth microfluidic channel 2708 to a second channel intersection with fifth and sixth channels 2709 and 2710. The fifth and sixth channels provide a phase immiscible with the aqueous phase of cell beads 2701 and polymeric or gel precursors flowing in channel 2708. The stream comprising the cell beads 2701 and polymeric or gel precursors from the fourth channel 2708 flows into the immiscible stream such that droplets 2711 comprising cell beads and polymeric or gel precursors are generated and flow away from the second intersection in a seventh channel 2712. The droplets 2711 can then be subject to conditions suitable for polymerizing or gelling the precursors in the droplets 2711 and subject to solvent exchange as is described elsewhere herein and the resulting cell beads in cell beads recovered.

Figure 28A:
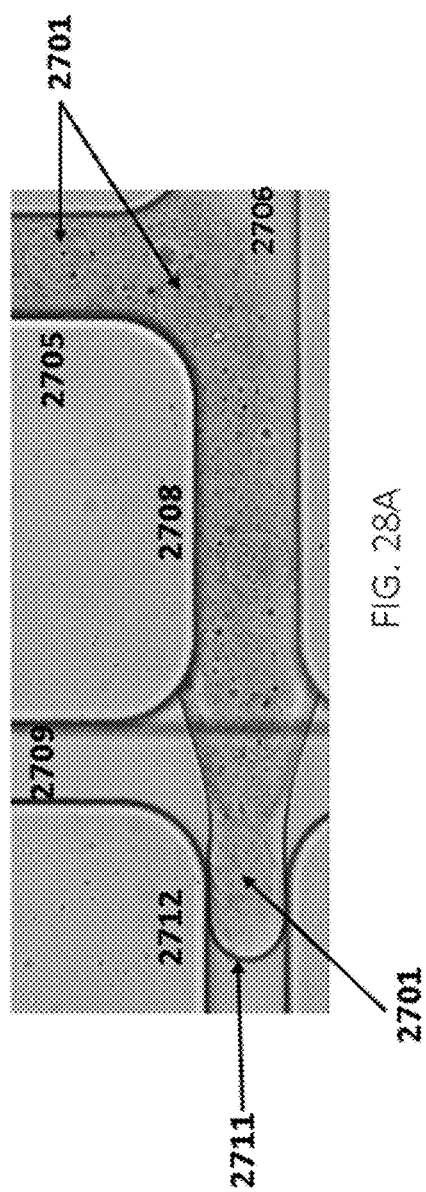
FIGS. 28A and 28B are photographs showing example generation of a cell bead in cell bead.

A photograph showing generation of droplets comprising cell beads and polymeric or gel precursors using a microfluidic device, similar to that shown schematically in FIG. 27, is shown in FIG. 28A. As shown an aqueous phase comprising cell beads 2701 provided from channel 2705 is provided to a first channel junction, into which aqueous phase polymeric or gel precursors flow from channel 2706. The resulting aqueous mixture, comprising both cell beads 2701 and polymeric or gel precursors, flows through channel 2708 into a second channel junction, into which oil provided by channel 2709 flows. The interaction between oil and aqueous phases generates droplets 2711 that comprise a cell bead 2701 and polymeric or gel precursors that flow away from the second channel junction in channel 2712.

Figure 28B:
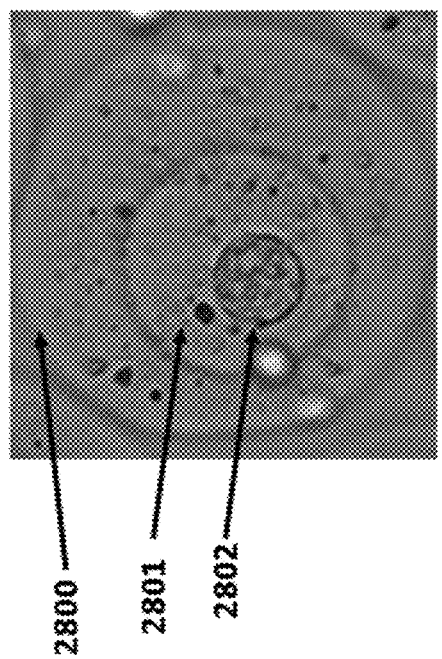

FIG. 28B shows a photograph of a cell bead in cell bead generated from droplets generated in FIG. 28A. The cell bead in cell bead comprises a larger cell bead 2800 that encapsulates a smaller cell bead 2801. The smaller cell bead 2801 encapsulates a cell 2802. As shown in FIG. 28B, the cell 2802 is substantially centered within the larger cell bead 2800.

Figure 29:
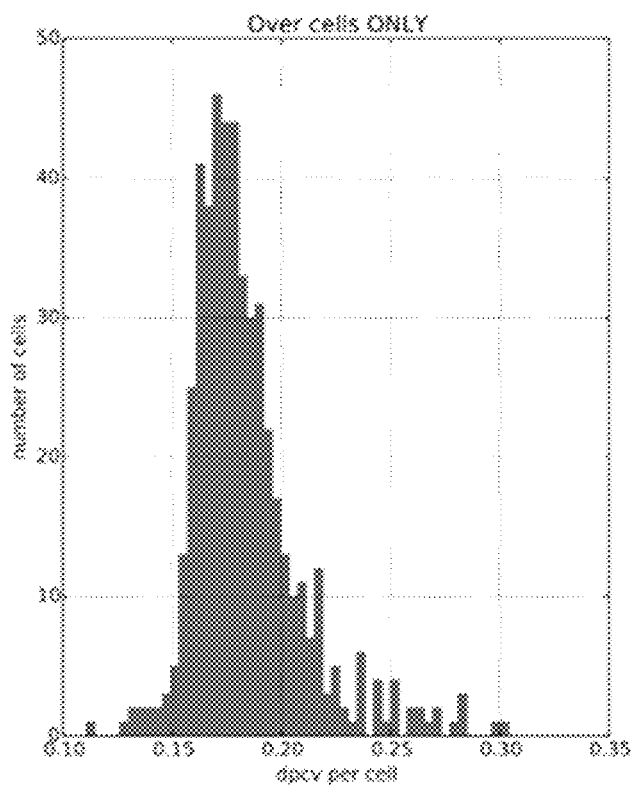
FIG. 29 depicts example sequencing data obtained from samples prepared in a cell bead in cell bead approach.

FIG. 29 shows a histogram of Depth Positional Coefficient of Variation (DPCV) values across individual cells, whose nucleic acids were sequenced using a cell bead in cell bead sample preparation approach. DPCV is a measure of the evenness of sequencing coverage achieved across the position of the genome.

Additionally, cells may be centered in droplets without the generation of a cell bead comprising a cell bead. For example, droplets comprising polymeric or gel precursors and cells may be subjected to shearing prior to cell bead generation. Shearing may be achieved, for example, via orbital shaking or in a microfluidic channel. In such cases, the kinetics of polymerization or gelation of the precursors can be controlled such that polymerization or gelation is sufficiently slow or delayed. Slower or delayed polymerization or gelling can permit internal circulation of droplet contents that can center a cell within a droplet, such that it can then be fixed in place at the center of a cell bead upon precursor polymerization or gelling.

Figure 30:
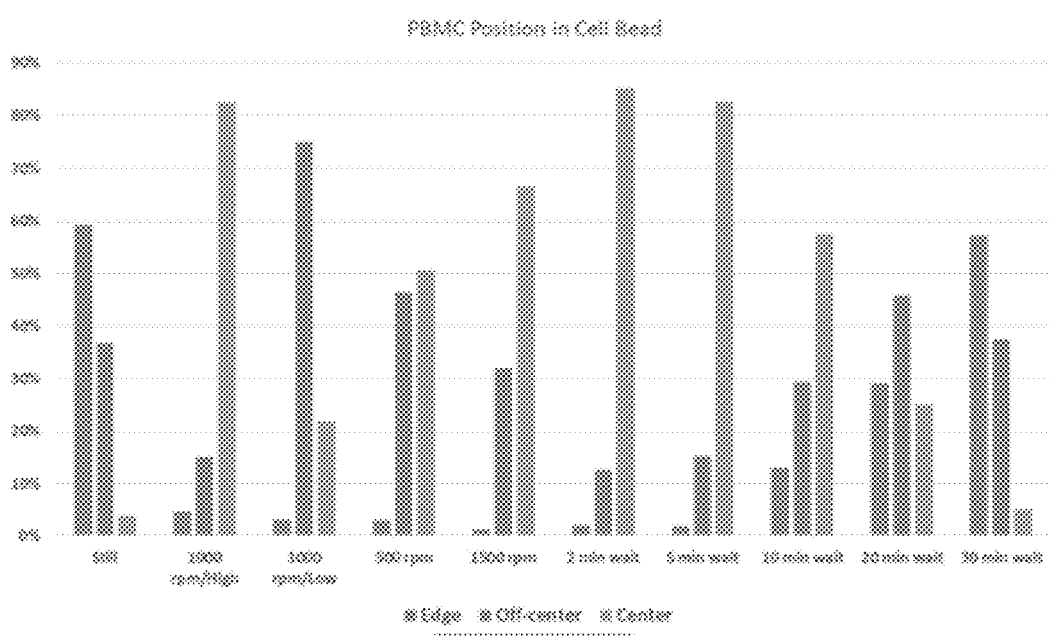
FIG. 30 depicts example data depicting centering of a cell in a cell bead in cell bead using different orbital shaking conditions.

FIG. 30 depicts a bar plot showing different categories of cell beads as a function of example conditions used to make the cell beads. The cell beads were classified into three categories (edge, off-center, center) depending on the location of a cells with respect to either the edge or the center of a given cell bead. The cell beads were generated with varying time and speed of shaking on an orbital shaker, as is discussed above.

Furthermore, cells may also be centered in droplets by forming core-shell beads, with cells suspended in the solution that forms the core. Cells may be formed by viscosity-mismatched flowing streams such that cells are suspended in a core fluid having a different viscosity than a shell fluid. The shell fluid may be liquid and/or formed from a cross-linked matrix such as a cross-linked polymer. Examples of such core-shell beads are described in Rossow et al., *J. Am. Chem. Soc.* 2012, 134, 4983-4989, which is incorporated herein by reference.

Core-shell beads having cells suspended in the cores may also be formed through the generation of aqueous-in-aqueous droplets made from aqueous two-phase systems. For example, the cells are suspended in a core solution (e.g., a polymer core solution, a polyethylene glycol (PEG) core solution) that is then surrounded by a cross-linked shell (e.g., cross-linked dextran shell). This bead may be generated from aqueous-in-aqueous droplets with one aqueous phase comprising cross-link precursors and another aqueous phase comprising cells. Additional details regarding the formation of core-shell beads from aqueous two-phase systems are provided in Mytnyk et al., *RSC Adv.*, 2017, 7, 11331-11337, which is incorporated herein by reference.

Many variations, alterations and adaptations based on the disclosure provided herein are possible. For example, the order of the operations of one or more of the example methods 700, 900, 1000, 1100, 1300, 1500, 1700, 1900, and 2500 discussed above can be changed, some of the operations removed, some of the operations duplicated, and additional operations added as appropriate. Some of the operations can be performed in succession. Some of the operations can be performed in parallel. Some of the operations can be performed once. Some of the operations can be performed more than once. Some of the operations can comprise sub-operations. Some of the operations can be automated and some of the operations can be manual. The processor as described herein can comprise one or more instructions to perform at least a portion of one or more operations of one or more of the methods. Moreover, while these examples are described above with respect to cell analysis, the same procedures can be extended to other biological species containing macromolecular constituents that can be barcoded, including viruses.

Also disclosed herein are systems for cell analysis, including via a cell bead. The systems may utilize a droplet generator (e.g., a microfluidic device, droplet generators having a T-junction, droplet generators that generate droplets with cross-channel flow focusing, droplet generators that generate droplets with step/edge emulsification, droplet generations that generate droplets with gradient generation, droplet generators that use piezo/acoustics for droplet generation).

In some cases, a droplet generator is a microfluidic device which includes mixing of immiscible fluids at channel junctions of one or more channels to form droplets. The channels may be microchannels. The microchannels may be implemented on microfluidic devices. Examples of such microfluidic devices and their operation are provided in FIG. 1B, FIG. 1C, FIG. 1D, and FIG. 31 and are described elsewhere herein.

Such systems may also include a controller programmed to implement a method described herein, including one of the example methods 100, 700, 900, 1000, 1100, 1300, 1500, 1700, 1900, and 2500 described herein.

Computer Control Systems

Figure 6:
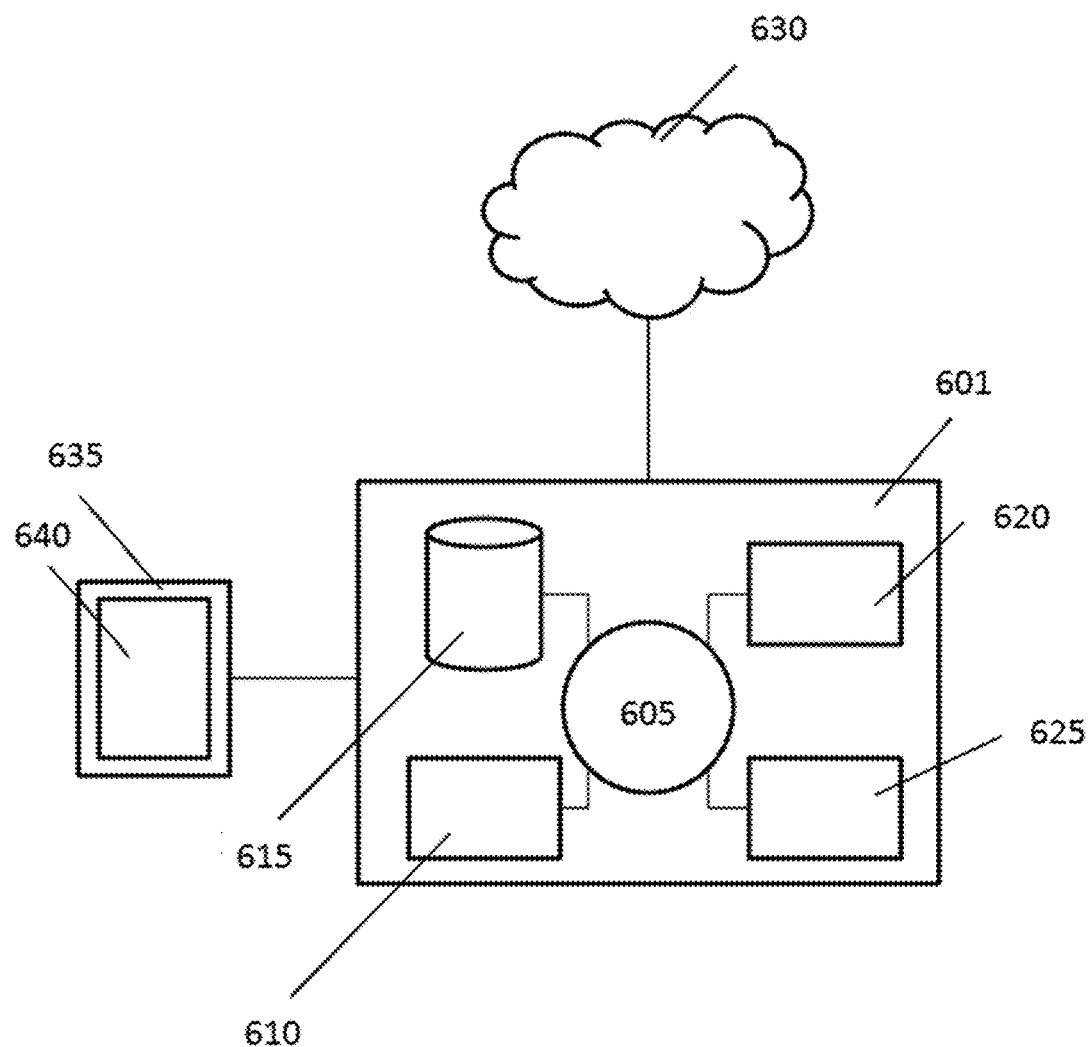
FIG. 6 shows an example computer control system that is programmed or otherwise configured to implement methods provided herein.

The present disclosure provides computer control systems that are programmed to implement methods of the disclosure. FIG. 6 shows a computer system 601 that is programmed or otherwise configured to implement methods or parts of methods described herein, including example methods 100, 700, 900, 1000, 1100, 1300, 1500, 1700, 1900, and 2500. The computer system 601 can regulate various aspects of the present disclosure, such as, for example, sample preparation of cellular materials in cell beads, barcoding of these materials and/or analysis of barcoded molecules. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, implement methods or parts of methods described herein, including example methods 100, 700, 900, 1000, 1100, 1300, 1500, 1700, 1900, and 2500.

EXAMPLES

Example 1: Detection of Infectious Agents

The systems and methods described herein may be used to detect infectious agents in cells. For instance, the systems and methods may be used to collect CD4 T-cells in droplets and subject the collected CD4 T-cells to nucleic acid sequencing. For CD4 T-cells obtained from an HIV-infected subject, the nucleic acid sequencing may reveal the presence of HIV-derived nucleic acids in the cells. The extent to which the HIV infection has spread in an HIV-infected subject may be measured by collecting and performing nucleic acid sequencing on all CD4 T-cells obtained from the HIV-infected subject. The systems and methods may be used to detect any infections agents in cells.

The systems and methods may be used to detect co-infections by two or more infectious agents in cells. In an example, a subject's cells may be collected in droplets and subjected to nucleic acid sequencing. The nucleic acid sequencing may reveal the presence of two or more infectious agent-derived nucleic acids in the cells. Alternatively or in combination, the cells collected in droplets may be subjected to an antibody-based multiple assay. The multiple assay may reveal the presence of two or more infectious agents.

Example 2: Preparation of Long DNA Reads

The systems and methods described herein may be utilized to retain long nucleic acid segments for producing long sequencing reads while removing short nucleic acid segments. The retention of long nucleic acid segments and removal of short nucleic acid segments may enhance the accuracy or speed of nucleic acid sequencing technologies, such as those nucleic acid sequencing technologies described herein.

Figure 23:
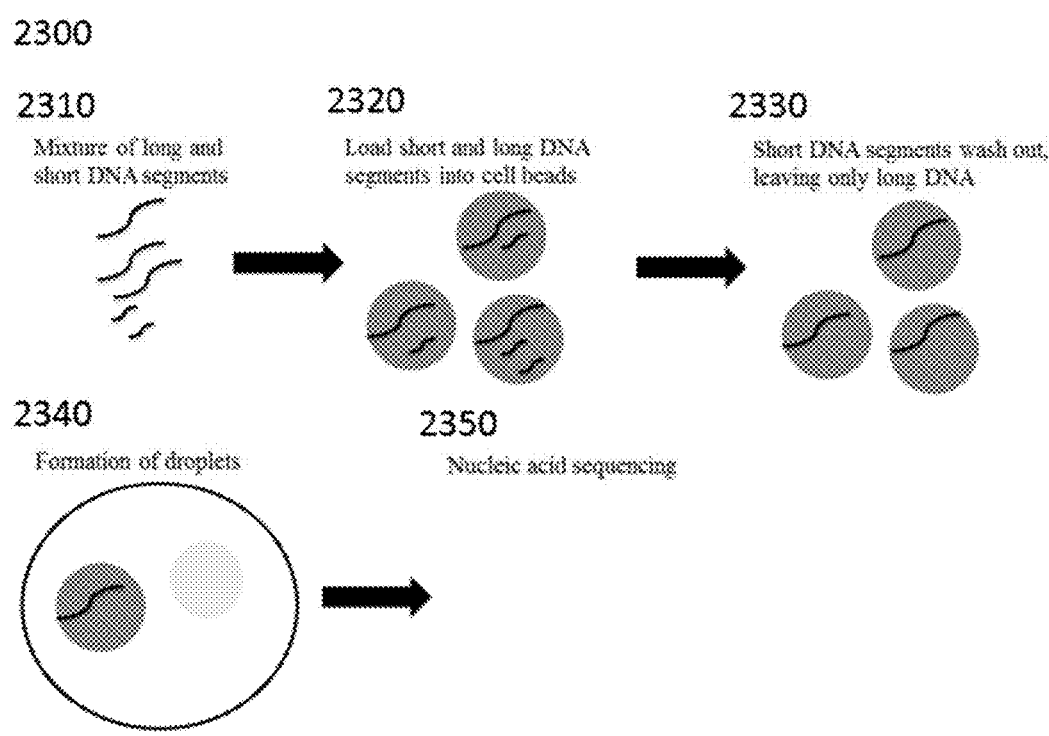
FIG. 23 shows a schematic of an example method for retaining long nucleic acid segments and removing short nucleic acid segments.

FIG. 23 shows a schematic depicting an example method 2300 for retaining long nucleic acid segments and removing short nucleic acid segments.

In a first operation 2310, a mixture of short and long DNA segments is collected.

In a second operation 2320, the mixture of long and short DNA segments is loaded into cell beads. The mixture may be loaded into the cell beads by any of the systems and methods described herein. The mixture may be loaded into the cell beads such that some cell beads enclose a mixture of short nucleic acid segments and long nucleic acid segments.

In a third operation 2330, the cell beads are washed. During washing, the short nucleic acid segments are washed out of the cell beads, such that the cell beads retain the long nucleic acid segments. Cell beads can be tailored to have porosity that traps longer nucleic acid segments within cell beads but allows shorter nucleic acid segments to diffuse or flow out of the cell beads.

In a fourth operation 2340, the cell beads containing long nucleic acid segments are combined with gel beads to form droplets containing one or more cell beads and one or more gel beads.

In a fifth operation 2350, the DNA segments are subjected to nucleic acid sequencing, as described herein.

Although described herein with respect to nucleic acids, the method 2300 may be used to generate droplets containing long segments of any macromolecules described herein. For instance, the method 2300 may be used to generate droplets containing long protein segments.

Example 3: Amplification of Specific Nucleic Acid Loci

Figure 24:
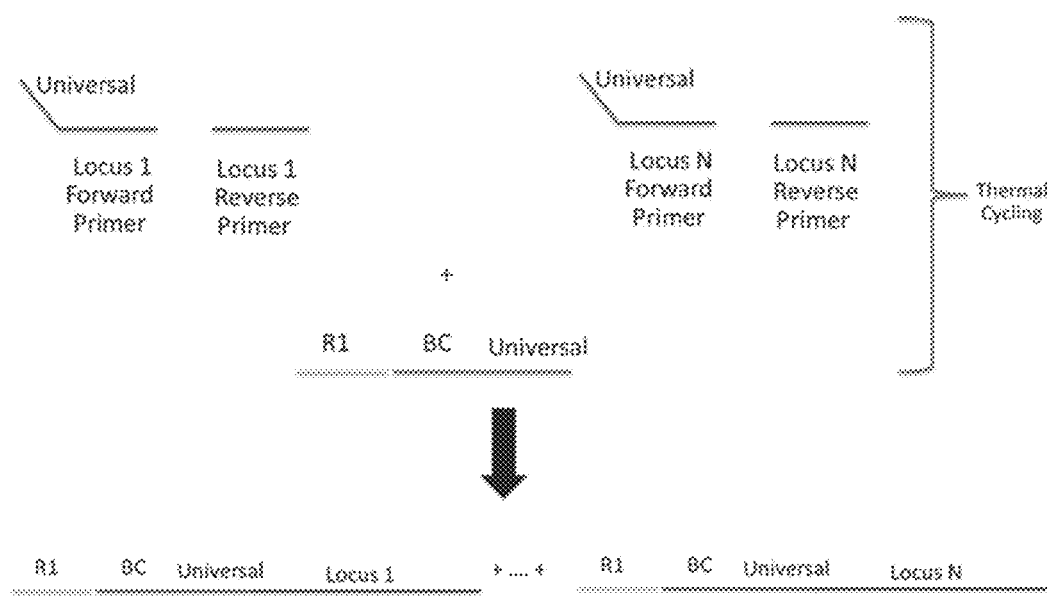
FIG. 24 shows a schematic of an example method for the amplification and barcoding of nucleic acid loci from a cell bead.

The systems and methods described herein may be used in the amplification and barcoding of targeted sequences, such as nucleic acid (e.g. DNA) loci. These nucleic loci may be derived from nucleic acids that are associated with or encapsulated within a cell bead. Moreover, amplification may be performed in an individual partition among a plurality of partitions, such as a droplet among a plurality of droplets. Where partitions are implemented, an individual partition may comprise a cell bead having the nucleic acid(s) to be amplified. In some cases, amplification of nucleic acid(s) of a cell bead may be completed prior to partitioning. FIG. 24 shows an example process for amplifying and barcoding targeted nucleic acid sequences.

During a first stage of amplification, the forward primers hybridize with their respective loci where present and are extended via the action of the polymerase and, in some cases, with the aid of thermal cycling. The resulting constructs (not shown in FIG. 24) comprise both the universal nucleic acid sequence and complementary sequences of target loci present. In a second stage of amplification, the reverse primers hybridize to the complementary sequences of the target loci generated in the first stage and are extended to generate constructs (not shown in FIG. 24) comprising the original loci sequences and a complementary sequence of the universal nucleic acid sequence. In some cases, the constructs generated in the second stage are shorter in length than those generated in the first round, such that the sequences derived from the nucleic acids analyzed that are present in these constructs are the target loci sequences.

Next, barcoded nucleic acid molecules, shown in FIG. 24, comprising an R1 primer sequence (e.g., primer for sequencing), a barcode sequence (BC), and the universal nucleic acid sequence are provided. The barcoded nucleic acid molecules may be coupled to beads and/or may be releasable from the beads. In some cases, these beads are partitioned with cell beads in which amplification of target loci has already been completed prior to partitioning. In other cases, these beads are partitioned with cell beads prior to such amplification. Moreover, where releasable from beads, the barcoded nucleic acid molecules can be released from the beads prior to participating in further downstream reactions.

The barcoded nucleic acid molecules can be contacted with the amplified nucleic acids generated above and corresponding to the various loci present. Upon contact, the universal nucleic acid sequence of the barcoded nucleic acid molecules can hybridize with complementary sequences generated in second-stage constructs discussed above. The hybridized barcoded nucleic acid molecules are then extended via the action of a polymerase, such as with the aid of thermal cycling, to generate barcoded constructs comprising the sequences of the barcoded nucleic acid molecules and sequences complementary to the second stage constructs discussed above and corresponding to the original loci sequences analyzed. In some cases, the resulting barcoded constructs can then be further processed to add additional sequences and then subject to sequencing. As shown, amplification schemes described above can generate barcoded, target-specific constructs for sequencing analysis.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing or analyzing one or more components from a cellular sample, comprising:
   (a) providing a plurality of cell beads and a plurality of barcode beads, wherein (i) a cell bead of said plurality of cell beads comprises a cell, wherein said cell comprises a nucleic acid molecule in an interior region of said cell, and (ii) a barcode bead of said plurality of barcode beads comprises a plurality of nucleic acid barcode molecules, wherein nucleic acid barcode molecules of said plurality of nucleic acid barcode molecules comprise a common barcode sequence;
   (b) subjecting said plurality of cell beads to bulk processing, which bulk processing comprises: (i) rendering said nucleic acid molecule accessible to a species external to said interior region and (ii) denaturing said nucleic acid molecule to generate a denatured nucleic acid molecule in said cell bead; and
   (c) partitioning said plurality of cell beads and said plurality of barcode beads into a plurality of partitions, wherein upon partitioning, a partition of said plurality of partitions comprises said cell bead and said barcode bead.

2. The method of claim 1, further comprising performing one or more reactions on said denatured nucleic acid molecule.

3. The method of claim 2, wherein said one or more reactions comprise a reaction selected from the group consisting of nucleic acid extension, nucleic acid amplification, nucleic acid ligation, reverse transcription, and a combination thereof.

4. The method of claim 2, wherein said one or more reactions are performed in said partition.

5. The method of claim 1, further comprising using a nucleic acid barcode molecule from said plurality of nucleic acid barcode molecules and said denatured nucleic acid molecule or a derivative thereof to generate a barcoded nucleic acid molecule comprising a first sequence corresponding to said denatured nucleic acid molecule and a second sequence corresponding to said common barcode sequence.

6. The method of claim 5, further comprising subjecting said barcoded nucleic acid molecule or derivative thereof to sequencing.

7. The method of claim 1, wherein said cell bead is subjected to conditions sufficient to lyse said cell to render said nucleic acid molecule accessible to a species external to said interior region.

8. The method of claim 7, wherein said conditions sufficient to lyse said cell comprise contacting said cell beads with a lysis agent.

9. The method of claim 1, wherein said barcode bead is a gel bead.

10. The method of claim 1, wherein said plurality of partitions is a plurality of droplets.

11. The method of claim 1, wherein said plurality of partitions is a plurality of wells.

12. The method of claim 1, wherein said nucleic acid barcode molecules of said plurality of nucleic acid barcode molecules are attached to said barcode bead.

13. The method of claim 1, wherein said nucleic acid molecule is a genomic deoxyribonucleic acid molecule.

14. The method of claim 5, further comprising recovering said barcoded nucleic acid molecule or said derivative thereof from said partition.

15. The method of claim 9, wherein said gel bead is degradable upon application of a stimulus.

16. The method of claim 15, further comprising degrading said gel bead upon application of said stimulus.

17. The method of claim 15, wherein said stimulus is a chemical or biological stimulus, and wherein said partition comprises said stimulus.

18. The method of claim 15, wherein said stimulus is a reducing agent.

19. The method of claim 1, wherein said cell bead is degradable upon application of a stimulus.

20. The method of claim 19, wherein said stimulus is a chemical or biological stimulus, and wherein said partition comprises said stimulus.

21. The method of claim 19, wherein said stimulus is a reducing agent.

22. The method of claim 6, further comprising subjecting said barcoded nucleic acid molecule or derivative thereof to one or more reactions prior to said sequencing.

23. The method of claim 22, further comprising recovering said barcoded nucleic acid molecule or derivative thereof from said partition and subsequently performing said one or more reactions.

24. The method of claim 22, wherein said one or more reactions comprises adding a functional sequence to said barcoded nucleic acid molecule or derivative thereof, which functional sequence permits attachment of said barcoded nucleic acid molecule or derivative thereof to a flow cell of a sequencer during said sequencing.

25. The method of claim 7, wherein said conditions sufficient to lyse said cell comprise exposing said cell beads to light.

26. The method of claim 1, further comprising:
prior to (a), partitioning a plurality of cells comprising said cell and polymer or gel precursors into a plurality of first partitions; and
subjecting said plurality of first partitions to conditions sufficient to polymerize or crosslink said polymer or gel precursors in said plurality of first partitions to generate said plurality of cell beads.

27. The method of claim 26, further comprising recovering said plurality of cell beads from said plurality of first partitions.

28. The method of claim 1, wherein said plurality of nucleic acid barcode molecules is a plurality of double-stranded nucleic acid barcode molecules.

29. The method of claim 28, further comprising performing one or more nucleic acid extension reactions on said denatured nucleic acid molecule to generate a double-stranded nucleic acid molecule comprising a sequence corresponding to said denatured nucleic acid molecule and ligating said nucleic acid barcode molecule to said double-stranded nucleic acid molecule to generate a barcoded nucleic acid molecule.

30. The method of claim 29, wherein said one or more nucleic acid extension reactions comprise:
(i) annealing a first primer to said denatured nucleic acid molecule and performing a first nucleic acid extension reaction in the presence of uracil to generate a first nucleic acid extension product comprising a uracil-containing moiety;
(ii) excising said uracil-containing moiety to generate a nick in said first nucleic acid extension product;
(iii) performing a second nucleic acid extension reaction on said first nucleic acid extension product comprising said nick to generate a plurality of single-stranded nucleic acid fragments;
(iv) annealing a second primer to a single-stranded nucleic acid fragment of said plurality of single-stranded nucleic acid fragments; and
(v) performing a third nucleic acid extension reaction to generate a second nucleic acid extension product.

31. The method of claim 30, wherein said first primer or said second primer comprises a random primer sequence.

32. The method of claim 30, wherein said second nucleic acid extension reaction is completed with use of a polymerase having strand displacement activity.

33. The method of claim 30, wherein said second nucleic acid extension reaction is a primer-independent extension process.

34. The method of claim 1, wherein a nucleic acid barcode molecule of said plurality of nucleic acid barcode molecules comprises one or more functional sequences.

35. The method of claim 34, wherein said one or more functional sequences are selected from the group consisting of: a unique molecular index (UMI), a target-specific primer sequence, a random primer sequence, a sequencing primer sequence, and a sequence configured to attach to the flow cell of a sequencer.

36. The method of claim 1, wherein said bulk processing comprises contacting said plurality of cell beads with a chemical agent.

37. The method of claim 36, wherein said chemical agent is sodium hydroxide.

* * * * *

UNITED STATES PATENT AND TRADEMARK OFFICE
CERTIFICATE OF CORRECTION

PATENT NO. : 10,428,326 B2
APPLICATION NO. : 15/887947
DATED : October 1, 2019
INVENTOR(S) : Zahra Kamila Belhocine et al.

It is certified that error appears in the above-identified patent and that said Letters Patent is hereby corrected as shown below:

On the Title Page

Item (72), Line 1, please change "Kamila Belhocine" to --Zahra Kamila Belhocine--.

Signed and Sealed this
Seventh Day of February, 2023

Katherine Kelly Vidal
Director of the United States Patent and Trademark Office